United States Patent
Wang et al.

(10) Patent No.: US 9,725,698 B2
(45) Date of Patent: Aug. 8, 2017

(54) TROPHOBLAST-DERIVED MESENCHYMAL STEM CELLS (T-MSCS) PRODUCED FROM HUMAN EMBRYONIC STEM CELLS, METHODS AND USES THEREOF

(71) Applicants: IMSTEM BIOTECHNOLOGY, INC., Farmington, CT (US); UNIVERSITY OF CONNECTICUT, Farmington, CT (US)

(72) Inventors: Xiaofang Wang, Unionville, CT (US); Ren-He Xu, Taipa (MO)

(73) Assignees: IMSTEM BIOTECHNOLOGY, INC., Farmington, CT (US); UNIVERSITY OF CONNECTICUT, Farmington, CT (US)

( * ) Notice: Subject to any disclaimer, the term of this patent is extended or adjusted under 35 U.S.C. 154(b) by 0 days.

(21) Appl. No.: 14/413,297

(22) PCT Filed: Jul. 11, 2013

(86) PCT No.: PCT/US2013/050077
§ 371 (c)(1),
(2) Date: Jan. 7, 2015

(87) PCT Pub. No.: WO2014/011881
PCT Pub. Date: Jan. 16, 2014

(65) Prior Publication Data
US 2015/0191699 A1 Jul. 9, 2015

Related U.S. Application Data

(60) Provisional application No. 61/670,192, filed on Jul. 11, 2012, provisional application No. 61/684,509, filed on Aug. 17, 2012.

(51) Int. Cl.
*C12N 5/0775* (2010.01)
*A61K 35/28* (2015.01)

(52) U.S. Cl.
CPC ........... *C12N 5/0668* (2013.01); *A61K 35/28* (2013.01); *C12N 2500/90* (2013.01); *C12N 2501/115* (2013.01); *C12N 2501/135* (2013.01); *C12N 2501/145* (2013.01); *C12N 2501/155* (2013.01); *C12N 2501/165* (2013.01); *C12N 2501/235* (2013.01); *C12N 2501/26* (2013.01); *C12N 2506/02* (2013.01); *C12N 2506/45* (2013.01); *C12N 2533/90* (2013.01)

(58) Field of Classification Search
CPC ............ C12N 2501/26; C12N 5/0668; C12N 2501/165; C12N 2501/115; C12N 2501/235; C12N 2501/145; C12N 2506/02; C12N 2500/90; C12N 2533/90; C12N 2506/45; C12N 2501/135; C12N 2501/155; A61K 35/28
See application file for complete search history.

(56) References Cited

U.S. PATENT DOCUMENTS

| | | | |
|---|---|---|---|
| 7,148,062 B2 | 12/2006 | Xu et al. | |
| 8,961,956 B2 | 2/2015 | Kimbrel et al. | |
| 8,962,321 B2 | 2/2015 | Kimbrel et al. | |
| 2009/0263361 A1* | 10/2009 | Lee ..................... | C12N 5/0605 424/93.7 |
| 2011/0088107 A1 | 4/2011 | Hanna et al. | |
| 2012/0135878 A1 | 5/2012 | Lee et al. | |

FOREIGN PATENT DOCUMENTS

| | | |
|---|---|---|
| JP | 2005520514 | 7/2005 |
| JP | 2010-94062 | 4/2010 |
| WO | WO 99/64566 A2 | 12/1999 |
| WO | WO 2007/027156 | 3/2007 |
| WO | WO 2011/025179 A2 | 3/2011 |
| WO | WO 2012/068170 A2 | 5/2012 |

OTHER PUBLICATIONS

Wu et al., JBC, 283(36): 24991-25002, 2008.*
McElroy et al., Cold Spring Harbor Protocols, 3(9): 1-4, 2008.*
Al Jumah, M.A., and Abumaree, M.H. (2012). The Immunomodulatory and Neuroprotective Effects of Mesenchymal Stem Cells (MSCs) in Experimental Autoimmune Encephalomyelitis (EAE): A Model of Multiple Sclerosis (MS). International journal of molecular sciences 13, 9298-9331.
Anton, K., Banerjee, D., and Glod, J. (2012). Macrophage-associated mesenchymal stem cells assume an activated, migratory, pro-inflammatory phenotype with increased IL-6 and CXCL10 secretion. PLoS One 7, e35036.
Auletta, J.J., Bartholomew, A.M., Maziarz, R.T., Deans, R.J., Miller, R.H., Lazarus, H.M., and Cohen, J.A. (2012). The potential of mesenchymal stromal cells as a novel cellular therapy for multiple sclerosis. Immunotherapy 4, 529-547.
Barberi, T., Willis, L.M., Socci, N.D., and Studer, L. (2005). Derivation of multipotent mesenchymal precursors from human embryonic stem cells. PLoS Med 2, e161.

(Continued)

*Primary Examiner* — Thaian N Ton
(74) *Attorney, Agent, or Firm* — Leason Ellis LLP

(57) ABSTRACT

The disclosure provided herein relates generally to mesenchymal-like stem cells "hES-T-MiSC" or "T-MSC" and the method of producing the stem cells. The method comprises culturing embryonic stem cells under conditions that the embryonic stem cells develop through an intermediate differentiation of trophoblasts, and culturing the differentiated trophoblasts to hES-T-MSC or T-MSC, T-MSC derived cells and cell lineages "T-MSC-DL" are also described. Disclosed also herein are solutions and pharmaceutical compositions comprising the T-MSC and/or T-MSC-DL, methods of making the T-MSC and T-MSC-DL, and methods of using the T-MSC and T-MSC-DL for treatment and prevention of diseases, specifically, T-MSC and T-MSC-DL are used as immunosuppressive agents to treat multiple sclerosis and autoimmune diseases.

12 Claims, 8 Drawing Sheets

(56) References Cited

OTHER PUBLICATIONS

Figure 1:
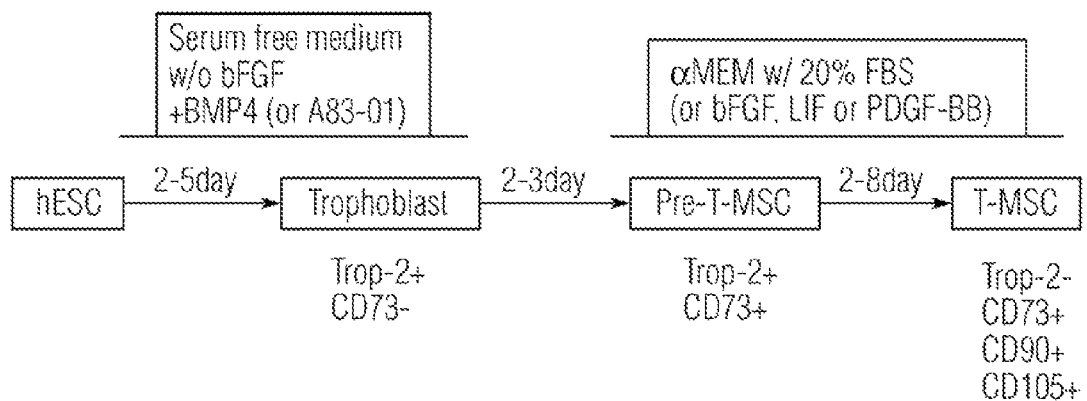

Barry, F., Boynton, RE., Uu, B., and Murphy, J.M. (2001), Chondrogenic differentiation of mesenchymal stem cells from bone marrow: differentiation-dependent gene expression of matrix components. Exp Cell Res 2.68, 189-.200.

Becher B, Durell BG, Noelle RJ (2002) Experimental autoimmune encephalitis and inflammation in the absence of interleukin-12. The Journal of clinical investigation 110: 493-497.

Benito-Leon, J. (2011). Are the prevalence and incidence of multiple sclerosis changing? Neuroepidemiology 36, 148-149.

Brown, S.E., Tong, W., and Krebsbach, P.H. (2009). The derivation of mesenchymal stem cells from human embryonic stem cells. Cells Tissues Organs 189, 256-260.

Chao, Y.X., He, B.P., and Tay, S.S. (2009). Mesenchymal stem cell transplantation attenuates blood brain barrier damage and neuroinflammation and protects dopaminergic neurons against MPTP toxicity in the substantia nigra in a model of Parkinson's disease. Journal of neuroimmunology 216, 39-50.

Chaudhary P, Marracci GH, Bourdette DN (2006) Lipoic acid inhibits expression of ICAM-1 and VCAM-1 by CNS endothelial cells and T cell migration into the spinal cord in experimental autoimmune encephalomyelitis. Journal of neuroimmunology 175: 87-96.

Chen, Y-8., Pelekanos, RA., Ellis, RL, Home, R, Wolvetang, E.J., and Fisk, N.M. (2012). Small Molecule Mesengenic Induction of Human Induced Pluripotent Stem Cells to Generate Mesenchymal Stem/Stromal Cells. Stem Cells Translational Medicine.

Chyou, S., Ekland, E.H., Carpenter, A.C., Tzeng, T.C., Tian, S., Michaud, M., Madri, J.A., and Lu, T.T. (2008). Fibroblast-type reticular stromal cells regulate the lymph node vasculature. J Immunol 181, 3887-3896.

Connick, P., Kolappan, M., Crawley, C., Webber, D.J., Patani, R., Michell, A.W., Du, M.Q., Luan,S.L., Altmann, D.R., Thompson, A.J., et al. (2012). Autologous mesenchymal stem cells for the treatment of secondary progressive multiple sclerosis: an open-label phase 2a proof-of concept study. Lancet neurology 11, 150-156.

Correale, J., and Villa, A. (2007). The blood-brain-barrier in multiple sclerosis: functional roles and therapeutic targeting. Autoimmunity 40, 148-160.

Costa, M., Dottori, M., Ng, E., Hawes, S.M., Sourris, K., Jamshidi, P., Pera, M.F., Elefanty, A.G.,and Stanley, E.G. (2005). The hESC line Envy expresses high levels of GFP in all differentiated progeny. Nat Methods 2, 259-260.

Crocker. S.J., Milner, R., Pham-Mitchell, N., and Campbell, LL. (2006). Cell and agonist-specific regulation of genes for matrix metalloproteinases and their tissue inhibitors by primary glial cells. Journal of neurochemistry 98, 812-823.

Cuccurullo C, Iezzi A, Fazia ML, De Cesare D, Di Francesco A, et al. (2006) Suppression of RAGE as a basis of simvastatin-dependent plaque stabilization in type 2 diabetes. Arteriosclerosis, thrombosis, and vascular biology 26: 2716-2723.

Cunnea P, McMahon J, O'Connell E, Mashayekhi K, Fitzgerald U, et al. (2010) Gene expression analysis of the microvascular compartment in multiple sclerosis using laser microdissected blood vessels. Acta neuropathologica 119: 601-615.

Dai H, Ciric B, Zhang GX, Rostami A (2012) Interleukin-10 plays a crucial role in suppression of experimental autoimmune encephalomyelitis by Bowman-Birk inhibitor. Journal of neuroimmunology 245: 1-7.

Dienz, O., and Rincon, M. (2009). The effects of IL-6 on CD4 T cell responses. Clinical immunology 130, 27-33.

Djouad, F., Plence, P., Bony, C., Tropel, P., Apparailly, F., Sany, J., Noel, D., and Jorgensen, C. (2003). Immunosuppressive effect of mesenchymal stem cells favors tumor growth in allogeneic animals. Blood 102, 3837-3844.

Dong, C. (2008). TH17 cells in development: an updated view of their molecular identity and genetic programming. Nat Rev Immunol 8, 337-348.

Draper, J.S., Pigott, C., Thomson, J.A., and Andrews, P.W. (2002). Surface antigens of human embryonic stem cells: changes upon differentiation in culture. Journal of anatomy 200, 249-258.

Drukker, M., Katchman, H., Katz, G., Even-Tov Friedman, S., Shezen, E., Hornstein, E., Mandelboim, O., Reisner, Y., and Benvenisty, N. (2006). Human embryonic stem cells and their differentiated derivatives are less susceptible to immune rejection than adult cells, Stem Cells 24, 221-229.

Drukker, M., Katz, G., Urbach, A., Schuldiner, M., Markel, G., Itskovitz-Eldor, J., Reubinoff, B., Mandelboim, O., and Benvenisty, N. (2002). Characterization of the expression of MHC proteins in human embryonic stem cells. Proceedings of the National Academy of Sciences of the United States of America 99, 9864-9869.

English, K., Barry, F.P., Field-Corbett, C.P., and Mahon, B.P. (2007). IFN-gamma and TNF alpha differentially regulate immunomodulation by murine mesenchymal stem cells. Immunol Lett 110, 91-100.

Ge, S., Shrestha, B., Paul, D., Keating, C., Cone, R., Guglielmotti, A., and Pachter, J.S. (2012). The CCL2 synthesis inhibitor bindarit targets cells of the neurovascular unit, and suppresses experimental autoimmune encephalomyelitis. J Neuroinflammation 9, 171.

Gijbels, K., Brocke, S., Abrams, J.S., and Steinman, L. (1995). Administration of neutralizing antibodies to interleukin-6 (IL-6) reduces experimental autoimmune encephalomyelitis and is associated with elevated levels of IL-6 bioactivity in central nervous system and circulation. Mol Med 1, 795-805.

Gordon, D., Pavlovska, G., Glover, C.P., Uney, J.B., Wraith, D., and Scolding, N.J. (2008b). Human mesenchymal stem cells abrogate experimental allergic encephalomyelitis after intraperitoneal injection, and with sparse CNS infiltration. Neuroscience letters 448, 71-73.

Gordon, D., Pavlovska, G., Uney, J.B., Wraith, D.C., and Scolding, N.J. (2010). Human mesenchymal stem cells infiltrate the spinal cord, reduce demyelination, and localize to white matter lesions in experimental autoimmune encephalomyelitis. J Neuropathol Exp Neurol 69, 1087-1095.

Grinnemo, K.H., Mansson, A., Dellgren, G., Klingberg, D., Wardell, E., Drvota, V., Tammik, C., Holgersson, J., Ringden, O., Sylven, C., et al. (2004). Xenoreactivity and engraftment of human mesenchymal stem cells transplanted into infarcted rat myocardium. J Thorac Cardiovasc Surg 127, 1293-1300.

Hofstetter, C.P., Schwarz, E.J., Hess, D., Widenfalk, J., El Manira, A., Prockop, D.J., and Olson, L. (2002). Marrow stromal cells form guiding strands in the injured spinal cord and promote recovery. Proceedings of the National Academy of Sciences of the United States of America 99, 2199-2204.

Huber, T.L., Kouskoff, V., Fehling, H.J., Palis, J., and Keller, G. (2004). Haemangioblast commitment is initiated in the primitive streak of the mouse embryo. Nature 432, 625-630.

Hwang, N.S., Varghese, S., Lee, H.J., Zhang, Z., Ye, Z., Bae, J., Cheng, L., and Elisseeff, J. (2008). In vivo commitment and functional tissue regeneration using human embryonic stem cell derived mesenchymal cells. Proc Natl Acad Sci U S A 105, 20641-20646.

Huss DJ, Winger RC, Cox GM, Guerau-de-Arellano M, Yang Y, et al. (2011) TGF-beta signaling via Smad4 drives IL-10 production in effector Th1 cells and reduces T-cell trafficking in EAE. European journal of immunology 41: 2987-2996.

Javazon, E.H., Beggs, K.J., and Flake, A.W. (2004). Mesenchymal stem cells: paradoxes of passaging. Exp Hematol 32, 414-425.

Karlsson, C., Emanuelsson, K., Wessberg, F., Kajic, K., Axell, M.Z., Eriksson, P.S .. Lindahl, A., Hyllner, J., and Strehl, R. (2009). Human embryonic stem cell-derived mesenchymal progenitorsPotential in regenerative medicine. Stem Cell Res 3, 39-50.

Karussis, D., Karageorgiou, C., Vaknin-Dembinsky, A., Gowda-Kurkalli, B., Gomori, J.M., Kassis, I., Bulte, J.W., Petrou, P., Ben-Hur, T., Abramsky, O., et al. (2010). Safety and immunological effects of mesenchymal stem cell transplantation in patients with multiple sclerosis and amyotrophic lateral sclerosis. Arch Neurol 67, 1187-1194.

(56) References Cited

OTHER PUBLICATIONS

Klimanskaya, I., Chung, Y., Becker, S., Lu, S.J., and Lanza, R. (2006). Human embryonic stem cell lines derived from single blastomeres. Nature 444, 481-485.
Leech, M.D., Barr, T.A., Turner, D.G., Brown, S., O'Connor, R.A., Gray, D., Mellanby, R.J., and Anderton, S.M. (2012). Cutting Edge: IL-6-Dependent Autoimmune Disease: Dendritic Cells as a Sufficient, but Transient, Source. J Immunol., 2013; 190:881-885.
Lin, G., Martins-Taylor, K., and Xu, R.H. (2010). Human embryonic stem cell derivation, maintenance, and differentiation to trophoblast. Methods in molecular biology 636, 1-24.
Liu, R., Zhang, Z., Lu, Z., Borlongan, C., Pan, J., Chen, J., Qian, L., Liu, Z., Zhu, L., Zhang, J., et al. (2012). Human Umbilical Cord Stem Cells Ameliorate Experimental Autoimmune Encephalomyelitis by Regulating Immunoinflammation and Remyelination. Stem cells and development; 2013; vol. 22, No. 7, pp. 1053-1062.
Lu, S.J., Feng, Q., Caballero, S., Chen, Y., Moore, M.A., Grant, M.B., and Lanza, R. (2007). Generation of functional hemangioblasts from human embryonic stem cells. Nat Methods 4, 501-509.
Liu, Y., Goldberg, AJ., Dennis, J.E., Gronowicz, G.A, and Kuhn, L.T. (2012). One-step derivation of mesenchymal stem cell (MSC)-like cells from human pluripotent stem cells on a fibrillar collagen coating. PLoS One 7, e33225.
Lu, S.J., Luo, C., Holton, K., Feng, Q., Ivanova, Y., and Lanza, R. (2008). Robust generation of hemangioblastic progenitors from human embryonic stem cells. Regen Med 3, 693-704.
Ludwig TE, Levenstein ME, Jones JM, Berggren WT, Mitchen ER, et al. (2006) Derivation of human embryonic stem cells in defined conditions. Nat Biotechnol 24: 185-187.
Mahad DJ, Ransohoff RM (2003) The role of MCP-1 (CCL2) and CCR2 in multiple sclerosis and experimental autoimmune encephalomyelitis (EAE). Seminars in immunology 15: 23-32.
McFarland, H.F., and Martin, R. (2007). Multiple sclerosis: a complicated picture of autoimmunity. Nat Immunol 8, 913-919.
Menge, T., Zhao, Y., Zhao, J., Wataha, K., Gerber, M., Zhang, J., Letourneau, P., Redell, J., Shen, L., Wang, J., et al. (2012). Mesenchymal Stem Cells Regulate Blood-Brain Barrier Integrity Through TIMP3 Release After Traumatic Brain Injury. Science translational medicine 4, 161ra150.
Minagar, A., Maghzi, A.H., McGee, J.C., and Alexander, J.S. (2012). Emerging roles of endothelial cells in multiple sclerosis pathophysiology and therapy. Neurological research 34, 738-745.
Mohyeddin Bonab, M., Yazdanbakhsh, S., Lotfi, J., Alimoghaddom, K., Talebian, F., Hooshmand, F., Ghavamzadeh, A., and Nikbin, B. (2007). Does mesenchymal stem cell therapy help multiple sclerosis patients? Report of a pilot study. Iranian journal of immunology; IJI 4, 50-57.
Moore. C.S., Milner, R., Nishiyama, A., Frausto, R.F., Serwanski, D.R., Pagarigan, R.R., Whitton, J.L, Miller, R.H., and Crocker, S.J. (2011), Astrocytic tissue inhibitor of metalloproteinase-1 (TIMP-1) promotes oligodendrocyte differentiation and enhances CNS myelination. The Journal of neuroscience : the official journal of the Society for Neuroscience 31, 6247-6254.
Morando, S., Vigo, T., Esposito, M., Casazza, S., Novi, G., Principato, M.C., Furlan, R., and Uccelli, A. (2012). The therapeutic effect of mesenchymal stem cell transplantation in experimental autoimmune encephalomyelitis is mediated by peripheral and central mechanisms. Stem Cell Res Ther 3, 3.
Ohtaki, H., Ylostalo, J.H., Foraker, J.E., Robinson, A.P., Reger, R.L., Shioda, S., and Prockop, D.J. (2008). Stem/progenitor cells from bone marrow decrease neuronal death in global ischemia by modulation of inflammatory/immune responses. Proc Natl Acad Sci U S A 105, 14638-14643.
Olivier, E.N., Rybicki, A.C., and Bouhassira, E.E. (2006). Differentiation of human embryonic stem cells into bipotent mesenchymal stem cells. Stem Cells 24, 1914-1922.
Patanella, A.K., Zinno, M., Quaranta, D., Nociti, V., Frisullo, G., Gainotti, G., Tonali, P.A., Batocchi, A.P., and Marra, C. (2010). Correlations between peripheral blood mononuclear cell production of BDNF, TNF-alpha, IL-6, IL-10 and cognitive performances in multiple sclerosis patients. J Neurosci Res 88, 1106-1112.
Payne, N.L., Sun, G., McDonald, C., Layton, D., Moussa, L., Emerson-Webber, A., Veron, N., Siatskas, C., Herszfeld, D., Price, J., et al. Distinct immunomodulatory and migratory mechanisms underpin the therapeutic potential of human mesenchymal stem cells in autoimmune demyelination. Cell Transplant; 2013; vol. 22, pp. 1409-1425.
Peron, J.P., Jazedje, T., Brandao, W.N., Perin, P.M., Maluf, M., Evangelista, L.P., Halpern, S., Nisenbaum, M.G., Czeresnia, C.E., Zatz, M., et al. (2012). Human endometrial-derived mesenchymal stem cells suppress inflammation in the central nervous system of EAE mice. Stem Cell Rev 8, 940-952.
Pittenger, M.F., Mackay, A.M., Beck, S.C., Jaiswal, R.K., Douglas, R., Mosca, J.D., Moorman, M.A., Simonetti, D.W., Craig, S., and Marshak, D.R. (1999). Multilineage potential of adult human mesenchymal stem cells. Science 284, 143-147.
Pomper, M.G., Hammond, H., Yu, X., Ye, Z., Foss, C.A., Lin, D.D., Fox, J.J., and Cheng, L. (2009).Serial imaging of human embryonic stem-cell engraftment and teratoma formation in live mouse models. Cell Res 19, 370-379.
Quintana, A., Muller, M., Frausto, R.F., Ramos, R., Getts, D.R., Sanz, E., Hofer, M.J., Krauthausen, M., King, N.J., Hidalgo, J., et al. (2009). Site-specific production of IL-6 in the central nervous system retargets and enhances the inflammatory response in experimental autoimmune encephalomyelitis. Journal of immunology 183, 2079-2088.
Rafei, M., Birman, E., Forner, K., and Galipeau, J. (2009a). Allogeneic mesenchymal stem cells for treatment of experimental autoimmune encephalomyelitis. Mol Ther 17, 1799-1803.
Rafei, M., Campeau, P.M., Aguilar-Mahecha, A., Buchanan, M., Williams, P., Birman, E., Yuan, S., Young, Y.K., Boivin, M.N., Forner, K., et al. (2009b). Mesenchymal stromal cells ameliorate experimental autoimmune encephalomyelitis by inhibiting CD4 Th17 T cells in a CC chemokine ligand 2-dependent manner. J Immunol 182, 5994-6002.
Rochman, I., Paul, W.E., and Ben-Sasson, S.Z. (2005). IL-6 increases primed cell expansion and survival. Journal of immunology 174, 4761-4767.
Ryan, J.M., Barry, F., Murphy, J.M., and Mahon, B.P. (2007). Interferon-gamma does not break, but promotes the immunosuppressive capacity of adult human mesenchymal stem cells. Clin Exp Immunol 149, 353-363.
Sanchez, L., Gutierrez-Aranda, I., Ligero, G., Rubio, R., Munoz-Lopez, M., Garcia-Perez, J.L., Ramos, V., Real, P.J., Bueno, C., Rodriguez, R., et al. (2011). Enrichment of human ESC derived multipotent mesenchymal stem cells with immunosuppressive and anti-inflammatory properties capable to protect against experimental inflammatory bowel disease. Stem Cells 29, 251-262.
Sethe, S., Scutt, A., and Stolzing, A. (2006). Aging of mesenchymal stem cells. Ageing Res Rev 5, 91-116.
Solchaga, L.A., Penick, K.J., and Welter, J.F. (2011). Chondrogenic differentiation of bone marrow-derived mesenchymal stem cells: tips and tricks. Methods in molecular biology 698, 253-278.
Stromnes, I.M., and Goverman, J.M. (2006). Active induction of experimental allergic encephalomyelitis. Nat Protoc 1, 1810-1819.
Thomson, J.A., ltskovitz-Eldor, J., Shapiro, S.S., Waknitz, M.A., Swiergiel, J.J., Marshall, V.S., and Jones, J.M. (1998). Embryonic stem cell lines derived from human blastocysts. Science 282, 1145-1147.
Tse, W.T., Pendleton, J.D., Beyer, W.M., Egalka, M.C., and Guinan, E.G. (2003). Suppression of allogeneic T-cell proliferation by human marrow stromal cells: implications in transplantation. Transplantation 75, 389-397.
Tyndall, A. (2011). Successes and failures of stem cell transplantation in autoimmune diseases. Hematology Am Soc Hematol Educ Program 2011, 280-284.
Uccelli, A., and Prockop, D.J. (2010a). Why should mesenchymal stem cells (MSCs) cure autoimmune diseases? Curr Opin Immunol 22, 768-774.
Uccelli, A., and Prockop, D.J. (2010b). Why should mesenchymal stem cells (MSCs) cure autoimmune diseases? Curr Opin Immunol, 2010, 22:768-774.

(56) References Cited

OTHER PUBLICATIONS

Waterman, R.S., Tomchuck, S.L., Henkle, S.L., and Betancourt, A.M. (2010). A new mesenchymal stem cell (MSC) paradigm: polarization into a pro-inflammatory MSC1 or an Immunosuppressive MSC2 phenotype. PLoS One 5, 2010; vol. 5, Issue 4, e10088; pp. 1-14.
Wong, R.S. (2011). Mesenchymal stem cells: angels or demons? J Biomed Biotechnol 2011, 459510.
Xu, Rh., Chen, X., U, D.S., Li, R., Addicks, G.C., Glennon, C., Zwaka, T.P and Thomson, J.A. (2002). BMP4 initiates human embryonic stem cell differentiation to trophoblast. Nat Biotechnol, 20, 1261-1264.
Yamout, B., Hourani, R., Salti, H., Barada, W., El-Hajj, T., Al-Kutoubi, A., Herlopian, A., Baz, E.K., Mahfouz, R., Khalil-Hamdan, R., et al. (2010). Bone marrow mesenchymal stem cell transplantation in patients with multiple sclerosis: a pilot study. J Neuroimmunol 227, 185-189.
Zappia, E., Casazza, S., Pedemonte, E., Benvenuto, F., Bonanni, I., Gerdoni, E., Giunti, D., Ceravolo, A., Cazzanti, F., Frassoni, F., et al. (2005). Mesenchymal stem cells ameliorate experimental autoimmune encephalomyelitis inducing T-cell anergy. Blood 106, 1755-1761.
Zhang, J., Li, Y., Chen, J., Cui, Y., Lu, M., Elias, S.B., Mitchell, J.B., Hammill, L., Vanguri, P., and Chopp, M. (2005). Human bone marrow stromal cell treatment improves neurological functional recovery in EAE mice. Exp Neurol 195, 16-26.
Hematti Peiman: "Human embryonic stem cell-derived mesenchymal progenitors: an overview", Methods in Molecular Biology, Humana Press, Inc, US, vol. 690, Jan. 1, 2011 (Jan. 1, 2011), pp. 163-174.
Laura Sanchez et al: "Enrichment of Human 6-15 ESC-Derived Multipotent Mesenchymal Stem Cells with Immunosuppressive and Anti-Inflarrmatory Properties Capable to Protect Against Experimental Inflammatory Bowel Disease", Stem Cells, vol . 29, No. 2, Feb. 1, 2011 (Feb. 1, 2011), pp. 251-262.
Romain Barbet et al: "Comparison of Gene 6-15 Expression in Human Embryonic Stem Cells, hESC-Derived Mesenchymal Stem Cells and Human Mesenchymal Stem Cells", Stem Cells International, vol . 78, No. 11, Jan. 1, 2011 (Jan. 1, 2011), pp. 2848-2849.
Rongrong Wu et al: "Derivation of 6-15 multipotent nestin+/CD271-/STRO-Imesenchymal-like precursors from human embryonic stem cells in chemically defined conditions," Human Cell, vol. 26, No. 1, Jun. 15, 2011 (Jun. 15, 2011), pp. 19-27.
Tan Z et al: "Tiunomodulative effects of 6-15 mesenchymal stem cells derived from human embryonic stem cells in vivo and in vitro" Zhejiang University. Journal. Science B: International Biomedicine & Biotechnology Journal, Zheijiang University Press, CN, vol . 12, No. I, Jan. 1, 2011 (Jan. 1, 2011), pp. 18-27.
Teresa M. Erb et al: "Paracrine and Epigenetic Control of Trophectoderm Differentiation from Human Embryonic Stem Cells: The Role of Bone Morphogenic Protein 4 and Histone Deacetylases" Stem Cells and Development, vol. 20, No. 9, Sep. 1, 2011 (Sep. 1, 2011), pp. 1601-1614.
Das et al: "Effects of FGF2 and oxygen in the BMP4-driven differentiation of trophoblast from human embryonic stem cells", Oct. 1, 2007, vol. 1, No. 1, Oct. 1, 2007 (Oct. 1, 2007), pp. 61-74.
European Search Report of Application No. EP 13 81 6490, dated Jan. 28, 2016.
Kern, S et al. Comparative Analysis of Mesenchymal Stem Cells from Bone Marrow. Stem, Cells. Jan. 12, 2006, vol. 24, No. 5, pp. 1294-1301; p. 1299, right column, second paragraph; DOI: 10.1634/stemcells.2005-0342.
Batrakova, EV et al. Cell-Mediated Drugs Delivery. Expert Opin Drug Deliv. Feb. 24, 2011, vol. 8, No. 4, pp. 415-433; Retrieved from: PMC; p. 9.
Guan, XQ, et al. Study on Mesenchymal Stem Cells Entering the Brain Through the Blood-Brain Barrier. Zhonghua Er Ke Za Zhi. Dec. 2004, vol. 42, No. 12; pp. 920-923.
International Search Report in corresponding PCT Application No. PCT/US2013/050077, mailed Feb. 10, 2014.
International Preliminary Report and Written Opinion in corresponding PCT Application No. PCT/US2013/050077, mailed Feb. 10, 2014.
Yen Shun Chen et al., "Small Molecule Mesengic Induction of Human Induced Pluripotent Stem Cells to Generate Mesenchymal Stem/Stromal Cells", Stem Cells Transl Med, vol. 1, Issue 2, 83-95.
Chinese Office Action in corresponding of Application No. 201380036985.7, issued Apr. 5, 2016.
Marcos de Lima, et al., Cord-Blood Engraftment with Ex Vivo Mesenchymal-Cell Coculture, The New England Journal of Medicine, 2012; 367;24: pp. 2305-2315.
Susanne Kern, et al., "Comparative Analysi of Msenchymal Stem Cells from Bone Marrow, Umbilical Cord Blood, or Adipose Tissue", Stem Cells, 2006; 24: pp. 1294-1301.
Hansen, W., Westendorf, A.M., and Buer, J. (2008). Regulatory T cells as targets for immunotherapy of autoimmunity and inflammation. Inflamm Allergy Drug Targets 7, 217-223.
Johnston, J., and So, T.Y. (2012). First-line disease-modifying therapies in paediatric multiple sclerosis: a comprehensive overview. Drugs 72, 1195-1211.
Kurtzke JF (1983). "Rating neurologic impairment in multiple sclerosis: an expanded disability status scale (EDSS)". Neurology 33 (11): 1444-52.
Lu, S.J., Ivanova, Y., Feng, Q., Luo, C., and Lanza, R. (2009). Hemangioblasts from human embryonic stem cells generate multilayered blood vessels with functional smooth muscle cells. Regenerative medicine 4, 37-47.
Mohyeddin Bonab, M., Yazdanbakhsh, S., Lotfi, J., Alimoghaddom, K., Talebian, F., Hooshmand, F., Ghavamzadeh, A., and Nikbin, B. (2007). Does mesenchymal stem cell therapy help multiple sclerosis patients? Report of a pilot study. Iranian journal of immunology : IJI 4, 50-57.
Weber, M.S., Menge, T., Lehmann-Horn, K., Kronsbein, H.C., Zettl, U., Sellner, J., Hemmer, B., and Stuve, O. (2012). Current treatment strategies for multiple sclerosis—efficacy versus neurological adverse effects. Current pharmaceutical design 18, 209-219.
Tony Tung-Yin Lee, et al., "Ectopic Pregnancy-Derived Human Trophoblastic Stem Cells Regenerate Dopaminergic Nigrostriatal Pathway to Treat Parkinsonian Rats," Plos One, Dec. 2012, vol. 7, Issue 12, pp. 1-15.
Xiaofan Wang, et al. "Immune Modulatory Mesenchymal Stem Cells Derived from Human Embryonic Stem Cells Derived from Human Embryonic Stem Cells Through a Trophoblast-Like Stage," Stem Cells, 2016, 34: pp. 380-391.
Chinese Office Action in corresponding Application No. 201380036985.7, dated Feb. 13, 2017.
Japanese Office Action in corresponding Japanese Application No. 2015-521809 dated May 23, 2017.
Australian Office Action in corresponding Australian Application No. 2013290146, dated May 25,2017.

* cited by examiner

TROPHOBLAST-DERIVED MESENCHYMAL STEM CELLS (T-MSCS) PRODUCED FROM HUMAN EMBRYONIC STEM CELLS, METHODS AND USES THEREOF

CROSS-REFERENCE TO RELATED PATENT APPLICATIONS

This application is a U.S. National Phase Application under 35 U.S.C. §371 of International Patent Application No. PCT/US2013/050077, filed Jul. 11, 2013, and claims the benefit of priority under 35 U.S.C. Section 119(e) of U.S. Application Ser. No. 61/670,192, filed Jul. 11, 2012 and U.S. Application Ser. No. 61/684,509, filed Aug. 17, 2012, all of which are incorporated by reference in their entireties. The International Application was published on Jan. 16, 2014 as International Publication No. WO 2014/011881 A2.

1. INTRODUCTION

The disclosure provided herein relates generally to mesenchymal-like stem cells "hES-T-MSC" or "T-MSC" and the method of producing the stem cells. The method comprises culturing embryonic stem cells under conditions that the embryonic stem cells develop through an intermediate differentiation of trophoblasts, and differentiating trophoblasts into hES-T-MSC or T-MSC. Disclosed herein are the T-MSC, solutions and pharmaceutical compositions comprising the T-MSC, methods of making the T-MSC, methods of using the T-MSC for treatment and prevention of diseases, specifically, T-MSC are used as an immunosuppressive agent to treat multiple sclerosis and other autoimmune diseases, for tissue regeneration/repair uses, and methods of using the T-MSC for the delivery of agents across the blood brain barrier and the blood spinal cord barrier. Also disclosed herein are methods of using T-MSCs to modulate the immune system, inhibit immune response to an individual's self-antigen and repair damaged central nervous systems. Compositions comprising T-MSCs for use in immunomodulation are disclosed herein, as are methods of providing modified T-MSC with improved immunosuppressive function through modified gene expression.

2. BACKGROUND

Human mesenchymal stem/stromal cells (MSCs) have been widely used for immune system regulation and tissue repair. Human embryonic stem cells (hESCs) can be used as a reliable source for generating high-quality human MSCs. There are many methods to differentiate hESCs into MSCs. However, current methods are not able to conduct such differentiation in an efficient manner to produce a high yield of high purity MSCs.

Mesenchymal stem cells (MSCs) derived from adult mouse or human tissues such as bone marrow, umbilical cord and fat tissue are multipotent, i.e., capable of generating a variety of mature cell lineages including adipocytes, chondrocytes, osteoblast cells, neural lineage cells, myoblast, stromal cells and fibroblast, etc. These technologies have been well characterized and patented. For example, see Caplan et al., U.S. Pat. No. 5,486,359 (human mesenchymal stem cells).

However, the currently available adult tissue-derived MSCs have several pitfalls. First, the limited sources and varying quality of the donor tissues such as the bone marrow restrict the study and application of the MSCs and prevent the standardization of the MSCs as a medical product for large-scale clinical use. Second, the MSCs obtained from the adult tissues are highly mixed populations of cells, in which only a small portion of the cells have strong immunosuppressive effect. To obtain enough cell numbers for clinical use, in vitro expansion is necessary, which can decrease the immunosuppressive and homing abilities of MSCs (Javazon et al., 2004). Third, there are safety issues regarding to the use of adult-derived MSCs including malignant transformation (Wong, 2011) and potential transmission of infectious pathogens from donors.

To overcome these pitfalls, scientists have attempted to derive MSCs from hESCs via various methods. These methods involve either co-culture with the mouse OP9 cell line or handpicking plus the use of multiple cytokines and chemicals (Barbed et al., 2005; Chen et al., 2012; Liu et al., 2012; Sanchez et al., 2011). Recently, a TGFβ signaling inhibitor SB431542 has been used to differentiate hESCs into MSCs, which simplifies the procedures and improves the efficiency (Chen et al., 2012), but the yield and purity are quite low (see the below-described comparison tests). In 2010, the inventors and Advanced Cell Technology developed another method to derive MSC from hemangioblast, which involved the use of many expensive cytokines and methylcellulose medium, but the derivation efficiency is also low using this method.

Currently known methods for differentiation of hESCs into MSCs are each characterized as having one or more serious shortcomings and weaknesses: Differentiation of MSCs from hESCs co-cultured with the OP9 stromal cells has the disadvantages of being time consuming, producing cells of low yield, low purity, and using animal feeder cells and undefined culture conditions (Barbed et al., 2005). Differentiation from outgrowing cells around replated embryoid bodies formed by hESCs has the disadvantages of being time consuming, producing cells in low yield, using undefined culture condition, and being an expensive method (Olivier et al., 2006). Differentiation from hESCs cultured on collagen-coated plates has the disadvantages of very low yield, undefined culture conditions, and being time consuming (Liu et al., 2012). Differentiation with hESCs treated with inhibitors of TGFβ signaling has the disadvantages including low purity of cells (per our tests), low cell yield, time consuming method, and low immunosuppressive effect of the cells that are produced (Chen et al., 2012; Sanchez et al., 2011). Thus, there is a need for an unlimited, safe, highly stable, efficient and consistent source of MSCs to use as a treatment and prophylactic for various diseases.

Multiple sclerosis (MS) is a chronic autoimmune disease caused by infiltration of peripheral immune cells into the central nervous system (CNS) through damaged blood-brain barrier (BBB) or blood-spinal cord barrier (BSCB), which causes inflammation of the myelin sheaths around neuronal axons, and causes demyelination and scarring of the axons (McFarland and Martin (2007)). According to the National Multiple Sclerosis Society of United States, there are more than 70 FDA-approved medications for the treatment of MS, including Avonex (IFNβ-1a), Betaseron (IFNβ-1b), Gilenya (a sphingosine 1-phosphate receptor modulator), Glatiramer acetate (or Copolymer 1), and Tysabri (humanized anti-α-integrin antibody). However, these offer only palliative relief and are associated with serious adverse effects including increased infection, heart attack, stroke, progressive multifocal leukoencephalopathy, arrhythmia, pain, depression, fatigue, macula edema, and erectile dysfunction (Johnston and So (2012); Weber et al. (2012)).

Transplantation of mesenchymal stromal/stem cells (MSCs) has emerged as a potentially attractive therapy due to their immunomodulatory and neuroregenerative effects (Auletta et al., (2012); Pittenger et al. (1999)) and potential ability to repair the blood-brain barrier (Chao et al. (2009); Menge et al. (2012)). MSCs are multipotent meaning they can generate a variety of cell lineages including adipocyte, chondrocyte, osteoblast cells and neurons. They can be derived from fetal, neonatal, and adult tissues such as the amniotic membrane, umbilical cord, bone marrow, and adipose. MSCs have several unique advantages over current pharmacotherapies, as these cells can serve as carriers of multiple and potentially synergistic therapeutic factors, and can migrate to injured tissues to exert local effects through secretion of mediators and cell-cell contact (Uccelli and Prockop (2010a)). Importantly, MSCs have been found efficacious in the treatment of mice with experimental auto-immune encephalomyelitis (EAE), a well-recognized animal model of MS (Gordon et al., 2008a; Gordon et al. (2010); Morando et al. (2012); Peron at al. (2012); Zappia et al. (2005); Zhang et al. (2005)), as well as MS patients in clinical trials (Connick et al. (2012); Karussis et al. (2010); Mohyeddin Bonab et al. (2007); Yamout et al. (2010)). Xenogeneity does not appear problematic as both mouse and human bone marrow-derived MSC (BM-MSC) can attenuate disease progression of EAE mice (Gordon et al. (2008a); Gordon et al. (2010); Morando et al. (2012); Peron et al. (2012); Zappia et al. (2005); Zhang et al. (2005)). However, varying effects were reported on EAE mice treated with BM-MSC in different reports (Gordon et al. (2008a); Payne et al. (2012); Zappia et al. (2005); Zhang et al. (2005)). The efficacy of BM-MSC on treatment of the disease is questionable.

There is a strong need for an unlimited, safe, highly stable, efficient and consistent source of MSC to use as a treatment and prophylactic for these diseases as well as others. Disclosed herein are hES-T-MSCs derived from hESCs through a highly efficient differentiation method that meets these needs. Also disclosed herein are a microarray analysis and other analysis, where several key factors are identified that are differentially expressed in hES-T-MSC compared to BM-MSC and other hES-MSC differentiated through other methods.

3. SUMMARY

Disclosed herein is a method to derive mesenchymal-like stem cells from hESCs through an intermediate step of trophoblast induction. The MSCs derived via this method are called "hES-T-MSC" or "T-MSC". The T-MSC may be differentiated into cells or cell lineages including, but not limited to, adipocytes, myoblast cells, neuron cells, osteoblast cells, fibroblast, chondrocytes, stromal cells The T-MSC derived cells or cell lineages or called "T-MSC derived lineages" or "T-MSC-DL".

Disclosed herein are compositions, including compositions comprising T-MSC and/or T-MSC-DL, having immunosuppressive properties. Described herein are populations of T-MSC and/or T-MSC-DL selected on the basis of their ability to modulate an immune response, and compositions having immunomodulatory properties. As disclosed herein, T-MSC and/or T-MSC-DL have higher immunosuppressive activity compared to bone marrow-derived MSCs.

Disclosed herein is a method to efficiently produce T-MSC in high purity and high yield. The method has the features of relatively few steps and fewer required differentiation factors than previously reported.

Disclosed herein are methods of using human embryonic stem cells (hESCs) to derive mesenchymal-like stem cells through an intermediate differentiation of trophoblasts. The MSCs derived from trophoblasts are called hES-T-MSC or T-MSC. The T-MSC can be used to modulate the immune system. For example, they are effective in treating multiple sclerosis by preventing immune cell-caused damage in the central nervous systems.

Disclosed herein are human embryonic-derived mesenchymal stem cells produced by the methods disclosed herein.

Disclosed herein are methods to induce differentiation of T-MSC into T-MSC-DL.

Also disclosed herein is the application of the T-MSC and/or T-MSC-DL to treat multiple sclerosis and other autoimmune diseases in mammals and especially in human subjects.

It is a further object of the disclosed invention to provide a cell product T-MSC for use in immunomodulation, for example, for prevention or inhibition of immunorejection during tissue or organ transplantation. In another specific embodiment of the method of reducing or suppressing an immune response, the immune response is graft-versus-host disease. In another specific embodiment, the immune response is an autoimmune disease, e.g., diabetes, lupus erythematosus, or rheumatoid arthritis.

It is a further object of the disclosed invention to provide a cell product T-MSC-DL for use in treatment of neural diseases.

The method can employ as many stem cells provided herein as are required to effect a detectable suppression of an immune response. For example, the plurality of stem cells provided herein used to contact the plurality of immune cells can comprise $1\times10^5$ T-MSC, $1\times10^6$ T-MSC, $1\times10^7$ T-MSC, $1\times10^8$ T-MSC or more.

In one embodiment, the method described herein is a novel process for deriving (also referred to herein as producing) MSCs from hESCs. The method comprising the steps of:
  a. Culturing a cell culture comprising human embryonic stem cells in serum-free medium in the present of at least one growth factor in an amount sufficient to induce the differentiation of the embryonic stem cells to differentiate into trophoblasts; in an embodiment, the time period of the differentiation into trophoblasts is about 2-5 days; in an embodiment, the medium comprises BMP4, with or without the presence of a TGFβ inhibitor (i.e. SB431542, A83-01 or ALK5 inhibitor, etc.) to increase the differentiation efficiency;
  b. Adding at least one growth factor to the culture comprising the trophoblasts and continuing to culture in serum-free medium, wherein the growth factor is in an amount sufficient to expand the trophoblasts, in an embodiment, the medium comprises BMP4 (this step is optional);
  c. Isolating the trophoblasts and re-plating the trophoblasts onto gelatin, laminin, fibronectin, vitronectin, collagen or Matrigel-coated plates and cultured in a serum-containing or serum-free media in an amount sufficient to differentiate the trophoblasts into T-MSC through pre-T-MSC, in an embodiment, the isolated trophoblasts are cultured for 4-10 days to produce the T-MSC, wherein at least about 90%, 95%, 96%, 97%, 98%, 99% of the resulting T-MSC express cell surface markers for adult MSCs, in an embodiment, the medium comprises LIF, bFGF, or PDGF to increase expansion efficiency.

In a specific embodiment, the trophoblasts derived from hESC express Trop-2, but not CD73.

In a specific embodiment, the pre-T-MSC express Trop-2 and/or CD73.

In a specific embodiment, the T-MSC express CD73⁺CD105⁺CD90⁺. It is an object of the disclosed method to differentiate hESCs into MSCs of high purity. In a preferred embodiment, CD73⁺CD105⁺CD90⁺ T-MSC are produced with greater than 90%, 95%, 96%, 97%, 98%, 99% purity.

A large number of T-MSC with high purity is demonstrated by the observation that high percentages of the MSCs express cell-surface markers for adult MSCs. The MSCs have higher immunosuppressive effect both in vitro and in vive than MSCs obtained via other methods. The MSCs derived via this currently disclosed method are named hES-trophoblast-derived MSCs and are more briefly referred to herein as T-MSC.

In certain embodiments, the serum-containing medium contains fetal calf serum or human AB serum, L-glutamine and the serum-free medium contains knockout serum replacement (KOSR) or bovine serum albumin (BSA).

In certain embodiments, there is an additional step of irradiating the resulting T-MSC with gamma radiation ranging from 1 gy to 200 gy.

In a further embodiment of the current invention, the method for generating and expanding T-MSC results in at least 10,000 T-MSC, at least 50,000 T-MSC, at least 100,000 T-MSC, at least 500,000 T-MSC, at least $1\times10^6$ T-MSC, at least $5\times10^6$ T-MSC, at least $1\times10^7$ T-MSC, at least $5\times10^7$ T-MSC, at least $1\times10^8$ T-MSC, at least $5\times10^8$ T-MSC, at least $1\times10^9$ T-MSC, at least $5\times10^9$ T-MSC, or at least $1\times10^{10}$ T-MSC. These methods result in cell solutions that may comprise between 10,000 and 10 billion T-MSC. In certain embodiments, at least about 90%, 91%, 92%, 93%, 94%, 95%, 96%, 97%, 98%, or 99% of the resulting human embryonic-mesenchymal stem cells express one or more hES-MSC differential markers. In certain embodiments, the marker is CD73, CD90 and CD105.

In one embodiment, the T-MSCs remarkably attenuate the disease score of the EAE mice, accompanied by decreased demyelination, T cell infiltration, and microglial responses. In addition, the T-MSCs have much stronger immunosuppressive activity in vivo and in vitro when compared to bone marrow derived MSCs (BM-MSC). Also provided herein are key proteins/molecules that are differentially expressed between T-MSC and BM-MSCs. Provided herein are methods of identifying T-MSCs with improved immunosuppressive activity by measuring the expression level of the protein/molecular markers. Also disclosed are methods of genetic modification to improve immunosuppressive activity of T-MSCs.

A further embodiment of the present invention is a solution comprising T-MSC comprising at least 10,000 T-MSC, at least 50,000 T-MSC, at least 100,000 T-MSC, at least 500,000 T-MSC, at least $1\times10^6$ T-MSC, at least $5\times10^6$ T-MSC, at least $1\times10^7$ T-MSC, at least $5\times10^7$ T-MSC, at least $1\times10^8$ T-MSC, at least $5\times10^8$ T-MSC, at least $1\times10^9$ T-MSC, at least $5\times10^9$ T-MSC, or at least $1\times10^{10}$ T-MSC.

In certain embodiments, the culture volume is from 2 ml for at least 10,000 cells, 10 ml for at least 100,000 cells, 100 ml for at least 1,000,000 cells, 1000 ml for at least 10,000,000 cells, and up to 4000 ml of media for $5\times10^8$ cells.

These solutions can be injected into a subject. These solutions can be frozen. These solutions can be used for the manufacture of a medicament for a disease that can be treated by the administration of T-MSC.

This invention also provides a method for producing a solution of T-MSC suitable for injection into a patient comprising the steps of isolating the solution of cells described in the preceding paragraph and placing the cells into solution suitable for injection into a patient. This invention also provides a method of producing a solution of T-MSC suitable for freezing comprising the steps of isolating the cells described in the preceding paragraph and placing into a solution suitable for freezing.

Yet another embodiment of the present invention is a T-MSC expressing one or more of cell marker proteins including CD73, CD90, CD105, CD13, CD29, CD54, CD44, CD146, CD166 or a combination thereof. In a further embodiment, the human embryonic-mesenchymal stem cell does not express or expresses low levels of one or more cell marker proteins including CD34, CD31, CD45 or a combination thereof. In a further embodiment, the human embryonic-mesenchymal stem cell does not express or expresses low levels of one or more pro-inflammatory proteins including MMP2, RAGE, IFNγR1, IFNγR2, IL-12, TNFα, IL-6, VCAM1 or a combination thereof. In certain embodiments, the human embryonic-mesenchymal stem cell expressed at least half of the level of the above markers as compared to bone marrow derived MSC.

A further embodiment of the present invention is a cell culture comprising T-MSC expressing one or more of cell marker proteins including CD73, CD90, CD105, CD13, CD29, CD54, CD144, CD146 and CD44. In a further embodiment, the T-MSC in the cell culture do not express or express low levels of one or more cell marker proteins including CD34, CD31 and CD45. In a further embodiment, the T-MSC in the cell culture do not express or express low levels of one or more pro-inflammatory proteins including MMP2, RAGE, IFNγR1, IFNγR2, IL-12, TNFα, IL-6, and VCAM1.

In certain embodiments, the cell culture comprises at least $1\times10^6$ T-MSC, at least $1\times10^7$ T-MSC at least $1\times10^8$ T-MSC, at least $1\times10^9$ T-MSC, or at least $1\times10^{10}$ T-MSC.

In further embodiments, at least about 90% of the T-MSC in the cell culture express the CD73 protein, at least more than 90% of the T-MSC express the CD73 protein, at least about 95% T-MSC express the CD73 protein, or more than 95% T-MSC express the CD73 protein. In further embodiments, at least about 96% of the T-MSC in the cell culture express the CD73 protein, at least more than 97% of the T-MSC express the CD73 protein, at least about 98% T-MSC express the CD73 protein, or more than 99% T-MSC express the CD73 protein.

In further embodiments, at least about 75%, 80%, 85%, 90%, 95%, 99% of the T-MSC in the cell culture express at least one cell marker protein selected from the group consisting of CD90, CD105, CD44, and CD29.

In further embodiments, at least about 80%, 85%, 90%, 95%, 99% of the T-MSC in the cell culture do not express or express low levels of at least one cell marker including CD34, CD31, and CD45.

In further embodiments, at least about 75%, 80%, 85%, 90%, 95%, 99% of the T-MSC in the cell culture do not express or express low levels of at least one pro-inflammatory protein including MMP2, RAGE, IFNγR1, IFNγR2, IL-12, TNFα, IL-6, and VCAM1. In certain embodiments, the T-MSC express high levels of CD24, TGFβ2 or both.

In certain embodiments of the T-MSC or cell cultures described herein, the cells are irradiated using gamma radiation.

Further embodiments of the present invention are pharmaceutical preparations comprising any one of the T-MSC or cell cultures described herein and pharmaceutically acceptable carriers.

Yet further embodiments of the present invention are cryopreserved preparations of any of the T-MSC or cell cultures described herein.

Provided herein are methods of treating or preventing a T cell related autoimmune disease in a subject in need thereof, comprising the steps of administering a therapeutically effective amount of solution, cell culture or pharmaceutical preparation comprising T-MSC as described in the preceding paragraphs, to the subject in need thereof. The T cell related autoimmune diseases include but are not limited to Crohn's disease, inflammatory bowel disease, graft versus host disease, systemic lupus erythematosus, and rheumatoid arthritis, T cell mediated delayed type hypersensitivity (Type IV hypersensitivity) i.e., Type 1 diabetes mellitus, MS, RA, Hashimoto's thyroiditis, Crohn's, contact dermatitis, Scleroderma, etc.

In certain embodiments, the subject is preferably a mammal or avian, and most preferably human. In certain embodiments, the solution, cell culture or pharmaceutical preparation comprises irradiated or non-irradiated T-MSC.

In certain embodiments, the method for treating or preventing disease includes combination therapy with one or more therapeutic agents for the treatment or prevention of disease.

In other certain embodiments, the present invention provides methods for treating or preventing multiple sclerosis disease in a subject in need thereof, comprising the steps of administering a therapeutically effective amount of solution, cell culture or pharmaceutical preparation comprising T-MSC as described in the preceding paragraphs, to the subject in need thereof. The multiple sclerosis can be relapsing/remitting multiple sclerosis, progressive/relapsing multiple sclerosis, primary multiple sclerosis, or secondary multiple sclerosis. The subject is preferably a mammal, and most preferably human. The solution, cell culture or pharmaceutical preparation can comprise irradiated or non-irradiated T-MSC.

The method can further comprise the administration of additional therapeutic agents to the subject, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine. In yet another embodiment, one or more of these therapeutic agents can be attached to the T-MSCs in order to cross the blood-brain and/or blood-spinal cord barrier, for delivery of the therapeutic agent to the central nervous system.

Provided herein is a method of delivering an agent through the blood-brain barrier and/or the blood-spinal cord barrier, the method comprising the steps of attaching or conjugating the agent to a T-MSC to form a complex; and administering the human embryonic-mesenchymal stem cell-agent complex to a subject in need thereof, wherein the T-MSC is capable of crossing the blood-brain barrier and/or the blood-spinal cord barrier and the agent is for the treatment, prevention or diagnosis of a disease or injury in the subject in need thereof. T-MSC may be in the form of a single cell, a cell culture, a solution or a pharmaceutical preparation. Agents would include, but are not limited to, drugs, proteins, DNA, RNA, and small molecules.

A further embodiment is a delivery system comprising a T-MSC and a conjugated or attached agent, for crossing the blood-brain barrier and/or the blood-spinal cord barrier.

The method described herein has a number of advantages. It is an object of the disclosed method to differentiate hESCs via an intermediate stage of trophoblasts, which is different from all the existing methods and leads to the following advantages.

Provided herein is a method of selecting clinical grade T-MSC for the treatment of autoimmune diseases, the T-MSC having the following characteristics: (i) contain >95% of cells expressing group-1 markers; (ii) contain >80% of cells expressing group 2 markers; (iii) contain <5% of cells expressing group-3 markers; (iv) express IL-10 and TGFβ; (v) contain <2% of cells expressing IL-6, IL-12 and TNFα; (vi) express high level of CXCR7, CXCL2, CXCL12 but a low level of HOXB2, HOXB3, HOXB5, HOXB7, HOXB9, HOXA5, HOXA9 and other HOX family genes (vii) contain <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

Provided herein is a method of modifying T-MSC to produce a population of modified MSC having the following characteristics: (i) contain >95% of cells expressing group-1 markers; (ii) contain >80% of cells expressing group 2 markers; (iii) contain <5% of cells expressing group-3 markers (iv) expressing IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

Provided herein are conditioned medium, concentrate of conditioned medium, cell lysate or other derivatives thereof that comprises one or more biomolecules secreted by the T-MSC as described.

Provided herein is a method of using T-MSC as described herein as feeder cells for bone marrow hematopoietic stem cell expansion and umbilical-cord hematopoietic stem cell expansion. In certain embodiments, the T-MSC suitable for the disclosed method express Stro3. In certain embodiments, T-MSC is co-cultured with bone marrow hematopoietic stem cells and/or umbilical-cord hematopoietic stem cells. In certain embodiments, the T-MSC are mesenchymal stromal cells. Provided herein is a co-culture of T-MSC as described herein and bone marrow hematopoietic stem cells. Provided herein is a co-culture of T-MSC as described herein and umbilical-cord hematopoietic stem cells.

Also disclosed are kits comprising T-MSC described herein. In certain embodiments, the kits comprise T-MSC and a cell delivery carrier.

In one aspect, provided herein is a method of suppressing or reducing an immune response comprising contacting a plurality of immune cells with a plurality of T-MSC for a time sufficient for the T-MSC to detectably suppress an immune response, wherein the T-MSC detectably suppress T cell proliferation and/or differentiation in a mixed lymphocyte reaction (MLR) assay. In another specific embodiment, the contacting is performed in vitro. In another specific embodiment, the contacting is performed in vivo. In a more specific embodiment, the in vivo contacting is performed in a mammalian subject, e.g., a human subject. In another more specific embodiment, the contacting comprises administering the T-MSC intravenously, intramuscularly, or into an organ in the subject (e.g., a pancreas).

Provided herein are methods of producing cell populations comprising T-MSC selected on the basis of their ability to modulate (e.g., suppress) an immune response. In one embodiment, for example, the invention provides a method of selecting a T-MSC population comprising (a) assaying a plurality of T-MSC in a mixed lymphocyte reaction (MLR) assay; and (b) selecting the plurality of T-MSC if the plurality of T-MSC detectably suppresses $CD4^+$ or $CD8^+$ T cell proliferation in an MLR (mixed lymphocyte reaction), wherein the T-MSC express CD73, CD90, CD105, CD13, CD29, CD54, CD 44. In one embodiment, the T-MSC do not express or express at low level CD34, CD31 and CD45. In one embodiment, the T-MSC do not express or express at low level MMP2, RAGE, IFNGR2, IL-12A, IL-6 and VCAM1.

Provided herein are methods to differentiate T-MSC into multiple other cell lineages including, but not limited to, adipocytes, myoblast cells, neural lineage cells, osteoblast cells, fibroblast, chondrocytes, and stromal cells.

Provided herein are methods for using T-MSC and its differentiated cellular products for tissue regeneration and/or tissue repair comprising administering T-MSC and/or T-MSC derived other cell lineages, in an amount sufficient to promote tissue regeneration including, but not limited to, joint regeneration, tendon regeneration, connective tissue regeneration, neural lineage cells regeneration, fat tissue regeneration, bone regeneration, skin regeneration, muscle regeneration, cartilage regeneration, smooth muscle regeneration, cardiac muscle regeneration, epithelia tissue regeneration, ligament regeneration, etc.

In specific embodiments, the T cells and the T-MSC are present in the MLR at a ratio of, e.g., about 20:1, 15:1, 10:1, 5:1, 2:2, 1:1, 1:2, 1:5, 1:10 or 1:20, preferably 10:1.

It is a further object of the disclosed method to efficiently generate large numbers of MSCs via a high yield process. The disclosed method can generate about 10-fold higher numbers of MSCs compared to the starting number of hESCs. There is very little cell loss when hESCs are differentiated through the trophoblast stage, whereas, other methods usually have over 90% loss of the starting cells during the initial differentiation step, resulting in much lower cell yields than the method disclosed herein.

It is an object of the disclosed method to provide a method that can produce MSCs in a relatively short time. The entire process disclosed herein can be completed in no more than 6-14 days, depending on the starting hES lines.

It is an object of the disclosed method to provide a method that is low in cost. The differentiation method described herein only requires a very small amount of culture medium, and the method only requires one cytokine-BMP4, which is used in the disclosed method at a low dose.

It is an object of the disclosed method to provide a method that is low in cost. The differentiation method described herein only requires a very small amount of culture medium, and the method only requires one cytokine-BMP4 and/or a TGFβ inhibitor (i.e., SB8431542, A83-01 or ALK5 inhibitor etc.).

It is an object of the disclosed method to provide a method that is high in yield. The differentiation method described herein can produce $1-5 \times 10^{10}$ T-MSC cells within 30 days from $1 \times 10^5$ of hESC, whereas other method can only produce up to $1 \times 10^8$ MSC cells within 30 days.

It is a further object of the disclosed method to provide MSCs having high immunosuppressive efficacy. The T-MSC have higher immunosuppressive potency than MSCs derived from bone marrow (BM) or other sources, the T-MSC have higher immunosuppressive potency than MSCs derived from hESCs via other methods.

In specific embodiments, the T-MSC suppress $CD4^+$ or $CD8^+$ T cell proliferation by at least 50%, 70%, 90%, or 95% in an MLR compared to an amount of T cell proliferation in the MLR in the absence of the T-MSC.

In another specific embodiment, any of the foregoing compositions comprises a matrix. In a more specific embodiment, the matrix is a three-dimensional scaffold. In another more specific embodiment, the matrix comprises collagen, gelatin, laminin, fibronectin, pectin, omithine, or vitronectin. In another more specific embodiment, the matrix is a biomaterial. In another more specific embodiment, the matrix comprises an extracellular membrane protein. In another more specific embodiment, the matrix comprises a synthetic compound. In another more specific embodiment, the matrix comprises a bioactive compound. In another more specific embodiment, the bioactive compound is a growth factor, cytokine, antibody, or organic molecule of less than 5,000 daltons.

The invention further provides cryopreserved stem cell populations, e.g., a cell population comprising T-MSC, wherein the cell population is immunomodulatory, which are described herein. For example, the invention provides a population of T-MSC that have been identified as detectably suppressing T cell proliferation and/or differentiation in a mixed lymphocyte reaction (MLR) assay, wherein the cells have been cryopreserved, and wherein the population is contained within a container.

In a specific embodiment of any of the foregoing cryopreserved populations, the container is a bag. In various specific embodiments, the population comprises about, at least, or at most $1 \times 10^6$ the stem cells, $5 \times 10^6$ the stem cells, $1 \times 10^7$ the stem cells, $5 \times 10^7$ the stem cells, $1 \times 10^8$ the stem cells, $5 \times 10^8$ the stem cells, $1 \times 10^9$ the stem cells, $5 \times 10^9$ the stem cells, or $1 \times 10^{10}$ the stem cells. In other specific embodiments of any of the foregoing cryopreserved populations, the stem cells have been passaged about, at least, or no more than 5 times, no more than 10 times, no more than 15 times, or no more than 20 times. In another specific embodiment of any of the foregoing cryopreserved populations, the stem cells have been expanded within the container.

4. BRIEF DESCRIPTION OF FIGURES

FIG. 1 (A-B). (A) Flow chart of the protocol for hESC differentiation into T-MSCs via a trophoblast and pre-T-MSC stage. Key bio-markers that are associated with each differentiation stage are indicated. (B) Comparison of various MSC generation protocols for MSC yield and quality: hESCs were differentiated in three protocols. 1) T-MSC: 3 days in the trophoblast differentiation medium followed by 8-10 days in a MSC growth medium. 2) SB-MSC: 3-10 days in SB431542-supplemented differentiation medium followed by 12 days in the MSC growth medium. 3) HB-MSC: hESC are differentiated into MSC through a hemangioblast intermediate stage, hESC were differentiated into hemangioblast in serum-free medium for 10-13 days followed by 12 days in the MSC growth medium. The total number of MSCs (millions of cells) in different cultures at day 10, 20 and 30 following the initiation of the differentiation procedures are shown. MSC purity was determined by FACS analysis of CD73+ cell ratio.

Figure 2:
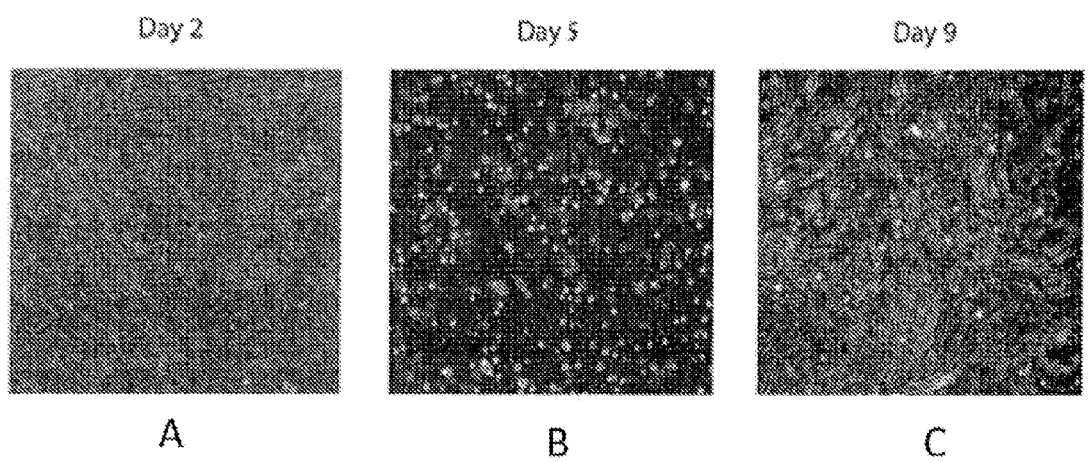

FIG. 2 (A-C). Morphological changes observed at various time points in cultures of hESCs which are in the process of differentiating to T-MSCs. (A) Day 2: trophoblasts; (B) Day 5: pre-MSCs (mesodermal cells); and (C) Day 9: MSCs.

Figure 3:
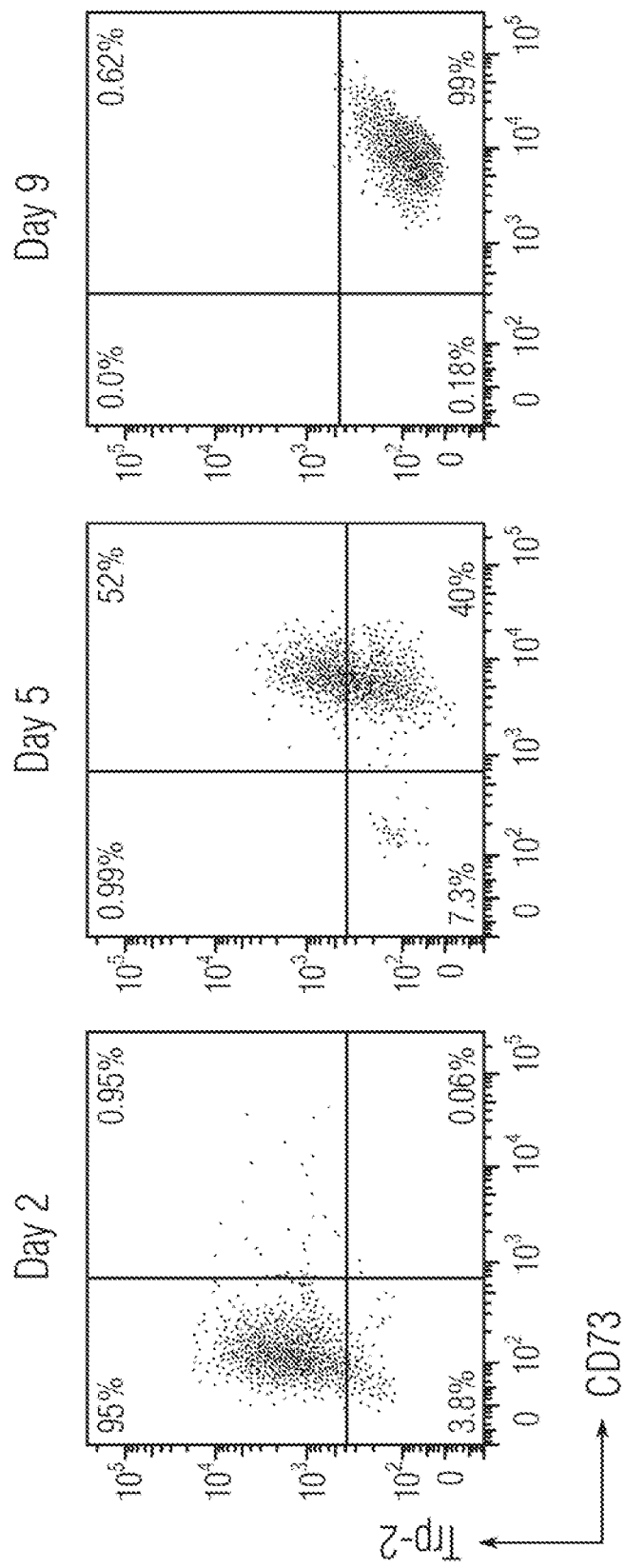

FIG. 3 (A-C). Analysis of the ratio of cells expressing the trophoblast marker Trop-2 (Trp-2) and MSC marker CD73 at various time points during the differentiation of hESC into T-MSC. (A) Day 2: trophoblasts; (B) Day 5: pre-MSCs (mesodermal cells); and (C) Day 9: MSCs.

Figure 4:
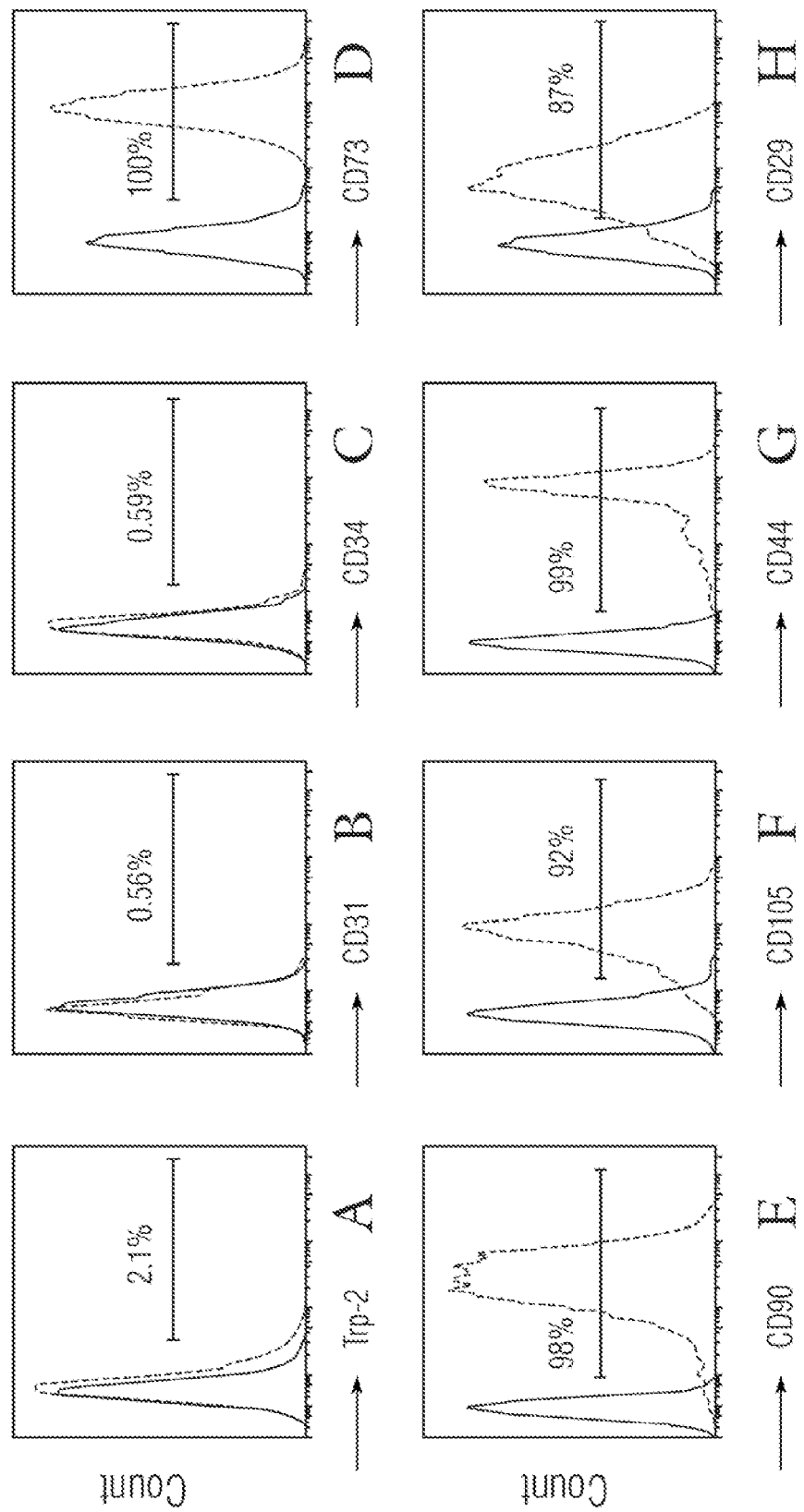

FIG. 4 (A-H). Surface marker expression profile of T-MSC after 11 days of differentiation. (A) Trp2 is a marker for trophoblasts, (B) CD31 is a marker for endothelial cells, and (C) CD34 is a marker for hematopoietic stem cells. (D-H) CD73, CD90, CD 105, CD44, CD29 are markers for MSCs.

Figure 5:
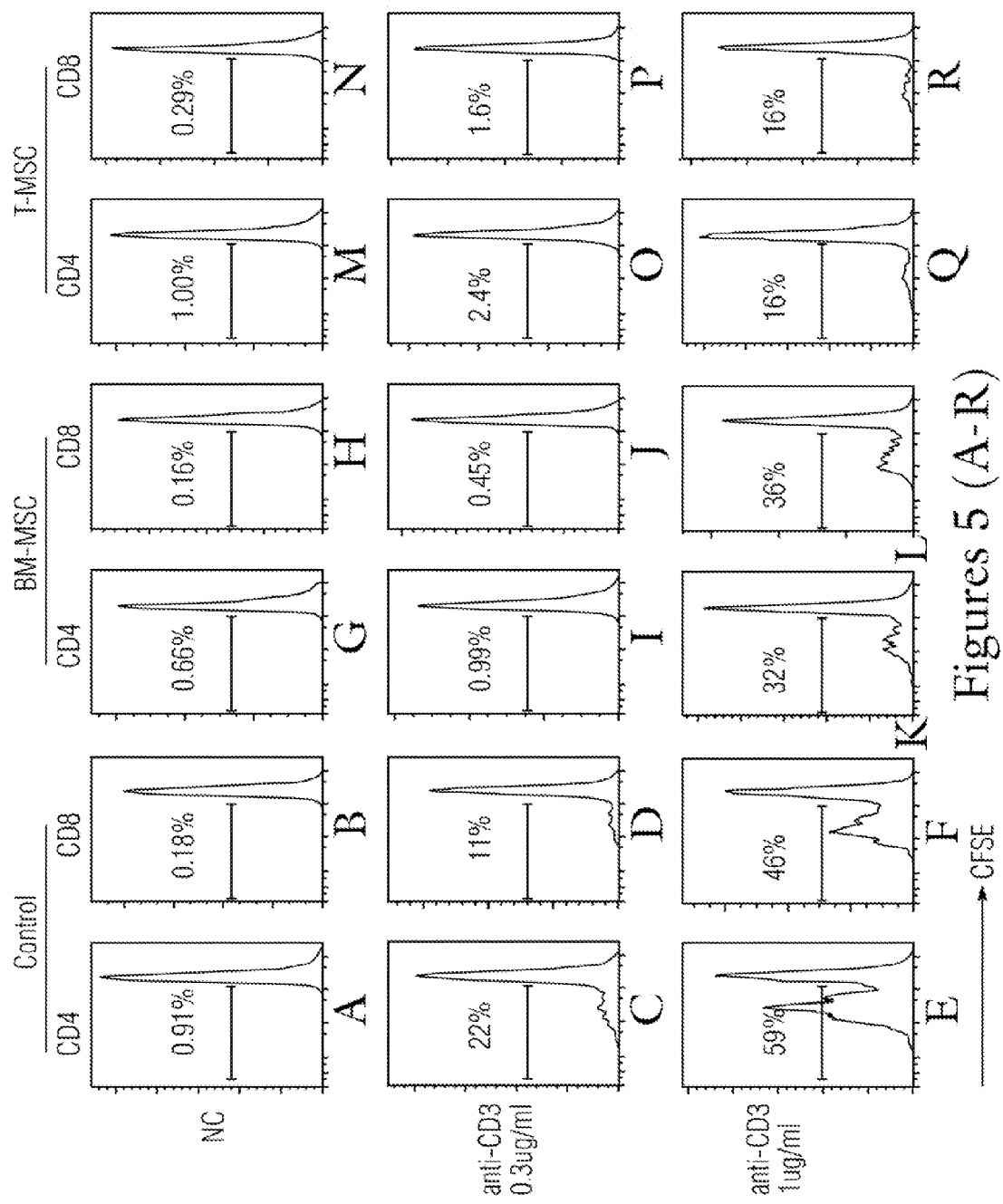

FIG. 5 (A-R). The in vitro immunosuppressive function of T-MSCs. BM-MSCs (G-L) or T-MSCs (M-R) were mixed with CFSE-labeled mouse lymphocytes at 10:1 ratio. The cells were stimulated with anti-CD3 antibody at 0.3 or 1 μg/ml together with 1 μg/ml of anti-CD28 antibody. Cell proliferation was indicated by CFSE dilution via FACS analysis. (A-F) T cells cultured without BM-MSC or T-MSC (labeled control) are shown.

Figure 6:
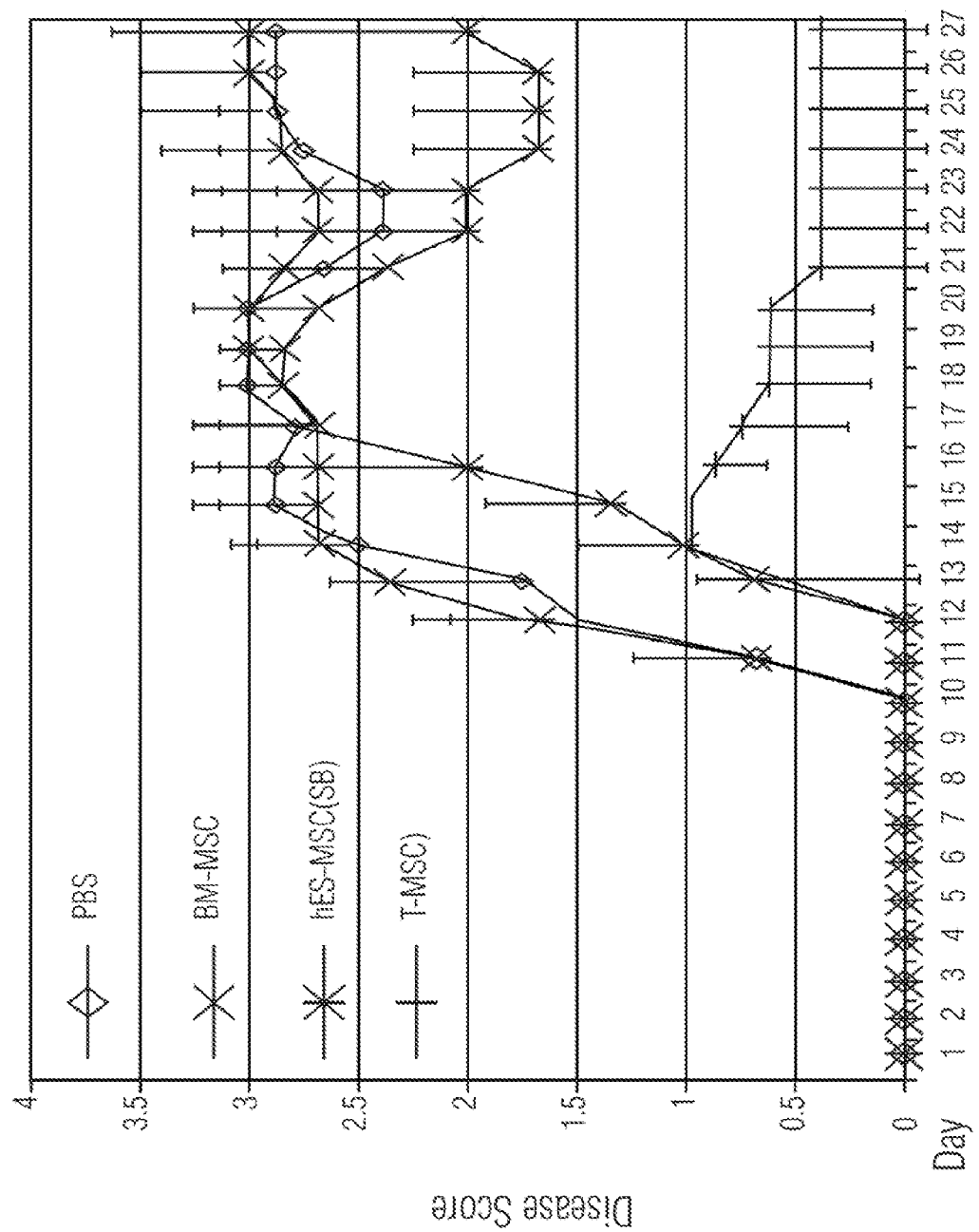

FIG. 6. T-MSC attenuate the disease score of an EAE mouse model: EAE was induced in C57BL/6 mice with MOG35-55 plus an adjuvant and pertussis toxin. T-MSC, BM-MSC or MSCs derived from hESCs using the SB431542 method (hES-MSC(SB)) were intraperitoneously injected into the mice, 6 days after the EAE induction. Disease score (from 0 being the no disease to 4 being the severe disease) was recorded for 27 days after the MSC injection.

Figure 7:
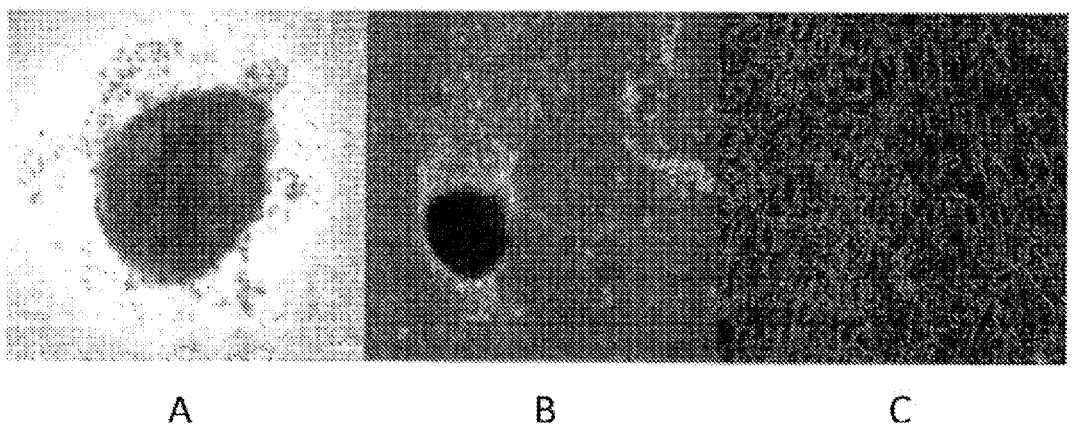

FIG. 7 (A-C). Determination of the multipotency of T-MSC to differentiate into: (A) osteocytes, (B) chondrocytes, and (C) adipocytes.

Figure 8:
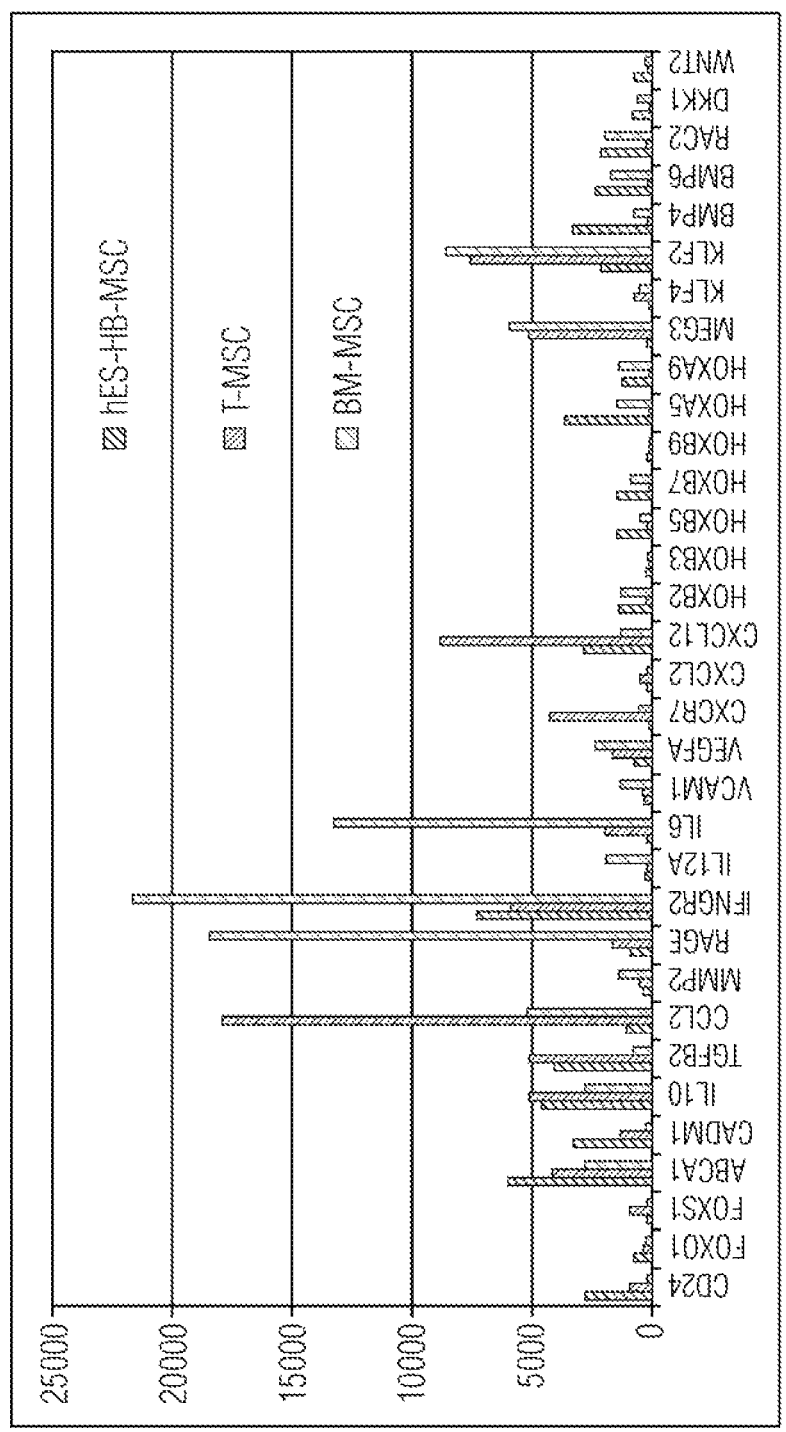

FIG. 8. Gene expression analysis of comparing hES-HB-MSC (hES hemangioblast derived MSC) with T-MSC (hES trophoblast derived MSC) and BM-MSC (adult bone marrow derived MSC). Gene expression was normalized and is shown as arbitrary expression units.

5. DETAILED DESCRIPTION

5.1 Definitions

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be the in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term hESC means human embryonic stem cells that encompass pluripotent stem cells produced from embryo, inner cell mass, blastomere or a cell line.

The term "hES-MSC" or hES-MSCs" or "human embryonic mesenchymal stem cells' or human embryonic stem cell derived mesenchymal stem cells" or "hES-MSC population" as used herein means mesenchymal-like stem cells, mesenchymal-like stromal cells, mesenchymal stem cells or mesenchymal stromal cells, derived from human embryonic stem cells or derived from induced pluripotent stem cells ("iPSCs") using any methods. hES-MSC as used herein includes individual cells, cell lines, batches, lots or populations of hES-MSC.

The term "T-MSC" refers to MSC or mesenchymal stem/stromal cells that are derived from human embryonic stem cells (hESC) or induced pluripotent stem cells (iPSC) through a trophoblast intermediate stage where cells express Trop-2 with trophoblast-like morphology. The term "hES-T-MSC" refers to T-MSC differentiated from hESC. The term "iPS-T-MSC" and "iT-MSC" refer to T-MSC differentiated from iPSC. The term "T-MSC" as used herein does not refer to a trophoblast. A cell is considered a "stem cell" if the cell retains at least one attribute of a stem cell, e.g., the ability to differentiate into at least one other type of cell, or the like. These cells can be described based upon numerous structural and functional properties including but not limited to, expression or lack of expression of one or more markers. T-MSCs, including both hES-T-MSC and iT-MSC, are multipotent and capable of differentiating to give rise to other cell types and cell lineages.

The term "hES-HB-MSC" and "HB-MSC" are mesenchymal stem cells that are derived from human pluripotent stem cells including hESC and iPSCs via hemangioblast or hemangiocolony forming middle step.

The term "clinical grade T-MSC" as used herein means T-MSC which contains characteristics that are suitable for use in clinical use for human, avian or other mammals. Clinical grade T-MSC as used herein includes individual cells, cell lines, batches, lots or populations of MSC.

The term "T-MSC population" as used herein means a population of T-MSC cells which contains cells that have characteristics that are suitable for use in treatment and cells that do not have characteristics that are suitable for use in treatment.

The term "T-MSC derived lineages" or T-MSC-DL as used herein means cells or cell lineages differentiated from T-MSC including, but not limited to, adipocytes, myoblast cells, neural lineage cells, osteoblast cells, fibroblast, chondrocytes, and stromal cells.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "subject" as used in this application means an animal with an immune system such as avians and mammals. Mammals include canines, felines, rodents, bovine, equines, porcines, ovines, and primates. Avians include, but are not limited to, fowls, songbirds, and raptors. Thus, the invention can be used in veterinary medicine, e.g., to treat companion animals, farm animals, laboratory animals in zoological parks, and animals in the wild. The invention is particularly desirable for human medical applications The term "in need thereof" would be a subject known or suspected of having or being at risk of developing a disease including but not limited to multiple sclerosis and other T cell related autoimmune diseases, or diseases related to the central nervous system or the blood-brain barrier or the blood-spinal cord barrier.

A subject in need of treatment would be one that has already developed the disease. A subject in need of prevention would be one with risk factors of the disease.

The term "agent" as used herein means a substance that produces or is capable of producing an effect and would include, but is not limited to, chemicals, pharmaceuticals, drugs, biologics, small molecules, antibodies, nucleic acids, peptides, and proteins.

As used herein, a stem cell is "positive" for a particular marker when that marker is detectable. For example, a T-MSC is positive for, e.g., CD73 because CD73 is detectable on T-MSC in an amount detectably greater than background (in comparison to, e.g., an isotype control). A cell is also positive for a marker when that marker can be used to distinguish the cell from at least one other cell type, or can be used to select or isolate the cell when present or expressed by the cell.

As used herein, "immunomodulation" and "immunomodulatory" mean causing, or having the capacity to cause, a detectable change in an immune response, and the ability to cause a detectable change in an immune response.

As used herein, "immunosuppression" and "immunosuppressive" mean causing, or having the capacity to cause, a detectable reduction in an immune response, and the ability to cause a detectable suppression of an immune response.

The present invention is based on the first discovery that mesenchymal stem cells MSCs can be differentiated from the hESC derived trophoblasts, and that the trophoblast-derived MSCs (T-MSC) can be used for tissue repair and immune regulation. These T-MSC produced from the disclosed methods all remarkably inhibited T cell proliferation and differentiation in vitro and attenuated the disease score in vivo, whereas bone marrow-derived MSC (BM-MSC) had no effect at all in vivo, although the BM-MSC may partially reduce T cell proliferation and differentiation in vitro. The T-MSC disclosed herein have surprisingly higher immunosuppressive activity compared to BM-MSC. The methods disclosed herein are highly efficient and can produce high number of T-MSC with low cost and high purity. The methods disclosed herein are highly reproducible with little batch-to-batch variations, and easily adaptable to meet clinical needs.

Thus, the present invention overcomes the problems described above by providing a method of generating mesenchymal stem cells (MSC) in vitro from human embryonic stem cells. The ability to generate the hES-T-MSC by the methods disclosed herein allows the production of cells that can be used in a variety of therapeutic applications, including the treatment and prevention of multiple sclerosis, and other autoimmune diseases. Additionally, the hES-MSC produced by the methods described herein have the ability to cross the brain-blood barrier (BBB) and the blood-spinal cord barrier (BSCB) allowing them to be used for a variety of therapeutic applications, including drug delivery. The methods of the invention provide further utility in that they enable the generation of large numbers of hES-T-MSC that can be used on a commercial scale.

5.2 Differentiation of Embryonic Stem Cells Through Trophoblast to Obtain T-MSC Disclosed herein is a method for generating and expanding mesenchymal-like stem cells (MSCs) from trophoblast derived from embryonic stem cells (hES). These resulting cells are designated T-MSC. These T-MSC can be isolated and/or purified.

MSC-like cells have been derived from human embryonic stem cells by various methods (Barbieri et al. (2005); Olivier et al. (2006); Sanchez et al. (2011); Brown et al. (2009)). However, all of these methods involve co-culturing and hand-picking procedures that limit yield and purity and result in varying quality of cells.

Although hESC express low levels of MHC antigens, it has been found that many cell types differentiated from hESC have increased expression of these antigens (Draper et al., 2002; Drukker et al., 2006; Drukker et al., 2002), thus, causing great concern for immunorejection of the differentiated cells if transplanted into patients. In contrast, MSC express low levels of costimulatory molecules and major MHC antigens, and have been used in allogeneic or xenograft models to treat autoimmune diseases (Gordon et al., 2008b; Grinnerno et al., 2004; Rafei et al., 2009a; Rafei et al., 2009b; Tse et al., 2003). T-MSC, like adult tissue-derived MSC, express low levels of the co-stimulatory molecules and MHC antigens, and do not require long-term engraftment to exert immunosuppressive effect, thus, there is no concern for immunorejection due to mismatch of MHC antigens between MSC and the recipient. One hESC line is sufficient to generate T-MSC at large scale, in an endless supply, and with easy quality control, suitable for industrial production as a potential therapy to treat patients with MS and other T cell-based autoimmune diseases.

Human trophoblast can be generated from human embryonic stem cells. Such embryonic stem cells include embryonic stem cells derived from or using, for example, blastocysts, plated ICMs, one or more blastomeres, or other portions of a pre-implantation-stage embryo or embryo-like structure, regardless of whether produced by fertilization, somatic cell nuclear transfer (SCNT), parthenogenesis, androgenesis, or other sexual or asexual means.

Additionally or alternatively, trophoblast can be generated from other embryo-derived cells. For example, trophoblast can be generated (without necessarily going through a step of embryonic stem cell derivation) from or using plated embryos, ICMs, blastocysts, one or more blastomeres, trophoblast stem cells, embryonic germ cells, or other portions of a pre-implantation-stage embryo or embryo-like structure, regardless of whether produced by fertilization, somatic cell nuclear transfer (SCNT), parthenogenesis, androgenesis, or other sexual or asexual means. Similarly, trophoblast can be generated using cells or cell lines partially differentiated from embryo-derived cells. For example, if a human embryonic stem cell line is used to produce cells that are more developmentally primitive than trophoblast, in terms of development potential and plasticity, such embryo-derived cells could then be used to generate trophoblast.

Additionally or alternatively, trophoblast can be generated from other pre-natal or peri-natal sources including, without limitation, umbilical cord, umbilical cord blood, amniotic fluid, amniotic stem cells, and placenta.

The human embryonic stem cells may be the starting material of this method. The embryonic stem cells may be cultured in any way known in the art, such as in the presence or absence of feeder cells.

In the examples set forth herein, eight hESC cell lines were used, H9 (derived from WiCell Research Institute) (Thomson et al. (1998), CT2 (derived from University of Connecticut Stem Cell Core (Lin et al. (2010)); and ES03-

Envy (Envy, a GFP-labeled line, derived at ES International) (Costa et al. (2005)), ESI-017, ESI-053, ESI-049, ESI-035, and ESI-051.

In the first step of this method to obtain T-MSC, human embryonic stem cells are grown in small clumps or single cells in serum-free media without bFGF. The cells are then re-plated and cultured with BMP4 (1-200 ng/ml) as the only cytokine for a short time (2-5 days) to obtain a highly homogenous population of trophoblasts as they express the typical trophoblast marker Trop2/TACSTD2 (Trp2). A TGFβ inhibitor (SB431542 (1-20 µM), A83-01 (0.2-5 µM) or ALK5 inhibitor (1-20 µM), etc.) can be used to increase the trophoblast forming efficiency. The cells will expand and differentiate into trophoblast cells in 2-5 days with trophoblast-like morphology, in certain embodiments, more than 90% of cells express Trop-2/TACSTD2 (Trp-2) (Xu et al., 2002). Trophoblasts may be isolated by size or purified with antibody, such as by immunoaffinity column chromatography.

In one embodiment, trophoblast cells are digested to form single cells with TrypLE, Trypsin or collagenase B. The single cells are re-suspended in a medium optimized for mesenchymal stem cell growth such as alpha-MEM containing 2-20% of fetal bovine serum (FBS) or human AB serum (ABHS), DMEM-high glucose containing 2-20% of FBS or ABHS, the FBS can be replaced with 5-20% of knock-out serum replacement (KOSR) or bovine serum albumin (BSA), or any other commercial available serum free MSC culture mediums. In certain embodiments, Serum, KOSR or BSA is added in a concentration of from about 5-20%. In certain embodiments, fetal bovine serum is preferred. In certain embodiments, cells are cultured at a density of about 10-1000 cells/cm². In certain embodiments, the cells are cultured in an environment that mimics the extracellular environment of tissues, such as gelatin, vitronectin, laminin, fibronectin, collagen I. In certain embodiments, the MSC culture medium comprises LIF (2-20 ng/ml), bFGF (2-100 ng/ml), or PDGF (1-50 ng/ml) to increase expansion efficiency.

After approximately 24 hours, a number of cells (50-90%) attached to the culture plate and approximately 2-3 days later, pre-T-MSC begin to differentiate from the trophoblasts, cells were elongated and form clear cell border. In certain embodiments, the pre-T-MSC express both CD73 and Trop-2. After 6-10 days, more than 80-90% cells trophoblasts are differentiated into mesenchymal-like small cell with spindle-like morphology, so called T-MSC here. T-MSC can also be identified by the expression of certain markers, such as CD73, CD90, CD105, CD13, CD29, CD54, CD44, CD146 and CD166 and by the absence or low expression of certain markers such as CD31, CD34, and CD45. In certain embodiments, T-MSC do not express HOX and HLA-G. In certain embodiments, T-MSC express high level of CXCR7, CXCL2, CXCL12 but low level of HOXB2, HOXB3, HOXB5, HOXB7, HOXB9, HOXA5, HOXA9 and other HOX family genes. T-MSC are also characterized as multipotent and able to differentiate into adipocytes, chondrocytes, osteoblast cells, neurons, myoblasts, stromal cells and fibroblasts.

Provided herein is an isolated cell population comprising a plurality of immunosuppressive T-MSC that expresses at least one of the following markers: CD73, CD90 and CD105.

In a further embodiment of the present invention, an additional step of irradiating the T-MSCs is performed. This irradiation can be accomplished with the use of any method known in the art that emits radiation including but not limited to gamma irradiation e.g., Cesium-137 gamma irradiation, or photon radiation using X-ray. The preferred amount of radiation to be administered is about between 5 and 20000 gy, more preferably about between 50 and 100 gy, and most preferably 80 gy.

In one embodiment, the method described herein is a novel process for deriving (also referred to herein as producing) T-MSC from hESCs. The method comprises the steps of:

a. Culturing a cell culture comprising human embryonic stem cells in serum-free medium in the present of at least one growth factor in an amount sufficient to induce the differentiation of the embryonic stem cells to differentiate into trophoblast; in an embodiment, the time period of the differentiation into trophoblast is about 2-5 days; in an embodiment, the medium comprises BMP4, with or without the presence of an TGFb inhibitor (i.e., SB431542, A83-01 or ALK5 inhibitor etc.) to increase the differentiation efficiency;

b. Adding at least one growth factor to the culture comprising the trophoblasts and continuing to culture in serum-free medium, wherein the growth factor is in an amount sufficient to expand the trophoblasts, in an embodiment, the medium comprises BMP4, (this step is optional);

c. Isolating the trophoblasts and re-plating the trophoblasts onto gelatin, laminin, fibronectin, vitronectin, collagen or Matrigel-coated plates and cultured in a serum-containing or serum-free media in an amount sufficient to differentiate the trophoblast into T-MSC through pre-T-MSC, in an embodiment, the isolated trophoblast is cultured for 6-10 days to produce the T-MSC, wherein at least about 90%, 95%, 96%, 97%, 98%, 99% of the resulting T-MSC express cell surface markers for adult MSCs, in an embodiment, the medium comprises LIF, bFGF, PDGF to increase expansion efficiency, wherein at least about 90%, 95%, 96%, 97%, 98%, 99% of the resulting T-MSC express cell surface markers for adult MSCs.

As shown in FIGS. 1 & 2, the disclosed method starts with dispersal of hESC colonies into small clumps or single cells. The cells are then re-plated and cultured with BMP4 as the only cytokine, and a TGFβ inhibitor for a short time (2-5 days) to obtain a highly homogenous population of trophoblasts as they express the typical trophoblast marker Trop-2/TACSTD2 (Trp-2) (Xu et al., 2002). The trophoblasts are then dissociated and re-plated onto a gelatin, laminin, fibronectin, vitronectin, collagen or matrigel-coated plate and cultured in a MSC growth medium for 4-10 days to generate spindle-like cells similar to the morphology of typical MSCs.

The method disclosed herein, unlike the other methods, does not require feeder cells, sorting or hand-picking of the cells. The initial trophoblast differentiation step is in a defined, serum-free medium without bFGF. The entire protocol only requires two steps of differentiation in a total of 6-14 days to generate T-MSC at high purity and high yield (FIG. 1). This is the shortest differentiation protocol ever reported for MSC derivation from hESC. The yield and purity of the T-MSC are very high compared to those achieved using previously reported methods. Within 30 days, T-MSC at $5 \times 10^5$ fold the number of the original hESCs can be obtained and with a high percentage of CD73+ cells, a typical marker for MSCs, whereas the other methods can only yield less than 100 fold the original hESC number with a low percentage of CD73+ cells. The derivation of the T-MSC includes an intermediate stage of CD73/Trp-2 double positive cells, hereafter named pre-T-MSC. After 2-3 days of the BMP4 plus a TGFβ inhibitor treatment, the cells first express Trp-2 at a high percentage and demonstrate a homogenous morphology of trophoblasts (FIGS. 2 & 3). After 5-6 days, the cells express both Trp-2 and CD73; after 6-14 days, the cells no longer express Trp2 but express the typical MSC surface markers at high percentages including CD73 (>98%), CD90 (>95%), CD105 (>90%), CD44 (>95%), CD29 (>80%); and the cells are negative for the endothelial marker CD31 and hematopoiesis markers CD34 and CD45 (FIGS. 3 & 4).

T-MSC produced by the method disclosed herein are capable of differentiating to downstream osteogenesis, chondrogenesis and adipogenesis lineages (FIG. 7). Thus, the T-MSC are phenotypically and functionally similar to MSCs derived from the bone marrow (BM) and other sources.

5.3 Human Embryonic Stem Cell-Derived Mesenchymal Stem Cells

Bone marrow-derived MSCs (BM-MSCs) have long been used to treat autoimmune disease in many animal models and clinical trials, however the efficacy of immunosuppression is not consistent with some reports showing BM-MSCs are unable to efficiently treat certain autoimmune diseases (Tyndall, 2011). Data is provided herein comparing the ability of BM-MSCs and T-MSC for their inhibition of T cell proliferation following T cell receptor stimulation. As shown in FIG. 7, BM-MSCs can inhibit proliferation of both CD4 and CD8 T cells induced by anti-CD3 antibody at a low dose (0.3 ug/ml), which is comparable to T-MSC. However, when the anti-CD3 antibody concentration increased to 1 ug/ml, BM-MSCs have less potency in suppressing proliferation of both CD4 and CD8 T cells than T-MSC. CFSE dilution assay was used here to evaluate the T cell proliferation: an increased percentage of T cells with decreased CFSE signal indicates an accelerated proliferation. As shown in FIG. 5, when anti-CD3 antibody increased to 1 ug/ml, there were 59% of CD4 and 46% of CD8 T cells detected with decreased CFSE signal. T-MSC significantly decreased both the CD4 and CD8 T cells to 16%, whereas BM-MSCs only decreased CD4 and CD8 T cells to 32% and 36%, respectively.

Consistent with the in vitro immunosuppressive activity of the T-MSC, T-MSC produced by the method disclosed herein were shown to be effective to treat experimental autoimmune encephalomyelitis (EAE), a mouse model of multiple sclerosis. As shown in FIG. 6, when T-MSC were injected 6 days post the EAE induction, the disease score of the EAE mice significantly declined, compared to vehicle injection controls.

In a further feature of cells produced by the disclosed methods, T-MSC also demonstrated much stronger immunosuppressive effect than BM-MSCs and hES-MSCs derived through SB431542 treatment (Chen et al., 2012) (FIG. 6). In several repeated experiments, BM-MSCs consistently failed to attenuate the disease score of EAE mice. Thus, the replacement of BM-MSCs with T-MSC produced by the disclosed method for use in clinical applications would remove the need for risky, invasive procedures for bone marrow aspiration, reduce the time for waiting for BM donations, reduce the cost, and reduce batch to batch variations for preparing BM-MSCs on a per-patient basis.

In summary, disclosed herein is a highly efficient method to generate mesenchymal-like cells or MSCs from hESCs through an intermediate trophoblast stage, and the use of the T-MSC to treat autoimmune disease. Microarray analysis suggested that the T-MSC had a gene expression profile not identical to that of BM-MSCs (data not shown), although both can differentiate into the same downstream cell lineages (FIG. 7). In addition, the T-MSC have stronger immunosuppressive ability both in vitro and in vivo than BM-MSCs.

The available data suggest that T-MSC produced by the disclosed method are different from traditional, adult-derived MSCs. Due to their strong inhibition of T cell proliferation, T-MSC may be used to treat multiple sclerosis with much higher efficacy than BM-MSCs. To address potential safety concerns, T-MSC were injected into immunodeficient SCID-beige mice. No tumor or teratoma formation was observed in the mice.

The T-MSC of the present invention are unique and have a variety of therapeutic and other uses. Thus, the present invention includes various preparations, including pharmaceutical preparations, and compositions comprising T-MSC.

The term "T-MSC" refers to MSC or mesenchymal stem/stromal cells that are derived from human embryonic stem cells (hESC) or induced pluripotent stem cells (iPSC) through a trophoblast intermediate stage where cells express Trop-2 with trophoblast-like morphology. The term "hES-T-MSC" refers to T-MSC differentiated from hESC. The term "iPS-T-MSC" and "iT-MSC" refer to T-MSC differentiated from iPSC. The term "T-MSC" as used herein does not refer to a trophoblast. A cell is considered a "stem cell" if the cell retains at least one attribute of a stem cell, e.g., the ability to differentiate into at least one other type of cell, or the like. These cells can be described based upon numerous structural and functional properties including but not limited to, expression or lack of expression of one or more markers. Specifically, T-MSC are characterized by small cell bodies with a fibroblast morphology. T-MSCs, including both hES-T-MSC and iT-MSC, are multipotent and capable of differentiating to give rise to other cell types and cell lineages. The term "T-MSC-DL" refers to all the cell types and cell lineages differentiated from T-MSC.

The differentiation method described herein can achieve the differentiation of MSC from iPS cells within 6-14 days, the shortest time ever reported. Thus, these iT-MSC can be used for patient specific iPS based therapy under emergency conditions which requires the generation of MSC in very short time, such as acute heart infarction, acute heart failure, acute spinal cord injury, acute radiation/burning treatments, etc.

T-MSC can be identified or characterized by the expression or lack of expression as assessed on the level of DNA, RNA or protein, of one or more cell markers. T-MSC can be identified as expressing cell surface marker CD73, or expressing at least one or more of the following cell surface markers: CD90, CD105, CD13, CD29, CD54, CD44, CD146 or CD166 or not expressing or expressing at a low level at least one of the following cell surface markers: CD34, CD31, or CD45.

Alternatively or additionally, T-MSC can be identified or characterized based upon their low level of expression of one or more pro-inflammatory proteins, MMP2, RAGE, IFNGR2, TNFα, IL-12A, IL-6, and VCAM1. This profile of gene expression is in contrast to bone marrow derived mesenchymal stem cells. In particular, IL-6 was expressed much higher in BM-MSCs than in T-MSC. IL-6 is a pleiotropic cytokine involved in crosstalk between hematopoietic/immune cells and stromal cells, including the onset and resolution of inflammation.

The T-MSC can also be characterized in their ability to inhibit T cell proliferation after stimulation in vitro. This characteristic is in contrast to BM-MSCs which do not inhibit T cell proliferation after stimulation in vitro.

Thus, the T-MSC described herein have at least one of the following characteristics: (1) differentiate into adipocytes, chondrocytes, osteoblast cells, neurons, myoblasts, stromal cells and fibroblasts; (2) have a fibroblast-like morphology; (3) express CD73, CD90, CD105, CD13, CD29, CD54, CD44, CD146 and/or CD166; (4) express at low levels or do not express CD34, CD31, and/or CD45; (5) express at low levels or do not express MMP2, RAGE, IFNγR1, IFNγR2, IL-12, TNFα, IL-6, and/or VCAM1, particularly IL-6; (6) express MHC antigen HLA-G and/or HLA-ABC and express at low levels or do not express HLA-DR and/or CD80; and (7) inhibit T cell proliferation after stimulation in vitro. In certain embodiments, the T-MSCs have at least two, at least three, at least four, at least five, at least six, or all seven characteristics.

In certain embodiments, T-MSC is distinguishable with previously reported HB-MSC, T-MSC express at least one fold higher level of CXCR7, CXCL2 and/or CXCL12 than HB-MSC, but at least half of the level of HOXB2, HOXB3, HOXB5, HOXB7, HOXB9, HOXA5, HOXA9 and other HOX family genes compared to HB-MSC.

Additionally, the T-MSC have the unique ability to cross the blood-brain barrier (BBB) and the blood-spinal cord barrier (BSCB), making them uniquely suited for therapeutic and diagnostic applications. The T-MSC of the current invention have the ability to migrate in and out of the vessels of the spinal cord, across the BSCB, to fulfill functions in the CNS, including but not limited to the delivery of therapeutic and diagnostic agents. This is in contrast to BM-MSCs which do not have this ability.

Another embodiment of the present invention is a T-MSC that is irradiated. This embodiment would include T-MSC with at least one of the following characteristics listed above, having at least two, at least three, at least four, at least five, at least six, or all seven characteristics that have been subject to irradiation.

In another embodiment, the cell culture comprises T-MSC. In certain embodiments, the T-MSC differentiate into adipocytes, chondrocytes, osteoblast cells, neurons, myoblasts, stromal cells and fibroblasts. In certain embodiments, the T-MSC cells express CD73, CD90, CD105, CD13, CD29, CD54, CD44, CD146, and/or CD166. In certain embodiments, the cells express at low levels or do not express CD34, CD31, and/or CD45. In certain other embodiments, the cells express at low levels or do not express MMP2, RAGE, IFNγR1, IFNγR2, IL-12, TNFα, IL-6, and/or VCAM1, especially IL-6. In certain other embodiments, the cells express MHC antigen HLA-G and/or HLA-ABC and express at low levels or do not express HLA-DR and/or CD80. In certain other embodiments, the cells inhibit T cell proliferation after stimulation in vitro. In certain embodiments, the cells can cross the blood-brain barrier and the blood-spinal cord barrier. In certain embodiments, the cells have been irradiated.

In another aspect, disclosed herein a pharmaceutical preparation comprising T-MSC. In certain embodiments, the T-MSC can differentiate into adipocytes, chondrocytes, osteoblast cells, neurons, myoblasts, stromal cells and fibroblasts. In certain embodiments, the cells express CD73, CD90, CD105, CD13, CD29, CD54, CD44, CD146 and/or CD166. In certain embodiments, the cells express at low levels or do not express CD34, CD31, and/or CD45. In certain other embodiments, the cells express at low levels or do not express MMP2, RAGE, IFNγR1, IFNγR2, TNFα, IL-12, IL-6, and/or VCAM1, especially IL-6. In certain other embodiments, the cells express MHC antigen HLA-G and/or HLA-ABC and express at low levels or do not express HLA-DR and/or CD80. In certain other embodiments, the cells inhibit T cell proliferation after stimulation in vitro. In certain embodiments, the cells can cross the blood-brain barrier and the blood-spinal cord barrier. In certain embodiments, the cells have been irradiated. The pharmaceutical preparation can be prepared using any pharmaceutically acceptable carrier or excipient.

In certain embodiments, the composition or pharmaceutical preparation comprises at least at least 10,000 T-MSC, at least 50,000 T-MSC, at least 100,000 T-MSC, at least 500,000 T-MSC, at least $1\times10^5$ T-MSC, at least $5\times10^6$ T-MSC, at least $1\times10^7$ T-MSC, at least $5\times10^7$ T-MSC, at least $1\times10^8$ T-MSC, at least $5\times10^8$ T-MSC, at least $1\times10^9$ T-MSC, at least $5\times10^9$ T-MSC, or at least $1\times10^{10}$ T-MSC.

Provided herein are pluralities of T-MSC that comprise T-MSC obtained and isolated directly from a human embryonic stem cell line that have been cultured and passaged at least 1, 2, 3, 4, 5, 6, 7, 8, 9, 10, 12, 14, 16, 18, 20, 25, 30 or more times, or a combination thereof.

In certain embodiments, provided herein is a cryopreserved preparation of T-MSC or cells partially or terminally differentiated therefrom.

In certain embodiments, provided herein is a therapeutic use of T-MSC, or compositions or preparations of T-MSC, including irradiated T-MSC. Such cells and preparations can be used in the treatment of any of the conditions or diseases as described, as well as in a delivery system for agents across the blood-brain barrier and the blood-spinal cord barrier.

In certain embodiments, the invention provides a cryopreserved preparation of trophoblasts, pre-T-MSC, or T-MSC cells partially or terminally differentiated therefrom.

In certain embodiments, the invention provides the therapeutic use of T-MSCs, or compositions or preparations of T-MSCs, including irradiated T-MSCs. Such cells and preparations can be used in the treatment of any of the conditions or diseases detailed throughout the specification, as well as in a delivery system for agents across the blood-brain barrier and the blood-spinal cord barrier.

5.4 Selecting and Producing T-MSC Populations

Provided herein is a method of identifying highly immunosuppressive T-MSC by identifying a biomarker profile of the highly immunosuppressive T-MSC that are clinical grade for use in therapy. In certain embodiments, the clinical grade T-MSC have the following characteristics: (i) contain >95% of cells expressing group-1 markers; (ii) contain >80% of cells expressing group 2 markers; (iii) contain <5% of cells expressing group-3 markers (iv) express IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

In certain embodiments, the method comprises measuring the differential expression of markers that encode anti-inflammatory factors ("AIF") and pro-inflammatory factors ("PIF"). In certain embodiments, the AIF is IL-10, TGFβ2. In certain embodiments, the PIF is up regulated. In certain embodiments, T-MSC express at least 1.5 fold of the above markers as compared to BM-MSC. In certain embodiments, the PIF is IL-6, 11-12, TNFα, CCL2, VCAM1, RAGE, MMP2. In certain embodiments, the PIF is down regulated. In certain embodiments, T-MSC express at least half of the above markers as compared to BM-MSC In another embodiment, highly immunosuppressive T-MSC has a lower ratio of IL-6$^+$ cells as compared to BM-MSC. In certain embodiments, highly immunosuppressive T-MSC have less than 5%, 4%, 3%, 2%, or 1% of IL-6 positive cells. In certain embodiments, T-MSC express low levels of IL12, TNFα, RAGE and other PIF. In certain embodiments, T-MSC may express high levels of TGFβ2 and IL-10. In certain embodiments, the expression of markers is compared to expression in BM-MSC.

Provided herein is a qualification procedure for clinical grade T-MSC population. Expression of specific markers is measured in a population of T-MSC to determine whether they are suitable for therapeutic use. The markers include, for example, (1) MSC-specific markers (set 1): CD73, CD90, CD105, CD166, and CD44, (2) MSC-specific markers (set 2): CD13, CD29, CD54, CD49E, SCA-1, and STRO-1, (3) hematopoietic stem/progenitor markers: CD45 and CD34, and endothelial cell marker CD31, (4) immunogenic markers: HLA-ABC, HLA-G, CD80, and CD86, (5) cytokines: IL-10, TGFβ, IL-6, and IL-12, and (6) pluripotency markers: OCT4, NANOG, TRA-1-60, and SSEA-4. In certain embodiments, T-MSC population contains more than 95%, 96%, 97%, 98%, or 99% of cells that express at least one group 1 markers. In certain embodiments, T-MSC population contains more than 80%, 85%, 90%, 95%, or 99% of cells that express at least one group 2 markers. In certain embodiments, T-MSC population contains less than 0.1%, 0.08%, 0.05%, 0.03%, 0.02%, or 0.01% of cells that express at least one group 3 marker. In certain embodiments, T-MSC population contains more than 80%, 85%, 90%, 95%, or 99% of cells that express IL-10 and/or TGFβ. In certain embodiments, T-MSC population contains less than 5%, 4%, 3%, 2%, 1% of cells that express IL-6 and/or IL-12. In certain embodiments, T-MSC population contains less 0.001% of cells that express at least one group 6 marker. The clinical-grade T-MSC is compared with the preclinical-grade T-MSC as a positive control. In certain embodiments, the T-MSC is characterized through multi-color flow cytometry analyses and/or immunofluorescence. In certain embodiments, T-MSC population express CCL2, CCL3, CCL4, CCL5, IL-1, IL-2, IL-4, IL-6, IL-8, IL-10, IL-17, TNFα, TGFβ, IFNγ, GM-CSF, G-CSF, bFGF, CXCL5, VEGF, TPO or a combination thereof. In certain embodiments, the T-MSC population will also be analyzed for (1) presence of exogenous materials such as endotoxin and residual cytokines/growth factors, and/or (2) genomic abnormalities (via karyotyping and whole-genome sequencing).

Provided herein is another qualification procedure for clinical grade T-MSC population. T-MSC with better regeneration potential and immunosuppressive function may express a lower level of CD9, where CD9 expression level of Passage 1-2 T-MSC will be recorded as basal level, if after certain passages and procedures, the CD9 expression level increases by 2 fold, the cells will be stopped for passaging.

Methods for determining the expression profile of the T-MSC are known in the art, including but not limited to, flow cytometry, multiplex microarray, RT-PCT, Northern blot and Western blot. In certain embodiments, the expression profile of the MSC are determined by cytometric bead array based multiplex cytokine analysis, luminex system based multiplex cytokine analysis, microarray RNA-seq, quantitative RT-PCR, Elispot Elisa, Elisa cytokine array, flow cytometry luciferase reporter system, fluorescence reporter system, histology staining, and immunofluorescence staining.

5.4.1 Methods of Detecting Nucleic Acid Biomarkers

In specific embodiments, biomarkers in a biomarker profile are nucleic acids. Such biomarkers and corresponding features of the biomarker profile may be generated, for example, by detecting the expression product (e.g., a polynucleotide or polypeptide) of one or more markers. In a specific embodiment, the biomarkers and corresponding features in a biomarker profile are obtained by detecting and/or analyzing one or more nucleic acids expressed from a marker disclosed herein using any method well known to those skilled in the art including, but not limited to, hybridization, microarray analysis, RT-PCR, nuclease protection assays and Northern blot analysis.

In certain embodiments, nucleic acids detected and/or analyzed by the methods and compositions of the invention include RNA molecules such as, for example, expressed RNA molecules which include messenger RNA (mRNA) molecules, mRNA spliced variants as well as regulatory RNA, cRNA molecules (e.g., RNA molecules prepared from cDNA molecules that are transcribed in vitro) and discriminating fragments thereof.

In specific embodiments, the nucleic acids are prepared in vitro from nucleic acids present in, or isolated or partially isolated from a cell culture, which are well known in the art, and are described generally, e.g., in Sambrook et al., 2001, Molecular Cloning: A Laboratory Manual. 3rd ed., Cold Spring Harbor Laboratory Press (Cold Spring Harbor, N.Y.), which is hereby incorporated by reference in its entirety.

5.4.1.1 Nucleic Acid Arrays

In certain embodiments, nucleic acid arrays are employed to generate features of biomarkers in a biomarker profile by detecting the expression of any one or more of the markers described herein. In one embodiment of the invention, a microarray such as a cDNA microarray is used to determine feature values of biomarkers in a biomarker profile. Exemplary methods for cDNA microarray analysis are described below, and in the examples.

In certain embodiments, the feature values for biomarkers in a biomarker profile are obtained by hybridizing to the array detectably labeled nucleic acids representing or corresponding to the nucleic acid sequences in mRNA transcripts present in a biological sample (e.g., fluorescently labeled cDNA synthesized from the sample) to a microarray comprising one or more probe spots.

Nucleic acid arrays, for example, microarrays, can be made in a number of ways, of which several are described herein below. Preferably, the arrays are reproducible, allowing multiple copies of a given array to be produced and results from the microarrays compared with each other. Preferably, the arrays are made from materials that are stable under binding (e.g., nucleic acid hybridization) conditions. Those skilled in the art will know of suitable supports, substrates or carriers for hybridizing test probes to probe spots on an array, or will be able to ascertain the same by use of routine experimentation.

Arrays, for example, microarrays, used can include one or more test probes. In some embodiments, each such test probe comprises a nucleic acid sequence that is complementary to a subsequence of RNA or DNA to be detected. Each probe typically has a different nucleic acid sequence, and the position of each probe on the solid surface of the array is usually known or can be determined. Arrays useful in accordance with the invention can include, for example, oligonucleotide microarrays, cDNA based arrays, SNP arrays, spliced variant arrays and any other array able to provide a qualitative, quantitative or semi-quantitative measurement of expression of a marker described herein. Some types of microarrays are addressable arrays. More specifically, some microarrays are positionally addressable arrays. In some embodiments, each probe of the array is located at a known, predetermined position on the solid support so that the identity (e.g., the sequence) of each probe can be determined from its position on the array (e.g., on the support or surface). In some embodiments, the arrays are ordered arrays. Microarrays are generally described in Draghici, 2003, Data Analysis Tools for DNA Microarrays, Chapman & Hall/CRC, which is hereby incorporated by reference in its entirety.

5.4.1.2 RT-PCR

In certain embodiments, to determine the feature values of biomarkers in a biomarker profile of level of expression of one or more of the markers described herein, the feature values are measured by amplifying RNA from a sample using reverse transcription (RT) in combination with the polymerase chain reaction (PCR). In accordance with this embodiment, the reverse transcription may be quantitative or semi-quantitative. The RT-PCR methods taught herein may be used in conjunction with the microarray methods described above. For example, a bulk PCR reaction may be performed, and the PCR products may be resolved and used as probe spots on a microarray.

Total RNA, or mRNA is used as a template and a primer specific to the transcribed portion of the marker(s) is used to initiate reverse transcription. Methods of reverse transcribing RNA into cDNA are well known and described in Sambrook et al., 2001, supra. Primer design can be accomplished based on known nucleotide sequences that have been published or available from any publicly available sequence database such as GenBank. For example, primers may be designed for any of the markers described herein. Further, primer design may be accomplished by utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts. The method of PCR is well known in the art. PCR, is performed, for example, as described in Mullis and Faloona, 1987, Methods Enzymol. 155:335, which is hereby incorporated by reference in its entirety.

PCR can be performed using template DNA or cDNA (at least 10 fg; more usefully, 1-1000 ng) and at least 25 pmol of oligonucleotide primers. A typical reaction mixture includes: 2 µl of DNA, 25 pmol of oligonucleotide primer, 2.5 µl of 10 M PCR buffer 1 (Perkin-Elmer, Foster City, Calif.), 0.4 µl of 1.25 M dNTP, 0.15 µl (or 2.5 units) of Taq DNA polymerase (Perkin Elmer, Foster City, Calif.) and deionized water to a total volume of 25 µl. Mineral oil is overlaid and the PCR is performed using a programmable thermal cycler.

Quantitative RT-PCR ("QRT-PCR"), which is quantitative in nature, can also be performed to provide a quantitative measure of marker expression levels. In QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.) or as provided by Applied Biosystems (Foster City, Calif.) is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions are performed in 96-well plates so that samples derived from many individuals are processed and measured simultaneously. The Taqman system has the additional advantage of not requiring gel electrophoresis and allows for quantification when used with a standard curve.

A second technique useful for detecting PCR products quantitatively is to use an intercalating dye such as the commercially available QuantiTect SYBR Green PCR (Qiagen, Valencia Calif.). RT-PCR is performed using SYBR green as a fluorescent label which is incorporated into the PCR product during the PCR stage and produces a fluorescence proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol). Additionally, other systems to quantitatively measure mRNA expression products are known, including Molecular Beacons®, which uses a probe having a fluorescent molecule and a quencher molecule, the probe capable of forming a hairpin structure such that when in the hairpin form, the fluorescence molecule is quenched, and when hybridized the fluorescence increases giving a quantitative measurement of gene expression.

5.4.1.3 Northern Blot Assays

Any hybridization technique known to those of skill in the art can be used to generate feature values for biomarkers in a biomarker profile. In other particular embodiments, feature values for biomarkers in a biomarker profile can be obtained by Northern blot analysis (to detect and quantify specific RNA molecules. A standard Northern blot assay can be used to ascertain an RNA transcript size, identify alternatively spliced RNA transcripts, and the relative amounts of one or more genes described herein (in particular, mRNA) in a sample, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, cross-linked and hybridized with a labeled probe. Non-isotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

5.4.2 Methods of Detecting Proteins

In specific embodiments of the invention, feature values of biomarkers in a biomarker profile can be obtained by detecting proteins, for example, by detecting the expression product (e.g., a nucleic acid or protein) of one or more markers described herein, or post-translationally modified, or otherwise modified, or processed forms of such proteins. In a specific embodiment, a biomarker profile is generated by detecting and/or analyzing one or more proteins and/or discriminating fragments thereof expressed from a marker disclosed herein using any method known to those skilled in the art for detecting proteins including, but not limited to protein microarray analysis, immunohistochemistry and mass spectrometry.

Standard techniques may be utilized for determining the amount of the protein or proteins of interest present in a cell culture. For example, standard techniques can be employed using, e.g., immunoassays such as, for example, Western blot, immunoprecipitation followed by sodium dodecyl sulfate polyacrylamide gel electrophoresis, (SDS-PAGE), immunocytochemistry, and the like to determine the amount of protein or proteins of interest present in a sample. One exemplary agent for detecting a protein of interest is an antibody capable of specifically binding to a protein of interest, preferably an antibody detectably labeled, either directly or indirectly.

For such detection methods, if desired a protein from the cell culture to be analyzed can easily be isolated using techniques which are well known to those of skill in the art.

Protein isolation methods can, for example, be such as those described in Harlow and Lane, 1988, Antibodies: A Laboratory Manual, Cold Spring Harbor Laboratory Press (Cold Spring Harbor, N.Y.), which is hereby incorporated by reference in its entirety.

In certain embodiments, methods of detection of the protein or proteins of interest involve their detection via interaction with a protein-specific antibody. For example, antibodies directed to a protein of interest. Antibodies can be generated utilizing standard techniques well known to those of skill in the art. In specific embodiments, antibodies can be polyclonal, or more preferably, monoclonal. An intact antibody, or an antibody fragment (e.g., scFv, Fab or F(ab')$_2$) can, for example, be used.

For example, antibodies, or fragments of antibodies, specific for a protein of interest can be used to quantitatively or qualitatively detect the presence of a protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a biological sample (e.g., a biopsy specimen) from a patient, and applying thereto a labeled antibody that is directed to a protein of interest. The antibody (or fragment) is preferably applied by overlaying the antibody (or fragment) onto a biological sample. Through the use of such a procedure, it is possible to determine not only the presence of the protein of interest, but also its distribution, in a particular sample. A wide variety of well-known histological methods (such as staining procedures) can be utilized to achieve such in situ detection.

Immunoassays for a protein of interest typically comprise incubating a sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

The sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional methods.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which an antibody specific for a protein of interest can be detectably labeled is by linking the same to an enzyme and use in an enzyme immunoassay (EIA) (Voller, 1978, "The Enzyme Linked Immunosorbent Assay (ELISA)", Diagnostic Horizons 2:1-7, Microbiological Associates Quarterly Publication, Walkersville, Md.; Voller et al., 1978, J. Clin. Pathol. 31:507-520; Butler, J. E., 1981, Meth. Enzymol. 73:482-523; Maggio (ed.), 1980, Enzyme Immunoassay, CRC Press, Boca Raton, Fla.; Ishikawa et al., (eds.), 1981, Enzyme Immunoassay, Kgaku Shoin, Tokyo, each of which is hereby incorporated by reference in its entirety). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, 1986, Principles of Radioimmunoassays, Seventh Training Course on Radioligand Assay Techniques, The Endocrine Society, which is hereby incorporated by reference in its entirety). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In another embodiment, specific binding molecules other than antibodies, such as aptamers, may be used to bind the biomarkers. In yet another embodiment, the biomarker profile may comprise a measurable aspect of an infectious agent (e.g., lipopolysaccharides or viral proteins) or a component thereof.

In some embodiments, a protein chip assay (e.g., The ProteinChip® Biomarker System, Ciphergen, Fremont, Calif.) is used to measure feature values for the biomarkers in the biomarker profile. See also, for example, Lin, 2004, Modern Pathology, 1-9; Li, 2004, Journal of Urology 171, 1782-1787; Wadsworth, 2004, Clinical Cancer Research, 10, 1625-1632; Prieto, 2003, Journal of Liquid Chromatography & Related Technologies 26, 2315-2328; Coombes, 2003, Clinical Chemistry 49, 1615-1623; Mian, 2003, Proteomics 3, 1725-1737; Lehre et al., 2003, BJU International 92, 223-225; and Diamond, 2003, Journal of the American Society for Mass Spectrometry 14, 760-765, each of which is hereby incorporated by reference in its entirety.

In some embodiments, a bead assay is used to measure feature values for the biomarkers in the biomarker profile. One such bead assay is the Becton Dickinson Cytometric Bead Array (CBA). CBA employs a series of particles with discrete fluorescence intensities to simultaneously detect multiple soluble analytes. CBA is combined with flow cytometry to create a multiplexed assay. The Becton Dickinson CBA system, as embodied for example in the Becton Dickinson Human Inflammation Kit, uses the sensitivity of amplified fluorescence detection by flow cytometry measure soluble analytes in a particle-based immunoassay. Each bead in a CBA provides a capture surface for a specific protein and is analogous to an individually coated well in an ELISA plate. The BD CBA capture bead mixture is in suspension to allow for the detection of multiple analytes in a small volume sample.

In some embodiments, the multiplex analysis method described in U.S. Pat. No. 5,981,180 ("the '180 patent"), hereby incorporated by reference in its entirety, and in particular for its teachings of the general methodology, bead technology, system hardware and antibody detection, is used to measure feature values for the biomarkers in a biomarker profile. For this analysis, a matrix of microparticles is synthesized, where the matrix consists of different sets of microparticles. Each set of microparticles can have thousands of molecules of a distinct antibody capture reagent immobilized on the microparticle surface and can be color-coded by incorporation of varying amounts of two fluorescent dyes. The ratio of the two fluorescent dyes provides a distinct emission spectrum for each set of microparticles, allowing the identification of a microparticle set following the pooling of the various sets of microparticles. U.S. Pat. Nos. 6,268,222 and 6,599,331 also are hereby incorporated by reference in their entirety, and in particular for their teachings of various methods of labeling microparticles for multiplex analysis.

5.4.3 Use of Other Methods of Detection

In some embodiments, a separation method may be used to determine feature values for biomarkers in a biomarker profile, such that only a subset of biomarkers within the sample is analyzed. For example, the biomarkers that are analyzed in a sample may be mRNA species from a cellular extract which has been fractionated to obtain only the nucleic acid biomarkers within the sample, or the biomarkers may be from a fraction of the total complement of proteins within the sample, which have been fractionated by chromatographic techniques.

Feature values for biomarkers in a biomarker profile can also, for example, be generated by the use of one or more of the following methods described below. For example, methods may include nuclear magnetic resonance (NMR) spectroscopy, a mass spectrometry method, such as electrospray ionization mass spectrometry (ESI-MS), ESI-MS/MS, ESI-MS/(MS)$^n$ (n is an integer greater than zero), matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS, APCI-(MS)$^n$, atmospheric pressure photoionization mass spectrometry (APPI-MS), APPI-MS/MS, and APPI-(MS)$^n$. Other mass spectrometry methods may include, inter alia, quadrupole, Fourier transform mass spectrometry (FTMS) and ion trap. Other suitable methods may include chemical extraction partitioning, column chromatography, ion exchange chromatography, hydrophobic (reverse phase) liquid chromatography, isoelectric focusing, one-dimensional polyacrylamide gel electrophoresis (PAGE), two-dimensional polyacrylamide gel electrophoresis (2D-PAGE) or other chromatography, such as thin-layer, gas or liquid chromatography, or any combination thereof. In one embodiment, the biological sample may be fractionated prior to application of the separation method.

In one embodiment, laser desorption/ionization time-of-flight mass spectrometry is used to determine feature values in a biomarker profile where the biomarkers are proteins or protein fragments that have been ionized and vaporized off an immobilizing support by incident laser radiation and the feature values are the presence or absence of peaks representing these fragments in the mass spectra profile. A variety of laser desorption/ionization techniques are known in the art (see, e.g., Guttman et al., 2001, Anal. Chem. 73:1252-62 and Wei et al., 1999, Nature 399:243-246, each of which is hereby incorporated by reference in its entirety).

Laser desorption/ionization time-of-flight mass spectrometry allows the generation of large amounts of information in a relatively short period of time. A biological sample is applied to one of several varieties of a support that binds all of the biomarkers, or a subset thereof, in the sample. Cell lysates or samples are directly applied to these surfaces in volumes as small as 0.5 µL, with or without prior purification or fractionation. The lysates or sample can be concentrated or diluted prior to application onto the support surface. Laser desorption/ionization is then used to generate mass spectra of the sample, or samples, in as little as three hours.

5.4.4 Data Analysis Algorithms

Biomarker expression profile of T-MSC are factors discriminating between clinical grade T-MSC and non-clinical grade T-MSC. The identity of these biomarkers and their corresponding features (e.g., expression levels) can be used to develop a decision rule, or plurality of decision rules, that discriminate between clinical grade and non-clinical grade T-MSC. Specific data analysis algorithms for building a decision rule, or plurality of decision rules, can discriminate between clinical grade T-MSC and non-clinical grade T-MSC. Once a decision rule has been built using these exemplary data analysis algorithms or other techniques known in the art, the decision rule can be used to classify a T-MSC population into one of the two or more phenotypic classes (e.g., a clinical grade or a non-clinical grade T-MSC). This is accomplished by applying the decision rule to a biomarker profile obtained from the cell culture. Such decision rules, therefore, have enormous value as defining the quality of T-MSC.

In a certain embodiment, provided herein is a method for the evaluation of a biomarker profile from a test cell culture compared to biomarker profiles obtained from a cell culture in a control population. In some embodiments, each biomarker profile obtained from the control population, as well as the test cell culture, comprises a feature for each of a plurality of different biomarkers. In some embodiments, this comparison is accomplished by (i) developing a decision rule using the biomarker profiles from the control population and (ii) applying the decision rule to the biomarker profile from the test cell culture. As such, the decision rules applied in some embodiments of the present invention are used to determine whether a test cell culture is clinical grade or non-clinical grade. In certain embodiments, the control population is a clinical grade T-MSC. In other embodiments, the control population is BM-MSC.

In some embodiments of the present invention, when the results of the application of a decision rule indicate that the test cell culture is clinical grade T-MSC, it is used for treatment. If the results of an application of a decision rule indicate that the test cell culture is non-clinical grade T-MSC, the test cell culture is not used for treatment.

5.5 Modification of T-MSC

Provided herein is a method of modifying mesenchymal stem cells to produce a population of modified MSC that has improved immunosuppressive function. The MSC have the following characteristics: (i) contain >95% of cells expressing group-1 markers; (ii) contain >80% of cells expressing group 2 markers; (iii) contain <5% of cells expressing group-3 markers; (iv) expresses IL-10 and TGFβ; (v) contain <2% of cells expressing IL-6, IL-12 and TNFα; and (vi) contains <0.001% of cells co-expressing all group-4 markers, wherein group-1 markers are CD73, CD90, CD105, CD146, CD166, and CD44, group-2 markers are CD13, CD29, CD54, CD49E, group-3 markers are CD45, CD34, CD31 and SSEA4, and group-4 markers are OCT4, NANOG, TRA-1-60 and SSEA4.

Provided herein is a method of increasing immunosuppressive function of T-MSC by increasing the expression of AIF. In an embodiment, the method comprises decreasing the expression of PIF. In an embodiment, the method comprises decreasing the expression of IL6, IL12, TNFα, RAGE and other PIF in T-MSC. In an embodiment, the method comprises increasing the expression of TGFβ and IL-10 in T-MSC.

In certain embodiments, the method comprises genetic and epigenetic modifications of T-MSC that are known in the art. In certain embodiments, the genetic modification or epigenetic regulation includes, but is not limited to, knock-out, small hair pin RNA ("shRNA"), micro RNA ("miRNA"), non-coding RNA ("ncRNA"), morpholino oligo, decoy RNA, DNA methylation regulation, histone methylation regulation, translation inhibition and/or antibody blocking. In certain embodiments, MSC are modified through transposomes, toll-like receptor ligands, or small molecules.

In certain embodiments, small molecules are used to target any of the signaling pathway components of IL-6 signaling. In certain embodiments, the target includes, but is not limited to, gp130, STAT3, Cathepsin S, NFkappaB, IRF5. In certain embodiments, IL-12 expression is decreased in T-MSC by activation of the prostaglandin E2 pathway, by increasing intracellular cyclic AMP levels with cAMP agonists that include, but are not limited to, forskolin, cholera toxin, β1- and β2 adrenoreceptor agonists, by inhibition of the NF-κB Rel-B pathway, by treating T-MSC with apoptotic cells, by treatment with phosphatidylserine, by treatment with butyrate, by treatment with Triptolide or extracts from *Tripterygium wilfordii* or synthetic forms or Triptolide (i.e., Minnelide).

In certain embodiments, MSC may be modified to express a certain marker using methods known in the art of recombinant DNA. In certain embodiments, MSC may be modified by transfection using the nucleotide sequence encoding the marker. The marker can be inserted into an appropriate expression vector, i.e., a vector which contains the necessary elements for the transcription and translation of the inserted coding sequence. The necessary transcriptional and translational elements can also be present. The regulatory regions and enhancer elements can be of a variety of origins, both natural and synthetic. A variety of host-vector systems may be utilized to express the marker. These include, but are not limited to, mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA; and stable cell lines generated by transformation using a selectable marker. The expression elements of vectors vary in their strengths and specificities. Depending on the host-vector system utilized, any one of a number of suitable transcription and translation elements may be used.

Once a vector encoding the appropriate marker has been synthesized, the MSC is transformed or transfected with the vector of interest.

Standard methods of introducing a nucleic acid sequence of interest into the MSC can be used. Transformation may be by any known method for introducing polynucleotides into a host cell, including, for example packaging the polynucleotide in a virus and transducing a host cell with the virus, and by direct uptake of the polynucleotide. Mammalian transformations (i.e., transfections) by direct uptake may be conducted using the calcium phosphate precipitation method of Graham & Van der Eb, 1978, Virol. 52:546, or the various known modifications thereof. Other methods for introducing recombinant polynucleotides into cells, particularly into mammalian cells, include dextran-mediated transfection, calcium phosphate mediated transfection, polybrene mediated transfection, protoplast fusion, electroporation, encapsulation of the polynucleotide(s) in liposomes, and direct microinjection of the polynucleotides into nuclei. Such methods are well-known to one of skill in the art.

In a preferred embodiment, stable cell lines containing the constructs of interest are generated for high throughput screening. Such stable cells lines may be generated by introducing a construct comprising a selectable marker, allowing the cells to grow for 1-2 days in an enriched medium, and then growing the cells on a selective medium. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, anti-metabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

5.6 Stem Cell Collection Composition

The stem cell collection composition can comprise any physiologically-acceptable solution suitable for the collection and/or culture of stem cells, for example, a saline solution (e.g., phosphate-buffered saline, Kreb's solution, modified Kreb's solution, Eagle's solution, 0.9% NaCl. etc.), a culture medium (e.g., DMEM, H.DMEM, etc.), and the like.

The stem cell collection composition can comprise one or more components that tend to preserve stem cells, that is, prevent the stem cells from dying, or delay the death of the stem cells, reduce the number of stem cells in a population of cells that die, or the like, from the time of collection to the time of culturing. Such components can be, e.g., an apoptosis inhibitor (e.g., a caspase inhibitor or JNK inhibitor); a vasodilator (e.g., magnesium sulfate, an antihypertensive drug, atrial natriuretic peptide (ANP), adrenocorticotropin, corticotropin-releasing hormone, sodium nitroprusside, hydralazine, adenosine triphosphate, adenosine, indomethacin or magnesium sulfate, a phosphodiesterase inhibitor, etc.); a necrosis inhibitor (e.g., 2-(1H-indol-3-yl)-3-pentylamino-maleimide, pyrrolidine dithiocarbamate, or clonazepam); a TNF-α inhibitor, and/or an oxygen-carrying perfluorocarbon (e.g., perfluorooctyl bromide, perfluorodecyl bromide, etc.).

The stem cell collection composition can comprise one or more tissue-degrading enzymes, e.g., a metalloprotease, a serine protease, a neutral protease, an RNase, or a DNase, or the like. Such enzymes include, but are not limited to, collagenases (e.g., collagenase I, II, III or IV, a collagenase from *Clostridium histolyticum*, etc.); dispase, thermolysin, elastase, trypsin, LIBERASE, hyaluronidase, and the like.

The stem cell collection composition can comprise a bacteriocidally or bacteriostatically effective amount of an antibiotic. In certain non-limiting embodiments, the antibiotic is a macrolide (e.g., tobramycin), a cephalosporin (e.g., cephalexin, cephradine, cefuroxime, cefprozil, cefador, cefixime or cefadroxil), a clarithromycin, an erythromycin, a penicillin (e.g., penicillin V) or a quinolone (e.g., ofloxacin, ciprofloxacin or norfloxacin), a tetracycline, a streptomycin, etc. In a particular embodiment, the antibiotic is active against Gram(+) and/or Gram(−) bacteria, e.g., *Pseudomonas aeruginosa, Staphylococcus aureus*, and the like.

The stem cell collection composition can also comprise one or more of the following compounds: adenosine (about 1 mM to about 50 mM); D-glucose (about 20 mM to about 100 mM); magnesium ions (about 1 mM to about 50 mM); a macromolecule of molecular weight greater than 20,000 daltons, in one embodiment, present in an amount sufficient to maintain endothelial integrity and cellular viability (e.g., a synthetic or naturally occurring colloid, a polysaccharide such as dextran or a polyethylene glycol present at about 25 g/l to about 100 g/l, or about 40 g/l to about 60 g/l); an antioxidant (e.g., butylated hydroxyanisole, butylated hydroxytoluene, glutathione, vitamin C or vitamin E present at about 25 µM to about 100 µM); a reducing agent (e.g., N-acetylcysteine present at about 0.1 mM to about 5 mM); an agent that prevents calcium entry into cells (e.g., verapamil present at about 2 µM to about 25 µM); nitroglycerin (e.g., about 0.05 g/L to about 0.2 g/L); an anticoagulant, in one embodiment, present in an amount sufficient to help prevent clotting of residual blood (e.g., heparin or hirudin present at a concentration of about 1000 units/1 to about 100,000 units/I); or an amiloride containing compound (e.g., amiloride, ethyl isopropyl amiloride, hexamethylene amiloride, dimethyl amiloride or isobutyl amiloride present at about 1.0 µM to about 5 µM).

5.7 Immunomodulation Using T-MSC

Provided herein is the modulation of the activity (e.g. reduced cell proliferation, reduced cell survival, impaired cell migration to sites of inflammation, reduced ability of the cells to promote or prolong inflammation or enhanced cell functions that promote the restoration of healthy tissue or organ homeostasis) of an immune cell, or plurality of immune cells, by contacting the immune cell(s) with a plurality of T-MSC or iT-MSC. In one embodiment, the method of modulating an immune response comprises contacting a plurality of immune cells with a plurality of T-MSC or iT-MSC for a time sufficient for the T-MSC or iT-MSC to detectably suppress an immune response, wherein the T-MSC or iT-MSC detectably suppress T cell proliferation in a mixed lymphocyte reaction (MLR) assay.

Since BM-MSC or other adult tissue derived MSC have been used to treat many autoimmune diseases, BM-MSC are also used for tissue repairing by limiting inflammation and secret growth and protective factors, and replacing damaged tissues. As shown later in the examples, T-MSC have superior immunosuppressive function to BM-MSC, and thus T-MSC can be used in all areas and diseases that are currently targeted by BM-MSC.

T-MSC or iPS-MSC used for immunomodulation may be derived or obtained from an embryonic stem cell line or induced pluripotent stem cell line, respectively. T-MSC or iPS-MSC used for immunomodulation may also be derived from the same species as the immune cells whose activity is to be modulated or from a different species as that of the immune cells whose activity is to be modulated.

An "immune cell" in the context of this method means any cell of the immune system, particularly T cells and NK (natural killer) cells. Thus, in various embodiments of the method, T-MSC are contacted with a plurality of immune cells, wherein the plurality of immune cells are, or comprise, a plurality of T cells (e.g., a plurality of CD3$^+$ T cells, CD4$^+$ T cells and/or CD8$^+$ T cells) and/or natural killer cells. An "immune response" in the context of the method can be any response by an immune cell to a stimulus normally perceived by an immune cell, e.g., a response to the presence of an antigen. In various embodiments, an immune response can be the proliferation of T cells (e.g., CD3$^+$ T cells, CD4$^+$ T cells and/or CD8$^+$ T cells) in response to a foreign antigen, such as an antigen present in a transfusion or graft, or to a self-antigen, as in an autoimmune disease. The immune response can also be a proliferation of T cells contained within a graft. The immune response can also be any activity of a natural killer (NK) cell, the maturation of a dendritic cell, or the like. The immune response can also be a local, tissue- or organ-specific, or systemic effect of an activity of one or more classes of immune cells, e.g., the immune response can be graft versus host disease, inflammation, formation of inflammation-related scar tissue, an autoimmune condition (e.g., rheumatoid arthritis, Type I diabetes, lupus erythematosus, etc.), and the like.

"Contacting" in this context encompasses bringing the T-MSC and immune cells together in a single container (e.g., culture dish, flask, vial, etc.) or in vivo, for example, the same individual (e.g., mammal, for example, human). In a preferred embodiment, the contacting is for a time sufficient, and with a sufficient number of T-MSC and immune cells, that a change in an immune function of the immune cells is detectable. More preferably, in various embodiments, the contacting is sufficient to suppress immune function (e.g., T cell proliferation in response to an antigen) by at least 50%, 60%, 70%, 80%, 90% or 95%, compared to the immune function in the absence of the T-MSC. Such suppression in an in vivo context can be determined in an in vitro assay; that is, the degree of suppression in the in vitro assay can be extrapolated, for a particular number of T-MSC and a number of immune cells in a recipient individual, to a degree of suppression in the individual.

The invention in certain embodiments provides methods of using T-MSC to modulate an immune response, or the activity of a plurality of one or more types of immune cells, in vitro. Contacting the T-MSC and plurality of immune cells can comprise combining the T-MSC and immune cells in the same physical space such that at least a portion of the plurality of T-MSC interacts with at least a portion of the plurality of immune cells; maintaining the T-MSC and immune cells in separate physical spaces with common medium; or can comprise contacting medium from one or a culture of T-MSC or immune cells with the other type of cell (for example, obtaining culture medium from a culture of T-MSC and resuspending isolated immune cells in the medium). In a specific example, the contacting is a Mixed Lymphocyte Reaction (MLR).

Such contacting can, for example, take place in an experimental setting designed to determine the extent to which a particular plurality of T-MSC is immunomodulatory, e.g., immunosuppressive. Such an experimental setting can be, for example, a mixed lymphocyte reaction (MLR) or regression assay. Procedures for performing the MLR and regression assays are well-known in the art. See, e.g., Schwarz, "The Mixed Lymphocyte Reaction: An In Vitro Test for Tolerance," J. Exp. Med. 127(5):879-890 (1968); Lacerda et al., "Human Epstein-Barr Virus (EBV)-Specific Cytotoxic T Lymphocytes Home Preferentially to and Induce Selective Regressions of Autologous EBV-Induced B Lymphoproliferations in Xenografted C.B-17 Scid/Scid Mice," J. Exp. Med. 183:1215-1228 (1996). In a preferred embodiment, an MLR is performed in which a plurality of T-MSC are contacted with a plurality of immune cells (e.g., lymphocytes, for example, CD3$^+$ CD4$^+$ and/or CD8$^+$ T lymphocytes).

The MLR can be used to determine the immunosuppressive capacity of a plurality of T-MSC. For example, a plurality of T-MSC can be tested in an MLR comprising combining CD4$^+$ or CD8$^+$ T cells, dendritic cells (DC) and T-MSC in a ratio of about 10:1:2, wherein the T cells are stained with a dye such as, e.g., CFSE that partitions into daughter cells, and wherein the T cells are allowed to proliferate for about 6 days. The plurality of T-MSC is immunosuppressive if the T cell proliferation at 6 days in the presence of T-MSC is detectably reduced compared to T cell proliferation in the presence of DC and absence of T-MSC. In such an MLR, T-MSC are either thawed or harvested from culture. About 10,000 T-MSC are resuspended in 100 µl of medium (RPMI 1640, 1 mM HEPES buffer, antibiotics, and 5% pooled human serum), and allowed to attach to the bottom of a well for 2 hours. $CD4^+$ and/or $CD8^+$ T cells are isolated from whole peripheral blood mononuclear cells with Miltenyi magnetic beads. The cells are CFSE stained, and a total of 100,000 T cells ($CD4^+$ T cells alone, $CD8^+$ T cells alone, or equal amounts of $CD4^+$ and $CD8^+$ T cells) are added per well. The volume in the well is brought to 200 µl, and the MLR is allowed to proceed.

In one embodiment, therefore, the invention provides a method of suppressing an immune response comprising contacting a plurality of immune cells with a plurality of T-MSC for a time sufficient for the T-MSC to detectably suppress T cell proliferation in a mixed lymphocyte reaction (MLR) assay.

Populations of T-MSC obtained from different embryonic stem cell lines, can differ in their ability to modulate an activity of an immune cell, e.g., can differ in their ability to suppress T cell activity or proliferation or NK cell activity. It is thus desirable to determine, prior to use, the capacity of a particular population of T-MSC for immunosuppression. Such a capacity can be determined, for example, by testing a sample of the stem cell population in an MLR or regression assay. In one embodiment, an MLR is performed with the sample, and a degree of immunosuppression in the assay attributable to the T-MSC is determined. This degree of immunosuppression can then be attributed to the stem cell population that was sampled. Thus, the MLR can be used as a method of determining the absolute and relative ability of a particular population of T-MSC to suppress immune function. The parameters of the MLR can be varied to provide more data or to best determine the capacity of a sample of T-MSC to immunosuppress. For example, because immunosuppression by T-MSC appears to increase roughly in proportion to the number of T-MSC present in the assay, the MLR can be performed with, in one embodiment, two or more numbers of stem cells, e.g., $1\times10^3$, $3\times10^3$, $1\times10^4$ and/or $3\times10^4$ T-MSC per reaction. The number of T-MSC relative to the number of T cells in the assay can also be varied. For example, T-MSC and T cells in the assay can be present in any ratio of, e.g., about 10:1 to about 1:10, preferably about 1:5, though a relatively greater number of T-MSC or T cells can be used.

The invention also provides methods of using T-MSC to modulate an immune response, or the activity of a plurality of one or more types of immune cells, in vivo. T-MSC and immune cells can be contacted, e.g., in an individual that is a recipient of a plurality of T-MSC. Where the contacting is performed in an individual, in one embodiment, the contacting is between exogenous T-MSC (that is, T-MSC not derived from the individual) and a plurality of immune cells endogenous to the individual. In specific embodiments, the immune cells within the individual are $CD3^+$ T cells. $CD4^+$ T cells, $CD8^+$ T cells, and/or NK cells.

Such immunosuppression using T-MSC would be advantageous for any condition caused or worsened by, or related to, an inappropriate or undesirable immune response. T-MSC-mediated immunomodulation, e.g., immunosuppression, would, for example, be useful in the suppression of an inappropriate immune response raised by the individual's immune system against one or more of its own tissues. In various embodiments, therefore, the invention provides a method of suppressing an immune response, wherein the immune response is an autoimmune disease, e.g., lupus erythematosus, diabetes, rheumatoid arthritis, or multiple sclerosis.

The contacting of the plurality of T-MSC with the plurality of one or more types of immune cells can occur in vivo in the context of, or as an adjunct to, for example, grafting or transplanting of one or more types of tissues to a recipient individual. Such tissues may be, for example, bone marrow or blood; an organ; a specific tissue (e.g., skin graft); composite tissue allograft (i.e., a graft comprising two or more different types of tissues); etc. In this regard, the T-MSC can be used to suppress one or more immune responses of one or more immune cells contained within the recipient individual, within the transplanted tissue or graft, or both. The contacting can occur before, during and/or after the grafting or transplanting. For example, T-MSC can be administered at the time of the transplant or graft. The T-MSC can also, or alternatively, be administered prior to the transplanting or grafting, e.g., about 1, 2, 3, 4, 5, 6 or 7 days prior to the transplanting or grafting. T-MSC can also, or alternatively, be administered to a transplant or graft recipient after the transplantation or grafting, for example, about 1, 2, 3, 4, 5, 6 or 7 days after the transplanting or grafting. Preferably, the plurality of T cells are contacted with the plurality of T-MSC before any detectable sign or symptom of an immune response, either by the recipient individual or the transplanted tissue or graft, e.g., a detectable sign or symptom of graft-versus-host disease or detectable inflammation, is detectable.

In another embodiment, the contacting within an individual is primarily between exogenous T-MSC and exogenous progenitor cells or stem cells, e.g., exogenous progenitor cells or stem cells that differentiate into immune cells. For example, individuals undergoing partial or full immunoablation or myeloablation as an adjunct to cancer therapy can receive T-MSC in combination with one or more other types of stem or progenitor cells. For example, the T-MSC can be combined with a plurality of $CD34^+$ cells, e.g., $CD34^+$ hematopoietic stem cells. Such $CD34^+$ cells can be, e.g., $CD34^+$ cells from a tissue source such as peripheral blood, umbilical cord blood, placental blood, or bone marrow. The $CD34^+$ cells can be isolated from such tissue sources, or the whole tissue source (e.g., units of umbilical cord blood or bone marrow) or a partially purified preparation from the tissue source (e.g., white blood cells from cord blood) can be combined with the T-MSC.

The T-MSC are administered to the individual preferably in a ratio, with respect to the known or expected number of immune cells, e.g., T cells, in the individual, of from about 10:1 to about 1:10, preferably about 1:5. However, a plurality of T-MSC can be administered to an individual in a ratio of in non-limiting examples, about 10,000:1, about 1,000:1, about 100:1, about 10:1, about 1:1, about 1:10, about 1:100, about 1:1,000 or about 1:10,000. Generally, about $1\times10^5$ to about $1\times10^8$ T-MSC per recipient kilogram, preferably about $1\times10^6$ to about $1\times10^7$ T-MSC recipient kilogram can be administered to effect immunosuppression. In various embodiments, a plurality of T-MSC administered to an individual or subject comprises at least, about, or no more than, $1\times10^5$, $3\times10^5$, $1\times10^6$, $3\times10^6$, $1\times10^7$, $3\times10^7$, $1\times10^8$, $3\times10^8$, $1\times10^9$, $3\times10^9$ T-MSC, or more.

The T-MSC can also be administered with one or more second types of stem cells, e.g., mesenchymal stem cells from bone marrow. Such second stem cells can be administered to an individual with T-MSC in a ratio of, e.g., about 1:10 to about 10:1.

To facilitate contacting the T-MSC and immune cells in vivo, the T-MSC can be administered to the individual by any route sufficient to bring the T-MSC and immune cells into contact with each other. For example, the T-MSC can be administered to the individual, e.g., intravenously, intramuscularly, intraperitoneally, or directly into an organ, e.g., pancreas. For in vivo administration, the T-MSC can be formulated as a pharmaceutical composition.

The method of immunosuppression can additionally comprise the addition of one or more immunosuppressive agents, particularly in the in vivo context. In one embodiment, the plurality of T-MSC are contacted with the plurality of immune cells in vivo in an individual, and a composition comprising an immunosuppressive agent is administered to the individual. Immunosuppressive agents are well known in the art and include, e.g., anti-T cell receptor antibodies (monoclonal or polyclonal, or antibody fragments or derivatives thereof), anti-IL-2 receptor antibodies (e.g., Basiliximab (SIMULECT®) or daclizumab (ZENAPAX®), anti T cell receptor antibodies (e.g., Muromonab-CD3), azathioprine, corticosteroids, cyclosporine, tacrolimus, mycophenolate mofetil, sirolimus, calcineurin inhibitors, and the like. In a specific embodiment, the immunosuppressive agent is a neutralizing antibody to macrophage inflammatory protein (MIP)-1α or MIP-1β.

5.8 Preservation of T-MSC and/or T-MSC-DL

T-MSC and/or T-MSC-DL can be preserved, that is, placed under conditions that allow for long-term storage, or conditions that inhibit cell death by, e.g., apoptosis or necrosis. T-MSC and/or T-MSC-DL can be preserved using, e.g., a composition comprising an apoptosis inhibitor, necrosis inhibitor. In one embodiment, the invention provides a method of preserving a population of stem cells comprising contacting a population of stem cells with a stem cell collection composition comprising an inhibitor of apoptosis, wherein the inhibitor of apoptosis is present in an amount and for a time sufficient to reduce or prevent apoptosis in the population of stem cells, as compared to a population of stem cells not contacted with the inhibitor of apoptosis. In a specific embodiment, the inhibitor of apoptosis is a caspase inhibitor. In another specific embodiment, the inhibitor of apoptosis is a JNK inhibitor. In a more specific embodiment, the JNK inhibitor does not modulate differentiation or proliferation of the stem cells. In another embodiment, the stem cell collection composition comprises an inhibitor of apoptosis and an oxygen-carrying perfluorocarbon in separate phases. In another embodiment, the stem cell collection composition comprises an inhibitor of apoptosis and an oxygen-carrying perfluorocarbon in an emulsion. In another embodiment, the stem cell collection composition additionally comprises an emulsifier, e.g., lecithin. In another embodiment, the apoptosis inhibitor and the perfluorocarbon are between about 0° C. and about 25° C. at the time of contacting the stem cells. In another more specific embodiment, the apoptosis inhibitor and the perfluorocarbon are between about 2° C. and 100° C., or between about 2° C. and about 50, at the time of contacting the stem cells. In another more specific embodiment, the contacting is performed during transport of the population of stem cells. In another more specific embodiment, the contacting is performed during freezing and thawing of the population of stem cells.

In another embodiment, the invention provides a method of preserving a population of T-MSC and/or T-MSC-DL comprising contacting the population of stem cells with an inhibitor of apoptosis and an organ-preserving compound, wherein the inhibitor of apoptosis is present in an amount and for a time sufficient to reduce or prevent apoptosis in the population of stem cells, as compared to a population of stem cells not contacted with the inhibitor of apoptosis.

Typically, during T-MSC and/or T-MSC-DL collection, enrichment and isolation, it is preferable to minimize or eliminate cell stress due to hypoxia and mechanical stress. In another embodiment of the method, therefore, a stem cell, or population of stem cells, is exposed to a hypoxic condition during collection, enrichment or isolation for less than six hours during the preservation, wherein a hypoxic condition is a concentration of oxygen that is less than normal blood oxygen concentration. In a more specific embodiment, the population of stem cells is exposed to the hypoxic condition for less than two hours during the preservation. In another more specific embodiment, the population of stem cells is exposed to the hypoxic condition for less than one hour, or less than thirty minutes, or is not exposed to a hypoxic condition, during collection, enrichment or isolation. In another specific embodiment, the population of stem cells is not exposed to shear stress during collection, enrichment or isolation.

The T-MSC and/or T-MSC-DL can be cryopreserved, e.g., in cryopreservation medium in small containers, e.g., ampoules. Suitable cryopreservation medium includes, but is not limited to, culture medium including, e.g., growth medium, or cell freezing medium, for example commercially available cell freezing medium, e.g., C2695, C2639 or C6039 (Sigma). Cryopreservation medium preferably comprises DMSO (dimethylsulfoxide), at a concentration of, e.g., about 10% (v/v). Cryopreservation medium may comprise additional agents, for example, methylcellulose and/or glycerol. T-MSC and/or T-MSC-DL are preferably cooled at about 1° C./min during cryopreservation. A preferred cryopreservation temperature is about −80° C. to about −180° C., preferably about −125° C. to about −140° C. Cryopreserved cells can be transferred to liquid nitrogen prior to thawing for use. In some embodiments, for example, once the ampoules have reached about −90° C., they are transferred to a liquid nitrogen storage area. Cryopreserved cells preferably are thawed at a temperature of about 25° C. to about 40° C., preferably to a temperature of about 37° C.

5.9 Cryopreserved T-MSC and/or T-MSC-DL

The T-MSC and/or T-MSC-DL disclosed herein can be preserved, for example, cryopreserved for later use. Methods for cryopreservation of cells, such as stem cells, are well known in the art. T-MSC and/or T-MSC-DL can be prepared in a form that is easily administrable to an individual. For example, provided herein are T-MSC and/or T-MSC-DL that are contained within a container that is suitable for medical use. Such a container can be, for example, a sterile plastic bag, flask, jar, or other container from which the T-MSC and/or T-MSC-DL can be easily dispensed. For example, the container can be a blood bag or other plastic, medically-acceptable bag suitable for the intravenous administration of a liquid to a recipient. The container is preferably one that allows for cryopreservation of the combined stem cell population. Cryopreserved T-MSC and/or T-MSC-DL can comprise T-MSC and/or T-MSC-DL derived from a single donor, or from multiple donors. The T-MSC and/or T-MSC- DL can be completely HLA-matched to an intended recipient, or partially or completely HLA-mismatched.

In another specific embodiment, the container is a bag, flask, or jar. In a more specific embodiment, the bag is a sterile plastic bag. In a more specific embodiment, the bag is suitable for, allows or facilitates intravenous administration of the T-MSC and/or T-MSC-DL. The bag can comprise multiple lumens or compartments that are interconnected to allow mixing of the T-MSC and/or T-MSC-DL and one or more other solutions, e.g., a drug, prior to, or during, administration. In another specific embodiment, the composition comprises one or more compounds that facilitate cryopreservation of the combined stem cell population. In another specific embodiment, the T-MSC and/or T-MSC-DL is contained within a physiologically-acceptable aqueous solution. In a more specific embodiment, the physiologically-acceptable aqueous solution is a 0.9% NaCl solution. In another specific embodiment, the hES-MSC are HLA-matched to a recipient of the stem cell population. In another specific embodiment, the combined stem cell population comprises hES-MSC that are at least partially HLA-mismatched to a recipient of the stem cell population.

5.10 Differentiation of T-MSC into Multiple Lineages

T-MSC may be differentiated into various cell lineages including neuronal lineage cells or neurons, or adipocytes, or myoblasts, or fibroblasts, or osteoblasts or chondrocytes. Unless specifically indicated, T-MSC may be plated onto cell culture plates coated with gelatin, collagen, fibronectin, Matrigel, laminin, vitronectin, or poly(lysine). T-MSC may be plated at a concentration of $1 \times 10^3$ cells/cm$^2$ to $1 \times 10^4$ cells/cm$^2$ in serum free medium or serum-containing medium with bovine serum FBS or ABHS. T-MSCs plated according to the above mentioned conditions may be differentiated by one of the following methods.

In one embodiment, T-MSC may be differentiated in medium containing 1-50 ng/mL Fibroblast Growth Factor (FGF)-2 (optimally 10 ng/ml) plus 1-50 ng/ml Epidermal Growth Factor (EGF) (optimally 10 ng/ml) plus 0.5-5 ng/ml Platelet-Derived Growth Factor (PDGF) (optimally 1 ng/ml). The medium is changed every 2 to 3 days and the cells are harvested after 2-4 weeks with an expected yield of $0.5 \times 10^6$-$2 \times 10^6$ neuronal lineage cells per $1 \times 10^6$ T-MSC.

In another embodiment, T-MSC may be differentiated into neuronal lineage cells by plating on Poly-L-ornithine and Laminin coated plates. T-MSCs will be differentiated in three stages. Stage 1: 1-50 ng/ml FGF-2 (optimally 10 ng/ml) and 1-50 ng/ml EGF (optimally 10 ng/ml), to prime hMSCs towards a neural fate. Stage 2: 10-200 ng/ml Sonic Hedgehog (SHH) (optimally 100 ng/ml), 1-50 ng/ml FGF-8 (human) (optimally 10 ng/ml) and 50-500 µM AAP (optimally 200 µM), for initiating midbrain specification. Stage 3: 5-500 ng/ml Glial-Derived Neurotrophic Factor (GDNF) (optimally 50 ng/ml) and 50-500 µM AAP (optimally 200 µM), for inducing differentiation and maturation towards a dopaminergic neuronal phenotype. Each stage is applied for 1 week and the adherent cells are passaged by disassociation with Trypsin or TrypLE/dispase between each stage. Growth factors are replenished every day and the medium is changed every 2 days. Expected yield is $0.5 \times 10^6$-$4 \times 10^6$ neuronal lineage cells per $1 \times 10^6$ T-MSC.

In another embodiment, T-MSC may be differentiated into neuronal lineage cells in Neurobasal medium (Gibco) containing 0.25×B-27 supplement plus 10-200 ng/ml Sonic Hedgehog (SHH) (optimally 100 ng/ml), plus 1-50 ng/ml FGF-8 (mouse) (optimally 10 ng/ml) plus 1-200 ng/ml FGF-2 (optimally 50 ng/ml). Cells are harvested after 6- and 12-days. Media is not replaced during this period. Expected yield is $0.5 \times 10^6$-$4 \times 10^6$ neuronal lineage cells per $1 \times 10^6$ T-MSC.

In another embodiment, T-MSC may be differentiated into neuronal lineage cells in two stages. Stage 1: T-MSC are cultured in serum-free medium (DMEM) supplemented with 2 mM glutamine, 1-20 U/ml (optimally 12.5 U/ml) nystatin, N2 supplement, and 2-50 ng/ml (optimally 20 ng/ml) fibroblast growth factor-2 (FGF-2) and 1-50 ng/mL EGF (optimally 10 ng/ml) for 48-72 hours. Stage 2: cells are cultured in Neurobasal medium plus B27 supplement plus 0.1-10 mM (optimally 1 mM) dibutyryl cyclic AMP (dbcAMP), 3-isobutyl-1-methylxanthine (IBMX), and 10-500 µM (optimally 200 µM) ascorbic acid plus 1-100 ng/ml BDNF (optimally 50 ng/ml), 1-50 ng/ml glial-derived neurotrophic factor (GDNF; optimally 10 ng/ml), 0.2-10 ng/ml transforming growth factor-β3 (TGF-β3, optimally 2 ng/ml), and 0.05-5 µM all-transretinoic acid (RA, optimally 0.1 µM). Each stage is applied for 1 week and the adherent cells are passaged by disassociation with Trypsin or TrypLE/dispase between each stage. The medium is changed every 2 days and the expected yield is $0.5 \times 10^6$-$4 \times 10^6$ neuronal lineage cells per $1 \times 10^6$ T-MSC.

In another embodiment, T-MSC may be cultured to induce osteogenic differentiation. T-MSCs will be cultured in low glucose DMEM plus 10% FCS, 1-150 uM (optimally 80 µM) ascorbic acid 2-phosphate, 0.5-5 µM (optimally 1 µM) dexamethasone, and 1-100 mM (optimally 20 mM) beta-glycerophosphate. The medium is changed every 2 to 3 days and the expected yield is $0.5 \times 10^6$-$4 \times 10^6$ neuronal lineage cells per $1 \times 10^8$ T-MSC after 2 weeks.

In another embodiment, T-MSC may be cultured to induce adipogenic differentiation. T-MSCs will be grown in low glucose DMEM plus 20% FCS, 1-10 µg/ml (optimally 5 µg/ml) insulin, 0.5-10 µM (optimally 2 µM) dexamethasone, 0.1-1 mM (optimally 0.5 mM) isobutylmethylxanthine, and 1-100 µM (optimally 60 µM) indomethacin. The medium is changed every 2 to 3 days and the expected yield is $0.5 \times 10^6$-$4 \times 10^6$ neuronal lineage cells per $1 \times 10^6$ T-MSC after 4 weeks.

In another embodiment, T-MSC may be cultured to induce chondrogenic differentiation. T-MSC will be grown in a pellet in high glucose DMEM supplemented with 0.5-10 mM (optimally 1 mM) Sodium Pyruvate, 0.05-1 mM (optimally 0.1 mM) ascorbic acid 2-phosphate, 0.05-1 µM (optimally 0.1 µM) dexamethasone, 0.2-2% (optimally 1%) ITS, and 1-50 ng/ml (optimally 10 ng/mL) TGF-β3. The medium is changed every 2 to 3 days and the expected yield is $0.5 \times 10^6$-$4 \times 10^6$ neuronal lineage cells per $1 \times 10^6$ T-MSC after 20 days.

In another embodiment, T-MSC may be cultured to induce myogenic differentiation. T-MSC will be grown in low-glucose DMEM supplemented with 10% FBS, 1-20 µM (optimally 10 µM) 5-azacytidine, and 1-50 ng/ml (optimally 10 ng/ml) basic FGF. After 24 hours, the myogenic induction medium will be replaced with DMEM supplemented with 10% FBS plus 1-50 ng/ml (optimally 10 ng/ml) basic FGF. The medium is changed every 2 to 3 days and the expected yield is $0.5 \times 10^6$-$4 \times 10^6$ neuronal lineage cells per $1 \times 10^6$ T-MSC after 2 weeks.

In another embodiment, T-MSC may be cultured to induce fibroblast differentiation. T-MSC will be grown in hMSCs that were treated with DMEM plus 10% FBS supplemented 50-200 ng/ml (optimally 100 ng/ml) of recombinant human Connective Tissue Growth Factor (CTGF) and 1-100 µg/ml (optimally 50 µg/ml) ascorbic acid. The medium is changed every 3 to 4 days and the expected yield is $0.5 \times 10^6$-$4 \times 10^6$ neuronal lineage cells per $1 \times 10^6$ T-MSC after 4 weeks.

All the cell lineages and cell types derived from T-MSC using any differentiation methods including, but not limited to, the methods above are called T-MSC-DL throughout.

5.11 Pharmaceutical Preparations

In one embodiment, provided herein is a pharmaceutical composition comprising a therapeutically effective amount of a T-MSC and a pharmaceutically acceptable carrier.

The pharmaceutical compositions can comprise any number of T-MSC and/or T-MSC-DL. For example, a single unit dose of T-MSC can comprise, in various embodiments, about, at least, or no more than $1 \times 10^5$, $5 \times 10^5$, $1 \times 10^6$, $5 \times 10^6$, $1 \times 10^7$, $5 \times 10^7$, $1 \times 10^8$, $5 \times 10^8$, $1 \times 10^9$, $5 \times 10^9$, $1 \times 10^{10}$, $5 \times 10^{10}$, $1 \times 10^{11}$ or more T-MSC and/or T-MSC-DL.

The pharmaceutical compositions disclosed herein comprise populations of cells that comprise 50% viable cells or more (that is, at least 50% of the cells in the population are functional or living). Preferably, at least 60% of the cells in the population are viable. More preferably, at least 70%, 80%, 90%, 95%, or 99% of the cells in the population in the pharmaceutical composition are viable.

The pharmaceutical compositions disclosed herein can comprise one or more compounds that, e.g., facilitate engraftment (e.g., anti-T-cell receptor antibodies, an immunosuppressant, or the like); stabilizers such as albumin, dextran 40, gelatin, hydroxyethyl starch, and the like.

The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of a Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

These compositions can take the form of solutions, suspensions, emulsions, tablets, pills, capsules, powders, sustained-release formulations, cachets, troches, lozenges, dispersions, suppositories, ointments, cataplasms (poultices), pastes, powders, dressings, creams, plasters, patches, aerosols, gels, liquid dosage forms suitable for parenteral administration to a patient, and sterile solids (e.g., crystalline or amorphous solids) that can be reconstituted to provide liquid dosage forms suitable for parenteral administration to a patient. Such compositions will contain a therapeutically effective amount of the compound, preferably in purified form, together with a suitable form of carrier so as to provide the form for proper administration to the patient. The formulation should suit the mode of administration.

Pharmaceutical compositions adapted for oral administration may be capsules, tablets, powders, granules, solutions, syrups, suspensions (in non-aqueous or aqueous liquids), or emulsions. Tablets or hard gelatin capsules may comprise lactose, starch or derivatives thereof, magnesium stearate, sodium saccharine, cellulose, magnesium carbonate, stearic acid or salts thereof. Soft gelatin capsules may comprise vegetable oils, waxes, fats, semi-solid, or liquid polyols. Solutions and syrups may comprise water, polyols, and sugars. An active agent intended for oral administration may be coated with or admixed with a material that delays disintegration and/or absorption of the active agent in the gastrointestinal tract. Thus, the sustained release may be achieved over many hours and if necessary, the active agent can be protected from degradation within the stomach. Pharmaceutical compositions for oral administration may be formulated to facilitate release of an active agent at a particular gastrointestinal location due to specific pH or enzymatic conditions.

Pharmaceutical compositions adapted for transdermal administration may be provided as discrete patches intended to remain in intimate contact with the epidermis of the recipient over a prolonged period of time.

Pharmaceutical compositions adapted for nasal and pulmonary administration may comprise solid carriers such as powders which can be administered by rapid inhalation through the nose. Compositions for nasal administration may comprise liquid carriers, such as sprays or drops. Alternatively, inhalation directly through into the lungs may be accomplished by inhalation deeply or installation through a mouthpiece. These compositions may comprise aqueous or oil solutions of the active ingredient. Compositions for inhalation may be supplied in specially adapted devices including, but not limited to, pressurized aerosols, nebulizers or insufflators, which can be constructed so as to provide predetermined dosages of the active ingredient.

Pharmaceutical compositions adapted for parenteral administration include aqueous and non-aqueous sterile injectable solutions or suspensions, which may contain anti-oxidants, buffers, bacteriostats, and solutes that render the compositions substantially isotonic with the blood of the subject. Other components which may be present in such compositions include water, alcohols, polyols, glycerine, and vegetable oils. Compositions adapted for parental administration may be presented in unit-dose or multi-dose containers, such as sealed ampules and vials, and may be stored in a freeze-dried (lyophilized) condition requiring only the addition of a sterile carrier, immediately prior to use. Extemporaneous injection solutions and suspensions may be prepared from sterile powders, granules, and tablets. Suitable vehicles that can be used to provide parenteral dosage forms of the invention are well known to those skilled in the art. Examples include: Water for Injection USP; aqueous vehicles such as Sodium Chloride Injection, Ringers Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

Selection of a therapeutically effective dose will be determined by the skilled artisan considering several factors which will be known to one of ordinary skill in the art. Such factors include the particular form of the inhibitor, and its pharmacokinetic parameters such as bioavailability, metabolism, and half-life, which will have been established during the usual development procedures typically employed in obtaining regulatory approval for a pharmaceutical compound. Further factors in considering the dose include the condition or disease to be treated or the benefit to be achieved in a normal individual, the body mass of the patient, the route of administration, whether the administration is acute or chronic, concomitant medications, and other factors well known to affect the efficacy of administered pharmaceutical agents. Thus, the precise dose should be decided according to the judgment of the person of skill in the art, and each patient's circumstances, and according to standard clinical techniques.

In certain embodiments, patients are treated with antipyretic and/or antihistamine (acetaminophen and diphenhydramine hydrochloride) to minimize any possible DMSO infusion toxicity related to the cryopreserve component in the hES-MSC treatment.

5.12 T-MSC Conditioned Media and Derivatives

The T-MSC disclosed herein can be used to produce conditioned medium that is immunosuppressive, that is, medium comprising one or more biomolecules secreted or excreted by the stem cells that have a detectable immunosuppressive effect on a plurality of one or more types of immune cells. In various embodiments, the conditioned medium comprises medium in which T-MSC have grown for at least 1, 2, 3, 4, 5, 6, 7, 8, 9, 10, 11, 12, 13, 14 or more days. In other embodiments, the conditioned medium comprises medium in which T-MSC have grown to at least 30%, 40%, 50%, 60%, 70%, 80%, 90% confluence, or up to 100% confluence. Such conditioned medium can be used to support the culture of a separate population of T-MSC, or stem cells of another kind. In another embodiment, the conditioned medium comprises medium in which T-MSC have been differentiated into an adult cell type. In another embodiment, the conditioned medium of the invention comprises medium in which T-MSC and non-T-MSC have been cultured.

Thus, in one embodiment, the invention provides a composition comprising culture medium, cell lysate and/or other derivatives from a culture of T-MSC, wherein the T-MSC (a) adhere to a substrate; (b) express CD73, CD105, CD90, CD29, CD44, CD146, IL-10, TGFb2, HGF, but do not express IL-6, TNFα, IL-12 and/or RAGE. In another specific embodiment, the composition comprises an anti-proliferative agent, e.g., an anti-MIP-1α or anti-MIP-1β antibody.

Provided herein is a method of using T-MSC as described herein as feeder cells for bone marrow hematopoietic stem cell, peripheral blood hematopoietic stem cell and umbilical-cord hematopoietic stem cell expansion. In certain embodiments, the T-MSC suitable for the disclosed method express Stro-3, Stro-1, DL1, and/or Nestin. The T-MSC can also be modified or engineered to express high level of Stro-3, Stro-1, DL1, Nestin or Frizzle using the method disclosed herein in Section 5.5. In certain embodiments, T-MSC is co-cultured with bone marrow hematopoietic stem cells, peripheral blood hematopoietic stem cells and/or umbilical-cord hematopoietic stem cells. In certain embodiments, the T-MSC are mesenchymal stromal cells. Provided herein is a co-culture of T-MSC as described herein and bone marrow hematopoietic stem cells. Provided herein is a co-culture of T-MSC as described herein and umbilical-cord hematopoietic stem cells.

5.13 Matrices Comprising T-MSC and/or T-MSC Derived Lineages

The invention further comprises matrices, hydrogels, scaffolds, and the like that comprise T-MSC and/or T-MSC-DL. T-MSC and/or T-MSC-DL can be seeded onto a natural matrix, e.g., a biomaterial. In certain embodiments, the scaffold is obtained by 3D printing. The T-MSC and/or T-MSC-DL can be suspended in a hydrogel solution suitable for, e.g., injection. Suitable hydrogels for such compositions include self-assembling peptides, such as RAD16. In one embodiment, a hydrogel solution comprising the cells can be allowed to harden, for instance in a mold, to form a matrix having cells dispersed therein for implantation. T-MSC and/or T-MSC-DL in such a matrix can also be cultured so that the cells are mitotically expanded prior to implantation. The hydrogel is, e.g., an organic polymer (natural or synthetic) that is cross-linked via covalent, ionic, or hydrogen bonds to create a three-dimensional open-lattice structure that entraps water molecules to form a gel. Hydrogel-forming materials include polysaccharides such as alginate and salts thereof, peptides, polyphosphazines, and polyacrylates, which are cross-linked ionically, or block polymers such as polyethylene oxide-polypropylene glycol block copolymers which are cross-linked by temperature or pH, respectively. In some embodiments, the hydrogel or matrix of the invention is biodegradable. In some embodiments of the invention, the formulation comprises an in situ polymerizable gel (see, e.g., U.S. Patent Application Publication 2002/0022676; Anseth et al., J. Control Release, 78(1-3): 199-209 (2002); Wang et al., Biomaterials, 24(22):3969-80 (2003).

In some embodiments, the polymers are at least partially soluble in aqueous solutions, such as water, buffered salt solutions, or aqueous alcohol solutions, that have charged side groups, or a monovalent ionic salt thereof. Examples of polymers having acidic side groups that can be reacted with cations are poly(phosphazenes), poly(acrylic acids), poly (methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

The T-MSC, T-MSC-DL and/or co-cultures thereof can be seeded onto a three-dimensional framework or scaffold and implanted in vivo. Such a framework can be implanted in combination with any one or more growth factors, cells, drugs or other components that stimulate tissue formation or otherwise enhance or improve the practice of the invention.

Examples of scaffolds that can be used in the present invention include nonwoven mats, porous foams, or self-assembling peptides. Nonwoven mats can be formed using fibers comprised of a synthetic absorbable copolymer of glycolic and lactic acids (e.g., PGA/PLA) (VICRYL, Ethicon, Inc., Somerville, N.J.). Foams, composed of, e.g., poly(s-caprolactone)/poly(glycolic acid) (PCL/PGA) copolymer, formed by processes such as freeze-drying, or lyophilization (see, e.g., U.S. Pat. No. 6,355,699), can also be used as scaffolds.

The T-MSC and/or T-MSC-DL can also be seeded onto, or contacted with, a physiologically-acceptable ceramic material including, but not limited to, mono-, di-, tri-, alpha-tri-, beta-tri-, and tetra-calcium phosphate, hydroxyapatite, fluoroapatites, calcium sulfates, calcium fluorides, calcium oxides, calcium carbonates, magnesium calcium phosphates, biologically active glasses such as BIOGLASS®, and mixtures thereof. Porous biocompatible ceramic materials currently commercially available include SURGIBONE® (CanMedica Corp., Canada), ENDOBON® (Merck Biomaterial France, France), CEROS® (Mathys, AG, Bettlach, Switzerland), and mineralized collagen bone grafting products such as HEALOS™ (DePuy, Inc., Raynham, Mass.) and VITOSS®, RHAKOSS™, and CORTOSS® (Orthovita, Malvern, Pa.). The framework can be a mixture, blend or composite of natural and/or synthetic materials.

In another embodiment, T-MSC and/or T-MSC-DL can be seeded onto, or contacted with, a felt, which can be, e.g., composed of a multifilament yarn made from a bioabsorbable material such as PGA, PLA, PCL copolymers or blends, or hyaluronic acid.

The T-MSC and/or T-MSC-DL can, in another embodiment, be seeded onto foam scaffolds that may be composite structures. Such foam scaffolds can be molded into a useful shape, such as that of a portion of a specific structure in the body to be repaired, replaced or augmented. In some embodiments, the framework is treated, e.g., with 0.1M acetic acid followed by incubation in polylysine, PBS, and/or collagen, prior to inoculation of the cells of the invention in order to enhance cell attachment. External surfaces of a matrix may be modified to improve the attachment or growth of cells and differentiation of tissue, such as by plasma-coating the matrix, or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate, etc.), a cellular matrix, and/or other materials such as, but not limited to, gelatin, alginates, agar, agarose, and plant gums, and the like.

In some embodiments, the scaffold comprises, or is treated with, materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as EPTFE, and segmented polyurethaneurea silicones, such as PURSPAN™ (The Polymer Technology Group, Inc., Berkeley, Calif.). The scaffold can also comprise anti-thrombotic agents such as heparin; the scaffolds can also be treated to alter the surface charge (e.g., coating with plasma) prior to seeding with stem cells.

5.14 Immortalized T-MSC and/or T-MSC-DL

Mammalian T-MSC and/or T-MSC-DL can be conditionally immortalized by transfection with any suitable vector containing a growth-promoting gene, that is, a gene encoding a protein that, under appropriate conditions, promotes growth of the transfected cell, such that the production and/or activity of the growth-promoting protein is relatable by an external factor. In a preferred embodiment the growth-promoting gene is an oncogene such as, but not limited to, v-myc, N-myc, c-myc, p53, SV40 large T antigen, polyoma large T antigen, E1a adenovirus or E7 protein of human papillomavirus.

External regulation of the growth-promoting protein can be achieved by placing the growth-promoting gene under the control of an externally-regulatable promoter, e.g., a promoter the activity of which can be controlled by, for example, modifying the temperature of the transfected cells or the composition of the medium in contact with the cells. In one embodiment, a tetracycline (tet)-controlled gene expression system can be employed (see Gossen et al., Proc. Natl. Acad. Sci. USA 89:5547-5551, 1992; Hoshimaru et al., Proc. Natl. Acad. Sci. USA 93:1518-1523, 1996). In the absence of tet, a tet-controlled transactivator (tTA) within this vector strongly activates transcription from $_{ph}$CMV*-1, a minimal promoter from human cytomegalovirus fused to tet operator sequences. tTA is a fusion protein of the repressor (tetR) of the transposon-10-derived tet resistance operon of Escherichia coli and the acidic domain of VP16 of herpes simplex virus. Low, non-toxic concentrations of tet (e.g., 0.01-1.0 µg/mL) almost completely abolish transactivation by tTA.

In one embodiment, the vector further contains a gene encoding a selectable marker, e.g., a protein that confers drug resistance. The bacterial neomycin resistance gene ($neo^R$) is one such marker that may be employed within the present invention. Cells carrying $neo^R$ may be selected by means known to those of ordinary skill in the art, such as the addition of, e.g., 100-200 µg/mL G418 to the growth medium.

Transfection can be achieved by any of a variety of means known to those of ordinary skill in the art including, but not limited to, retroviral infection. In general, a cell culture may be transfected by incubation with a mixture of conditioned medium collected from the producer cell line for the vector and DMEM/F12 containing N2 supplements. For example, a stem cell culture prepared as described above may be infected after, e.g., five days in vitro by incubation for about 20 hours in one volume of conditioned medium and two volumes of DMEM/F12 containing N2 supplements. Transfected cells carrying a selectable marker may then be selected as described above.

Following transfection, cultures are passaged onto a surface that permits proliferation, e.g., allows at least 30% of the cells to double in a 24 hour period. Preferably, the substrate is a polyornithine/laminin substrate, consisting of tissue culture plastic coated with polyornithine (10 µg/mL) and/or laminin (10 µg/mL), a polylysine/laminin substrate or a surface treated with fibronectin. Cultures are then fed every 3-4 days with growth medium, which may or may not be supplemented with one or more proliferation-enhancing factors. Proliferation-enhancing factors may be added to the growth medium when cultures are less than 50% confluent.

The conditionally-immortalized T-MSC and/or T-MSC-DL cell lines can be passaged using standard techniques, such as by trypsinization, when 80-95% confluent. Up to approximately the twentieth passage, it is, in some embodiments, beneficial to maintain selection (by, for example, the addition of G418 for cells containing a neomycin resistance gene). Cells may also be frozen in liquid nitrogen for long-term storage.

Clonal cell lines can be isolated from a conditionally-immortalized human T-MSC cell line prepared as described above. In general, such clonal cell lines may be isolated using standard techniques, such as by limiting dilution or using cloning rings, and expanded. Clonal cell lines may generally be fed and passaged as described above.

Conditionally-immortalized human T-MSC cell lines, which may, but need not, be clonal, may generally be induced to differentiate by suppressing the production and/or activity of the growth-promoting protein under culture conditions that facilitate differentiation. For example, if the gene encoding the growth-promoting protein is under the control of an externally-regulatable promoter, the conditions, e.g., temperature or composition of medium, may be modified to suppress transcription of the growth-promoting gene. For the tetracycline-controlled gene expression system discussed above, differentiation can be achieved by the addition of tetracycline to suppress transcription of the growth-promoting gene. In general, 1 µg/mL tetracycline for 4-5 days is sufficient to initiate differentiation. To promote further differentiation, additional agents may be included in the growth medium.

5.15 Assays

The T-MSC and/or T-MSC-DL can be used in assays to determine the influence of culture conditions, environmental factors, molecules (e.g., biomolecules, small inorganic molecules, etc.) and the like on stem cell proliferation, expansion, and/or differentiation, compared to T-MSC and/or T-MSC-DL not exposed to such conditions.

In a preferred embodiment, the T-MSC and/or T-MSC-DL are assayed for changes in proliferation, expansion or differentiation upon contact with a molecule. In one embodiment, for example, the invention provides a method of identifying a compound that modulates the proliferation of a plurality of T-MSC and/or T-MSC-DL, comprising contacting the plurality of T-MSC and/or T-MSC-DL with the compound under conditions that allow proliferation, wherein if the compound causes a detectable change in proliferation of the T-MSC and/or T-MSC-DL compared to a plurality of T-MSC and/or T-MSC-DL not contacted with the compound, the compound is identified as a compound that modulates proliferation of T-MSC and/or T-MSC-DL. In a specific embodiment, the compound is identified as an inhibitor of proliferation. In another specific embodiment, the compound is identified as an enhancer of proliferation.

In another embodiment, the invention provides a method of identifying a compound that modulates the expansion of a plurality of T-MSC and/or T-MSC-DL, comprising contacting the plurality of T-MSC and/or T-MSC-DL with the compound under conditions that allow expansion, wherein if the compound causes a detectable change in expansion of the plurality of T-MSC and/or T-MSC-DL compared to a plurality of T-MSC and/or T-MSC-DL not contacted with the compound, the compound is identified as a compound that modulates expansion of T-MSC and/or T-MSC-DL. In a specific embodiment, the compound is identified as an inhibitor of expansion. In another specific embodiment, the compound is identified as an enhancer of expansion.

In another embodiment, disclosed herein is a method of identifying a compound that modulates the differentiation of a T-MSC and/or T-MSC-DL, comprising contacting a T-MSC and/or T-MSC-DL with a compound under conditions that allow differentiation, wherein if the compound causes a detectable change in differentiation of the T-MSC and/or T-MSC-DL compared to a T-MSC and/or T-MSC-DL not contacted with the compound, the compound is identified as a compound that modulates proliferation of T-MSC and/or T-MSC-DL. In a specific embodiment, the compound is identified as an inhibitor of differentiation. In another specific embodiment, the compound is identified as an enhancer of differentiation.

5.16 Therapeutic Uses of Human Embryonic Stem Cell Derived Mesenchymal Stem Cells Mesenchymal stem cells derived from bone marrow (BM-MSCs) have been used as cell based therapy for T cell related autoimmune diseases, including multiple sclerosis (MS), but due to limited sources, unstable quality, and biosafety concerns of using cells derived from adult tissue, their use as a therapeutic aid has been limited.

The novel method for generating mesenchymal stem cells from embryonic stem cells set forth herein, and the novel T-MSC generated from this method, provide new therapies for T cell related autoimmune disease, in particular multiple sclerosis.

In certain embodiments, T-MSC given to mice pre-onset of EAE, remarkably attenuated the disease score of these animals. The decrease in score was accompanied by decreased demyelination, T cell infiltration, and microglial responses in the central nervous system, as well as repressed immune cell proliferation, and differentiation in vitro.

In certain embodiments, a gradual decline of disease score in EAE mice after treatment with T-MSC, post disease onset, was observed. In certain embodiments, T-MSC have both prophylactic and therapeutic effects on the disease.

In certain embodiments, the immunosuppressive activity of the T-MSC account for the prophylactic effect on the disease as irradiated T-MSC, which are unlikely to replace damage myelin, and were also effective in reducing disease score. In one embodiment, irradiation does not shorten the lifespan of the T-MSC.

In certain embodiments, the therapeutic effect of the T-MSC involve immunosuppression as well as neural repair and regeneration.

In certain embodiment, EAE mice treated with T-MSC have much fewer inflammatory T cells in their central nervous system and less T cells infiltrating the spinal cord. The T-MSC can reduce damage and symptoms caused by inflammatory T cells, making them useful in therapy and prevention of all T cell related autoimmune diseases. T-MSC also decreased demyelination.

The characteristics of the T-MSC are all in marked contrast to the results obtained with bone marrow-derived mesenchymal stem cells. BM-MSCs only suppressed mouse T cell proliferation in response to anti-CD3 stimuli at low doses in vitro, and even enhanced Th1 and Th17 cell infiltration into the CNS. Autoreactive effector $CD4^+$ T cells have been associated with the pathogenesis of several autoimmune disorders, including multiple sclerosis, Crohn's disease, and rheumatoid arthritis. These CD4+ T cells include Th1 and Th17 cells. There are only mild or negligible effects of human BM-MSCs on EAE mice (Gordon et al. 2008a; Zhang et al. 2005; Payne et al. 2012). A recent report showed a reduction of disease score of only 3.5 to 3.0 of EAE mice treated with human umbilical-derived MSCs (Liu et al. 2012). The results herein and those from these studies highlight the novelty and usefulness of the disclosed T-MSC.

Additionally, BM-MSC and T-MSC have very similar global transcriptional profiles, but differentially express some pro- and anti-inflammatory factors. Among them, IL-8 is expressed at a much higher level in BM-MSCs than T-MSC. Moreover, IL-6 expression in BM-MSCs was double upon IFNγ stimulation in vitro, whereas it remained low in the T-MSC.

IL-6 is a pleiotropic cytokine involved in crosstalk between hematopoietic/immune cells and stromal cells, including the onset and resolution of inflammation. IL-6 can promote the differentiation and functions of Th17 cells (Dong, 2008). The levels of IL-6 are elevated in mononuclear cells in blood and in brain tissue from MS patients (Patanella et al., 2010), as well as in serum in aged humans (Sethe et al., 2006). Mice lacking IL-6 receptor a at the time of T cell priming are resistant to EAE (Leech et al., 2012). Site-specific production of IL-6 in the CNS can re-target and enhance the inflammatory response in EAE (Quintana et al., 2009), whereas IL-6-neutralizing antibody can reduce symptoms in EAE mice (Gijbels et al., 1995). Thus, IL-6 has become a promising therapeutic target for treatment of MS.

Immunomodulation of peripheral T cell activity and regeneration and repair of neural cells are widely recognized modes of MSC therapeutic action in MS and in EAE (A Jumah and Abumaree, 2012; Auletta et al., 2012; Morando et al., 2012). However, long-term functional neuronal recovery and sustained disease remission in MS needs repair of the damaged blood-brain barrier and blood-spinal cord barrier (Correale and Villa, 2007; Minagar et al., 2012). In other words, MS is an inflammatory, neurodegenerative, and vascular disease, and effective treatment need to target all three component.

The characteristics of T-MSC make them uniquely suited for the treatment of T cell related autoimmune diseases especially multiple sclerosis. In particular, the T-MSC can decrease disease scores of EAE mice, but also decrease demyelination and decrease Th1 and Th17 proliferation, and have low expression of IL-6. These latter two characteristics make them suitable to treat other T cell related autoimmune diseases. Additionally, the ability of the T-MSC to cross the blood-brain barrier and blood-spinal cord barrier, makes them superior as a treatment and prevention of multiple sclerosis and other autoimmune diseases related to the central nervous system.

One embodiment provided herein is a method of treating or preventing a T cell related autoimmune disease comprising the steps of administering a therapeutically effective amount of solution, cell culture or pharmaceutical preparation comprising T-MSC to the subject in need thereof. The T cell related autoimmune diseases would include but are not limited to multiple sclerosis, inflammatory bowel disease, Crohn's disease, graft versus host disease, systemic lupus erythematosus, and rheumatoid arthritis. The subject is preferably a mammal, and most preferably human. The solution, cell culture or pharmaceutical preparation can comprise irradiated or non-irradiated T-MSC. The solution, cell culture or pharmaceutical preparation is preferably administered by injection.

Multiple sclerosis has been categorized into four subtypes: relapsing/remitting; secondary progressive; primary progressive; and progressive relapsing. The relapsing/remitting subtype is characterized by unpredictable relapses followed by long periods of remission. Secondary progressive MS often happens in individuals who start with relapsing/remitting MS and then have a progressive decline with no periods of remission. Primary progressive MS describes a small number of individuals who never have remission after their initial symptoms. Individuals with progressive relapsing, the least common subtype, have a steady neurologic decline, and suffer from acute attacks.

Provided herein is a method for treating or preventing multiple sclerosis disease in a subject in need thereof, comprising the steps of administering a therapeutically effective amount of solution, cell culture or pharmaceutical preparation comprising T-MSC as described in the preceding paragraphs, to the subject in need thereof. The multiple sclerosis can be relapsing/remitting multiple sclerosis, progressive/relapsing multiple sclerosis, primary multiple sclerosis, or secondary multiple sclerosis. The subject is preferably a mammal, and most preferably human. The solution, cell culture or pharmaceutical preparation can comprise irradiated or non-irradiated T-MSC. The solution, cell culture or pharmaceutical preparation is preferably administered by injection.

Multiple sclerosis manifests in a variety of symptoms including sensory disturbance of the limbs, optic nerve dysfunction, pyramidal tract dysfunction, bladder dysfunction, bowel dysfunction, sexual dysfunction, ataxia and diplopia attacks.

A further embodiment of the present invention is a method of treating multiple sclerosis comprising the steps of administering a therapeutically effective amount of solution, cell culture or pharmaceutical preparation comprising T-MSC, to the subject in need thereof, wherein there is detectable improvement in at least one of these symptoms, at least two of these symptoms, at least four of these symptoms, at least five of these symptoms or all of these symptoms.

The Expanded Disability Status Scale (EDSS) is the most commonly used rating scale to evaluate the clinical status of patients with multiple sclerosis. It measures disability along several separate parameters: strength, sensation, brainstem functions (speech and swallowing), coordination, vision, cognition, and bowel/bladder continence. It is a well-accepted measure of disability in MS and it is not particularly difficult or time consuming to perform. The EDSS quantifies disability in eight Functional Systems (FS) and allows neurologists to assign a Functional System Score (FSS) in each of these (Kurtzke 1983).

Kurtzke defines functional systems as follows:
pyramidal
cerebellar
brainstem
sensory
bowel and bladder
visual
cerebral
other The EDSS steps 1.0 to 4.5 refer to people with multiple sclerosis who are fully ambulatory. EDSS steps 5.0 to 9.5 are defined by the impairment to ambulation. The clinical meaning of each possible result is the following:

0.0: Normal Neurological Exam
1.0: No disability, minimal signs on 1 FS
1.5: No disability, minimal signs on 2 of 7 FS
2.0: Minimal disability in 1 of 7 FS
2.5: Minimal disability in 2 FS
3.0: Moderate disability in 1 FS; or mild disability in 3-4 FS, though fully ambulatory
3.5: Fully ambulatory but with moderate disability in 1 FS and mild disability in 1 or 2 FS; or moderate disability in 2 FS; or mild disability in 5 FS
4.0: Fully ambulatory without aid, up and about 12 hrs a day despite relatively severe disability. Able to walk without aid 500 meters
4.5: Fully ambulatory without aid, up and about much of day, able to work a full day, may otherwise have some limitations of full activity or require minimal assistance. Relatively severe disability. Able to walk without aid 300 meters
5.0: Ambulatory without aid for about 200 meters. Disability impairs full daily activities
5.5: Ambulatory for 100 meters, disability precludes full daily activities
6.0: Intermittent or unilateral constant assistance (cane, crutch or brace) required to walk 100 meters with or without resting 6.5: Constant bilateral support (cane, crutch or braces) required to walk 20 meters without resting 7.0: Unable to walk beyond 5 meters even with aid, essentially restricted to wheelchair, wheels self, transfers alone; active in wheelchair about 12 hours a day 7.5: Unable to take more than a few steps, restricted to wheelchair, may need aid to transfer; wheels self, but may require motorized chair for full day's activities 8.0: Essentially restricted to bed, chair, or wheelchair, but may be out of bed much of day; retains self-care functions, generally effective use of arms 8.5: Essentially restricted to bed much of day, some effective use of arms, retains some self-care functions 9.0: Helpless bed patient, can communicate and eat 9.5: Unable to communicate effectively or eat/swallow 10.0: Death due to MS Provided herein is a method for treating multiple sclerosis disease in a subject in need thereof, comprising the steps of administering a therapeutically effective amount of solution, cell culture or pharmaceutical preparation comprising T-MSC, to the subject in need thereof wherein the subject demonstrates improvement on the Expanded Disability Status Scale of at least one point, and preferably at least two points.

There are other therapeutic agents that have been used to treat and prevent multiple sclerosis, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine.

Therefore, the method of the present invention can further comprise the administration of one or more additional therapeutic agents to the subject, including but not limited to, fingolimod, adrenocorticotropic hormone (ACTH), methylprednisolone, dexamethasone, IFNβ-1a, IFN-1b, gliatriamer acetate, cyclophosphamide, methotrexate, azathioprine, cladribine, cyclosporine, mitoxantrone, and sulfasalazine. In a further embodiment, these additional therapeutic agents can be administered prior to, after, or at the same time as the T-MSC, or can be conjugated or attached to the T-MSC.

Other than T cells, T-MSC also have strong suppressive function on B cells, dendritic cells, neutrophils, NK cells, macrophage and other inflammatory and immunity related functions. Thus, T cell, B cell, inflammatory and/or innate immunity related autoimmune diseases that can all be treated by the disclosed T-MSC include, but are not limited to, Alopecia Areata, Anklosing Spondylitis, Antiphospholipid Syndrome, Autoimmune Addison's Disease, Autoimmune Hemolytic Anemia, Autoimmune Hepatitis, Autoimmune Inner Ear Disease, Autoimmune Lymphoproliferative Syndrome (ALPS), Autoimmune Thrombocytopenic Purpura (ATP), Behcet's Disease, Bullous Pemphigoid, Cardiomyopathy, Celiac Sprue-Dermatitis, Chronic Fatigue Syndrome Immune Deficiency Syndrome (CFIDS). Chronic Inflammatory Demyelinating Polyneuropathy, Chronic Obstructive Pulmonary Disease (COPD), Cicatricial Pemphigoid, Cold Agglutinin Disease, CREST Syndrome, Crohn's Disease, Dego's Disease, Dermatomyositis, Dermatomyositis—Juvenile, Discoid Lupus, Essential Mixed Cryoglobulinemia, Fibromyalgia-Fibromyositis, Grave's Disease, Guillain-Barre, Hashimoto's Thyroiditis, Idiopathic Pulmonary Fibrosis, Idiopathic Thrombocytopenia Purpura (ITP), IgA Nephropathy, Insulin Dependent Diabetes (Type I), Type II diabetes, Juvenile Arthritis, Lupus, Meniere's Disease, Mixed connective Tissue Disease, Multiple Sclerosis, Myasthenia Gravis, Pemphigus Vulgaris, Pernicious Anemia, Polyarteritis Nodosa, Polychondritis, Polyglancular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Sderoderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo, Wegener's Granulomatosis, or any acute or chronic inflammation related to burning, surgery, injury, and allergy.

T-MSC can be differentiated into multiple cell lineages including, but not limited to, adipocytes, myoblast cells, neural lineage cells, osteoblast cells, fibroblasts, chondrocytes, and stromal cells. These cells derived from T-MSC (T-MSC-DL) can be used to treat multiple tissue injury, and can be used for tissue engineering, tissue repair, tissue regeneration purposes like, joint healing, tendon healing, connective tissue healing, neural lineage tissue and cells healing, fat tissue healing, bone healing, skin healing, other wound healing, muscle healing, cartilage healing, smooth muscle healing, myocardiac healing, epithelia tissue healing, ligament healing, stroma repair, etc.

Specifically, T-MSC can be differentiated into neural lineage cells, which can be used to treat many neural disease including but not limited to Agraphia, Alzheimer's disease, Amyotrophic lateral sclerosis, Aphasia, Apraxia, Arachnoiditis, Ataxia Telangiectasia, Attention deficit hyperactivity disorder, Auditory processing disorder, Autism, Alcoholism, Asperger's syndrome, Bipolar disorder, Bell's palsy, Brachial plexus injury, Brain damage, Brain injury, Brain tumor, Canavan disease, Capgras, Causalgia, Central pain syndrome, Central pontine myelinolysis, Centronudear myopathy, Cephalic disorder, Cerebral aneurysm, Cerebral arteriosclerosis, Cerebral atrophy, Cerebral gigantism, Cerebral palsy. Cerebral vasculitis, Cervical spinal stenosis, Charcot-Marie-Tooth disease, Chiari malformation, Chorea, Chronic fatigue syndrome, Chronic inflammatory demyelinating polyneuropathy (CIDP), Chronic pain, Coffin-Lowry syndrome, Coma, Complex regional pain syndrome, Compression neuropathy, Congenital facial diplegia, orticobasal degeneration, Cranial arteritis, Craniosynostosis, Creutzfeldt-Jakob disease, Cumulative trauma disorders, Cushing's syndrome, Cytomegalic inclusion body disease (CIBD), Cytomegalovirus Infection, Dandy-Walker syndrome, Dawson disease, De Morsier's syndrome, Dejerine-Klumpke palsy, Dejerine-Sottas disease, Delayed sleep phase syndrome, Dementia, Dermatomyositis, Developmental dyspraxia, Diabetic neuropathy, Diffuse sclerosis, Downs syndrome, Dravet syndrome, Dysautonomia, Dyscalculia, Dysgraphia, Dyslexia, Dystonia, Empty sella syndrome, Encephalitis, Encephalocele, Encephalotrigeminal angiomatosis, Encopresis, Epilepsy, Erb's palsy, Erythromelalgia, Essential tremor, Fabry's disease, Fahr's syndrome, Fainting, Familial spastic paralysis, Febrile seizures, Fisher syndrome, Friedreich's ataxia, Fibromyalgia, Foville's syndrome, Fetal Alcohol Effect, Gaucher's disease, Gerstmann's syndrome, Giant cell arteritis, Giant cell inclusion disease, Globoid Cell Leukodystrophy, Gray matter heterotopia, Guillain-Barré syndrome, HTLV-1 associated myelopathy. Hallervorden-Spatz disease, Head injury, Headache, Hemifacial Spasm. Hereditary Spastic Paraplegia, Heredopathia atactica polyneuritiformis, Herpes zoster oticus, Herpes zoster, Hirayama syndrome, Holoprosencephaly, Huntington's disease, Hydranencephaly, Hydrocephalus, Hypercortisolism, Hypoxia, Immune-Mediated encephalomyelitis, Inclusion body myositis, Incontinentia pigmenti, Infantile phytanic acid storage disease, Infantile Refsum disease, Infantile spasms, Inflammatory myopathy, Intracranial cyst, Intracranial hypertension, Joubert syndrome, Karak syndrome, Kearns-Sayre syndrome, Kennedy disease, Kinsbourne syndrome, Klippel Fell syndrome, Krabbe disease, Kugelberg-Welander disease, Lafora disease, Lambert-Eaton myasthenic syndrome, Landau-Kleffner syndrome, Lateral medullary (Wallenberg) syndrome, Learning disabilities, Leigh's disease, Lennox-Gastaut syndrome, Lesch-Nyhan syndrome, Leukodystrophy, Lewy body dementia, Lissencephaly, Locked-In syndrome, Lou Gehrig's disease (See amyotrophic lateral sclerosis), Lumbar disc disease, Lumbar spinal stenosis, Lyme disease—Neurological Sequelae, Machado-Joseph disease (Spinocerebellar ataxia type 3), Macrencephaly, Macropsia, Megalencephaly, Melkersson-Rosenthal syndrome, Menieres disease, Meningitis, Menkes disease, Metachromatic leukodystrophy, Microcephaly, Micropsia, Migraine, Miller Fisher syndrome, Mini-stroke (transient ischemic attack), Misophonia, Mitochondrial myopathy, Mobius syndrome, Monomelic amyotrophy, Motor Neurone Disease—see amyotrophic lateral sclerosis, Motor skills disorder, Moyamoya disease, Mucopolysaccharidoses, Multi-infarct dementia, Multifocal motor neuropathy, Multiple sclerosis, Multiple system atrophy, Muscular dystrophy, Myalgic encephalomyelitis, Myasthenia gravis, Myelinodastic diffuse sclerosis, Myocionic Encephalopathy of infants, Myoclonus, Myopathy, Myotubular myopathy, Myotonia congenita, Narcolepsy, Neurofibromatosis, Neuroleptic malignant syndrome, Neurological manifestations of AIDS. Neurological sequelae of lupus, Neuromyotonia, Neuronal ceroid lipofuscinosis, Neuronal migration disorders, Neurosis, Niemann-Pick disease, Non 24-hour sleep-wake syndrome, Nonverbal learning disorder, Naurological disorder, O'Sullivan-McLeod syndrome, Occipital Neuralgia, Occult Spinal Dysraphism Sequence, Ohtahara syndrome, Olivopontocerebellar atrophy, Opsoclonus myodonus syndrome, Optic neuritis, Orthostatic Hypotension, Otosderosis, Overuse syndrome, Palinopsia, Paresthesia, Parkinson's disease, Paramyotonia Congenita, Paraneoplastic diseases, Paroxysmal attacks, Parry-Romberg syndrome, Pelizaeus-Merzbacher disease, Periodic Paralyses, Peripheral neuropathy, Pervasive developmental disorders, Photic sneeze reflex, Phytanic acid storage disease, Pick's disease, Pinched nerve, Pituitary tumors, PMG, Polyneuropathy, Polio, Polymicrogyria, Polymyositis, Porencephaly, Post-Polio syndrome, Postherpetic Neuralgia (PHN), Postural Hypotension, Prader-Willi syndrome, Primary Lateral Sclerosis, Prion diseases, Progressive hemifacial atrophy, Progressive multifocal leukoencephalopathy, Progressive Supranuclear Palsy, Pseudotumor cerebri, Quadriplegia, Rabies, Ramsay Hunt syndrome type I, Ramsay Hunt syndrome type II, Ramsay Hunt syndrome type III—see Ramsay-Hunt syndrome. Rasmussen's encephalitis. Reflex neurovascular dystrophy, Refsum disease, Repetitive stress injury, Restless legs syndrome. Retrovirus-associated myelopathy, Rett syndrome, Reye's syndrome, Rhythmic Movement Disorder, Romberg syndrome, Saint Vitus dance, Sandhoff disease, Schilder's disease [disambiguation needed], Schizencephaly, Sensory integration dysfunction, Septo-optic dysplasia, Shaken baby syndrome, Shingles, Shy-Drager syndrome, Sjögren's syndrome, Sleep apnea, Sleeping sickness, Snatiation, Sotos syndrome, Spasticity, Spina bifida, Spinal cord injury, Spinal cord tumors, Spinal muscular atrophy, Spinocerebellar ataxia. Split-brain, Steele-Richardson-Olszewski syndrome, Stiff-person syndrome, Stroke, Sturge-Weber syndrome, Subacute sclerosing panencephalitis, Subcortical arteriosclerotic encephalopathy, Superficial siderosis, Sydenham's chorea, Syncope, Synesthesia, Syringomyelia, Tarsal tunnel syndrome, Tardive dyskinesia, Tardive dysphrenia, Tarlov cyst, Tay-Sachs disease, Temporal arteritis, Tetanus, Tethered spinal cord syndrome, Thomsen disease, Thoracic outlet syndrome, Tic Douloureux, Todd's paralysis, Tourette syndrome, Toxic encephalopathy, Transient ischemic attack, Transmissible spongiform encephalopathies, Transverse myelitis, Traumatic brain injury, Tremor, Trigeminal neuralgia, Tropical spastic paraparesis, Trypanosomiasis. Tuberous sclerosis, Ubisiosis, Template: Unipolar depression, Von Hippel-Lindau disease (VHL), Viliuisk Encephalomyelitis (VE), Wallenberg's syndrome, Werdnig-Hoffman disease, West syndrome, Whiplash, Williams syndrome, Wilson's disease.

5.17 Uses of T-MSC as Delivery Systems

Because it has been shown that the T-MSC of the present invention have the unique ability to cross the blood-brain barrier and the blood-spinal cord barrier, a further embodiment of the present invention is a method of using T-MSC for delivery of agents through the blood brain barrier and/or the blood spinal cord barrier, by attaching or conjugating the agent to the T-MSC to form a complex; and administering the T-MSC-agent complex to a subject, wherein the T-MSC cross the blood-brain and/or the blood-spinal cord barrier and deliver the agent to the central nervous system. The T-MSC may be in the form of a single cell, a cell culture, a solution or a pharmaceutical preparation. Agents would include but are not limited to chemicals, drugs, proteins, DNA, RNA, antibodies, and small molecules.

A further embodiment of the present invention is a delivery system for the delivery of agents through the blood brain barrier and/or the blood spinal cord barrier comprising T-MSC and an agent conjugated or attached to the T-MSC.

The ability to permeate the blood-brain barrier and the blood-spinal cord barrier would be useful in the treatment and prevention of diseases including but not limited to neurological disorders, multiple sclerosis, cancer, Parkinson's Disease, Alzheimer's Disease, Huntington's Disease, meningitis, encephalitis, rabies, epilepsy, dementia, Lyme's Disease, stroke, and amyotrophic lateral sclerosis, as well as brain and spinal cord injury. Thus, a subject in need thereof would have a disease or be at risk for a disease in which the blood-brain barrier and/or blood-spinal cord barrier is involved. Thus, a further embodiment of the present invention is a method of treating a disease or injury, by attaching or conjugating an agent to the T-MSC to form a complex; and administering the T-MSC-agent complex to a subject in need thereof, wherein the T-MSC cross the blood-brain and/or the blood-spinal cord barrier and deliver the agent to the central nervous system, and the agent is used as a treatment or prevention of the disease or injury of the subject. Since the T-MSC have strong migration ability and infiltration ability, it can also been used as carrier for tumor/cancer therapy to carry anti-tumor drugs and proteins. The T-MSC may be in the form of a single cell, a cell culture, a solution or a pharmaceutical preparation. Agents include, but are not limited to, chemicals, drugs, proteins, DNA, RNA, micro-RNA, non-coding RNA, antibodies, small molecules and/or nano particles.

Agents that are useful in the treatment and prevention of diseases include, but ARE not limited to, antibiotics, anti-viral agents, anti-fungal agents, steroids, chemotherapeutics, anti-inflammatories, cytokines, and/or synthetic peptides.

Proteins and peptides would also be useful to conjugate to the T-MSC and would include erythropoietin (EPO), anti-beta-amyloid peptides, tissue plasminogen activator (TPA), granulocyte colony stimulating factor (G-CSF), interferon (IFN), growth factor/hormone, anti-VEGF peptides, anti-TNF peptides, NGF, HGF, IL-2, CX3CL1, GCV, CPT-11, cytosine deaminase, HSV-TK, carboxylesterase, oncolytic virus, TSP-1, TRAIL, FASL, IL-10, and TGFb. Proteins and peptides that bind to particular receptors and block these receptors would also be useful and are contemplated by the current invention to be attached to the T-MSCs.

DNA and RNA that coded for therapeutic proteins and peptide would also be useful to conjugate to the T-MSC for delivery across the blood-brain barrier and/or the blood-spinal cord barrier.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Any agent that would block the activation, expression and/or action of a molecule or the receptor of the molecule in the pathway related to any disease in which crossing the blood-brain barrier and/or blood-spinal cord barrier is useful could be attached or conjugated to the T-MSCs. Such agents include but are not limited to chemicals, phytochemicals, pharmaceuticals, biologics, small organic molecules, antibodies, nucleic acids, peptides, and proteins.

Inhibiting a pathway can also be effected using "decoy" molecules which mimic the region of a target molecule in the pathway binds and activates. The activating molecule would bind to the decoy instead of the target, and activation could not occur.

Inhibition can also be effected by the use of a "dominantly interfering" molecule, or one in which the binding portion of activating molecule is retained but the molecule is truncated so that the activating domain is lacking. These molecules would bind to receptors in the pathway but be unproductive and block the receptors from binding to the activating molecule. Such decoy molecules and dominantly interfering molecule can be manufactured by methods known in the art, and attached or conjugated to the T-MSC for delivery across the blood-brain or blood-spinal cord barrier.

A method for delivery of agents across the blood-brain and/or blood-spinal cord barrier is also useful for diagnostic agents, including but not limited to chemicals, antibodies, peptides, proteins, DNA, and RNA. Such agents in order to be useful for diagnosis must have a means of being visualized and/or quantified. Such means include, but are not limited to, fluorescence, biomarkers, dyes, radioactive isotypes labels and/or nanoparticles.

Such a method for delivery and a delivery system would be useful for the diagnosis of neurological disorders, multiple sclerosis, cancer, Parkinson's Disease, Alzheimer's Disease, Huntington's Disease, meningitis, encephalitis, rabies, epilepsy, dementia, Lyme's Disease, stroke, and amyotrophic lateral sclerosis, as well as brain and spinal cord injury. Thus, a further embodiment of the present invention is a method of diagnosing a disease or injury, by attaching or conjugating the agent to the T-MSC to form a complex; and administering the T-MSC-agent complex to a subject in which a disease is suspected, wherein the T-MSC cross the blood-brain and/or the blood-spinal cord barrier and deliver the agent to the central nervous system. The T-MSC may be in the form of a single cell, a cell culture, a solution or a pharmaceutical preparation. Agents would include but are not limited to chemicals, drugs, proteins, DNA, RNA, antibodies, and small molecules.

Agents, no matter the type and whether for treatment, prevention, or diagnosis, can be conjugated or attached to the T-MSC by any method known in the art including, but not limited to, synthetic extracellular matrix, alginate-poly-L-Lysine encapsulate and/or container.

In certain embodiments, large scale production at industrial level of manufacturing is included in the present disclosure, methods of which are well known in the art. In certain embodiments, the large scale production includes the use of a Hyper-STACK 2D culture system and/or a Microcarrier 3D bioreactor.

6. EXAMPLES

Example 1. Derivation of T-MSC

Material and Methods

The following reagents and materials were obtained from the below-described sources:

Customed mTeSR1 Medium: Stem Cell Technology, Inc.
BMP4: Stemgent or other vendors
SB431542: Cayman Chemical or other vendors
A83-01: Stemgent or other vendors.
ALK5 inhibitor: Stemgent or other Vendors
DMEM/F12: GIBCO Life Technologies
alpha-MEM: GIBCO Life Technologies
Fetal Bovine Serum: GIBCO Life Technologies or other vendors CT2 hESC line derived at the University of Connecticut Stem Cell Core was cultured for two passages on irradiated mouse embryonic fibroblast (MEF) as feeders. The hESCs were then split on plates coated with Matrigel (BD Biosciences, San Jose, Calif.) and cultured in mTeSR1 (Ludwig et al., 2006) (Stem Cell Technologies, Vancouver, Canada). ESI-017, ESI-051, ESI-053, ESI-049, and ESI-35 human embryonic stem cells were purchased from BioTime, Inc. (CA).

Derivation of T-MSC

As shown in FIG. 1, hESCs at ~80% confluency on the Matrigel-coated plates were digested with Dispase at 1 mg/ml for 5-10 min. The cells were then washed with mTESR1 medium once and split as small dumps or single cells onto Matrigel-coated plate and cultured in mTeSR1 for 12 hr. Then the culture medium was replaced by a trophoblast-formation medium containing BMP4 (2-100 ng/ml), or optional A83-01 (0.1-1 µM). After culture for 48-72 hr, the cells changed from hESC-like morphology into trophoblast-like morphology featured by flat, enlarged cell size, small nuclear/cytosol ratio, and diffuse cell borders. The cells were digested with TrypLE and washed with MSC growth medium (alpha-MEM containing 20% fetal bovine serum and non-essential amino acids). The cells were then plated onto Matrigel-coated plates at a density of 5,000 cells/cm$^2$. The medium was changed after 24 hr, and then changed every 3-4 days. After 6 more days, the cells were differentiated into spindle-like cells similar to the morphology of typical MSCs. Morphology of Day2 Trophoblast are shown in FIG. 2A, morphology of Day 5 pre-T-MSC are shown in FIG. 2B, morphology of T-MSC are shown in FIG. 2C.

Derivation of HB-MSC

CT2 hESC cells were differentiated into EB cells and then enriched for HB as previously described (Lu et al., 2008): Lu et al., 2007)). 50-80% confluent hEC cell on the Matrigel plate were digested with Dispase (1 mg/ml for 5 to 10 minutes) and then washed with EB formation basal medium, HPGM (Lonza, Walksville, Md.), or STEMLINE I/II Hematopoietic Stell Cell Expansion Medium (Sigma, St. Louis, Mo.), or StemSpan H3000 (Stem Cell Technologies, Vancouver, Canada), or IMDM with 10% FBS, or DMEDM/F12 with 10% FBS. Cells were then cultured in EB formation medium supplemented with 50 ng/ml of VEGF (Peprotech) and 50 ng/ml of BMP4 (Stemgent) for 48 hours on ultra-low plate at a density of about 2-3 million cells/mi. After 48 hours, half the culture medium was replaced with fresh EB formation medium plus 25-50 ng/ml of bFGF.

Four days later, EB cells formed in the medium were harvested and dissociated into single cells with TrypLE (Invitrogen) at 37° C. for 2-3 minutes. Cells were washed and resuspended at 1-5 million cells/ml in EB formation basal medium. The single cell suspension was then mixed at 1:10 with Hemangioblast Growth Medium (Stem Cell Technologies, Vancouver, Canada).

Blast cell growth medium (BGM) were made as follows: To 100 ml Serum-free methylcellulose CFU medium (Stem Cell Technologies, H4436 or H4536), added with VEGF, TPO and FLT3-Ligand to 50 ng/ml, bFGF to 20-50 ng/ml, 1 ml of EX-CYTE Growth Enhancement Media Supplement and 1 ml of Pen/Strap, mix well.

The mixtures were vortexed and plated onto ultralow plates by passing through a 16 G needle and cultured for 5-9 days at 37° C. with 5% $CO_2$.

Single cells were then re-suspended in MSC medium containing: 1) 10-20% FBS in alpha-MEM (Invitrogen) or 2) 10-20% KOSR alpha-MEM, 3) 10-20% FBS DMEM high-glucose, or 4) 10-20% KOSR DMEM high-glucose, and cultured on either Matrigel, gelatin, vitronectin, laminin, fibronectin, or collagen I coated plates at a density of 100-5,000 cell/cm². The medium was changed after 24 hours and refreshed every 2-4 days. After 6-12 days the cells gradually differentiated into spindle-like cells similar to typical MSCs.

Derivation of MSC Through SB431542

This method was published previously (Chen et al., 2012).

Results

It was found that the method generated T-MSC that have superior efficiency, yield and purity. As shown in the bottom panel of FIG. 1, on Day 10, T-MSC already generated >90% purify of MSC with 10 fold cell number increase, whereas other methods either did not have any MSC or only had very low purity of MSCs. On Day20, T-MSC already had 3000 fold expansion with >99% purity of MSCs, whereas the other methods only expanded 20 fold at most. By day 30, 0.1 million of hESC generated 50 billion of T-MSC, that is a 500,000 fold expansion of the original hESCs, whereas the other methods only expanded 3000 fold at most.

Example 2. Characterization of T-MSC Cells

The T-MSC cells obtained in Example 1 were further analyzed using flow cytometry immunofluorescence staining.

Materials and Methods

Flow cytometry staining was used to characterize the T-MSCs. Cells were washed and blocked with 2% BSA in PBS, and stained with antibodies for various cell surface markers Trop-2 (Trp-2, eBioscience), CD31. CD34, CD29. CD73, CD90, CD105, CD44, CD45, CD146, CD166, HLA-ABC, HLA-DR, HLA-G (BD Bioscience or eBioscience) by following the manufacturers' instructions. Data were collected on FACS LSR II Flow Cytometer using FACSDiva software (BD Bioscience). Post-acquisition analysis was performed with the FlowJo software (Treestar).

Results

The attached cells obtained from Day 2 trophoblast, Day 5 pre-T-MSC and Day 9 T-MSC were stained with CD73 and Trop-2. The trophoblast cells only expressed high levels of Trop-2 (greater than 95%), but less than 1% of CD73 (FIG. 3A); the pre-T-MSC at day 5 has more than 50% of cells express both Trop-2 and CD73, 40% of the cells express only CD73 (FIG. 3B); T-MSC at day 9 of hESC differentiation has less than 1% of the cells express Trop-2, and 99% of cells express only CD73 (FIG. 3C).

Further characterization of the T-MSC by FACS staining of multiple cell surface markers show T-MSC express <3% of Trop-2, <1% of CD31, CD34. >99% of CD73, >95% of CD90, >90% of CD105, >99% of CD44 and >80% of CD29 (FIGS. 4 A-H).

Example 3. T-MSCs have a Stronger Inhibition on T Cell Functions In Vitro than BM-MSC hEs-MSCs and BM-MSCs were compared for their ability to inhibit T cell proliferation in vitro following antigen stimulation.

Materials and Methods

Culture of BM-MSCs

BM-MSCs were derived from BM mononuclear cells (BMMNCs) or obtained from AllCells, Inc. (Alameda) and Lonza (Basel, Switzerland) BMMNCs. For derivation, BMMNCs were thawed and plated onto tissue culture plastic dishes in ☐MEM+20% FBS. Adherent cells began to appear within the first 4-5 days and fed every 3 days until day ~10-12, when cells were harvested and replated at 3,000-5,000 cells/cm².

The in vitro assay for T cell proliferation was performed using lymphocytes isolated from mouse peripheral lymph nodes. These lymphocytes were labeled with 5 µM of carboxyfluorescein succinimidyl ester (CFSE) to track their proliferation by monitoring CFSE dilution in their daughter cells, for 10 minutes at 37° C. 10,000 T-MSCs or BM-MSCs were mixed with 100,000 lymphocytes per well in a 96-well plate, and the cells were stimulated for proliferation with plate-bound anti-CD3 (at 0.3, 1 µg/ml) and soluble anti-CD28 antibodies (1 µg/ml, eBioscience, CA). The cells were collected 3 days after the stimulation, followed by FACS staining with anti-CD4 and anti-CD8 antibodies (BD Bioscience, CA). CFSE dilution was gated on CD4+ and CD8+ T cells, respectively.

Results

Using the in vitro assay with mouse lymphocytes, it was found T-MSCs inhibited the proliferation of mouse CD4+ and CD8+ T cells when stimulated with anti-CD3 antibody at 0.3 and 1 µg/ml, whereas BM-MSC only did so when the T cells were stimulated with anti-CD3 antibody at low doses, i.e., 0.3 µg/ml (FIG. 5)

Example 4. T-MSCs Attenuate the Disease Score of EAE Mice

Because it has been shown that BM-MSCs can attenuate the disease progression of the mouse model of multiple sclerosis, experimental autoimmune encephalomyelitis (EAE), the T-MSCs obtained in Example 1 were injected into mice with EAE to determine if they would have the same effect.

Materials and Methods

Derivation of MSC through SB431542: the MSC derived from this method will be called hES-MSC(SB), This Method was published previously (Chen et al., 2012).

The mouse EAE model was induced as previously described (Stromnes and Goverman, 2006). C57BL/6 mice were subcutaneously injected with a mixture of myelin oligodendrocyte glycoprotein peptide 35-55 ($MOG^{35\text{-}55}$), Freund's adjuvant, and pertussis toxin contained in the EAE Induction Kit (Hooke Laboratories, Inc, MA. (Cat. #EK-0114)) following the manufacturer's protocol and as described in Ge et al. (2012).

BM-MSC, T-MSC or hES-MSC(SB) at $10^6$ cells/mouse or PBS (a vehicle control) was intraperitoneal (i.p.) injected on day 6 (for pre-onset) or 18 (for post-onset) after the immunization. The disease score was monitored on the mice every day for up to 31 days.

The disease scoring system is as follows:
0: no sign of disease;
1: loss of tone in the tail;
2: partial hind limb paralysis;
3: complete hind limb paralysis;
4: front limb paralysis; and
5: moribund
(Stromnes and Goverman, 2006).

Results

As shown in FIG. 6, the T-MSCs significantly attenuated the daily disease scores when injected at 6 days or pre-onset of disease, showing a prophylactic effect of the T-MSCs. Mice injected with BM-MSC did not attenuate the disease score, hES-MSC(SB) had a partial effect in attenuating the disease score but not as good as T-MSC.

Example 5. Multi-Lineage Differentiation of T-MSC

Materials and Methods

Osteogenesis, Chondrogenesis and Adipogenesis of T-MSC

STEMPRO Osteogenesis and Chondrogenesis Differentiation Kits (Invitrogen, Grand Island, N.Y.) were used for osteogenesis and chondrogenesis, and the Hyclone AdvanceSTEM Adipogenic Differentiation kit (Thermo Scientific, Logan, Utah) for adipogenesis, following the manufacturers' instructions.

Results

As shown in FIG. 7. T-MSC had good potency in differentiating into all the 3 lineages of mesoderm tissues, osteoblasts, chondrocyte and adipocytes. Thus, T-MSC can be used as source for tissue regeneration, tissue engineering and tissue repair.

Example 6. T-MSC are Different from hES-HB-MSC and BM-MSC

Microarray analysis was performed to compare the gene expression profile of T-MSC, hES-HB-MSC and BM-MSCs.

Materials and Methods

For microarray analysis, RNA of hES-MSC at passages 2-4 or BM-MSC at passage 3 were harvested with Trizol (Invitrogen, CA) following the manufacturer's protocol. The HumanHT-12 v4 Expression BeadChip (Illumina, San Diego, Calif.) was used to analyze the gene expression profile of the cells. Data were analyzed using Genome Studio V2011.1. Two BM-MSC cell lines from different sources were used, and two hES-MSC cell lines, derived from H9 and MA09, were used.

Results

As shown in FIG. 8, the overall expressional profiles of some key cytokines, transcription factors, cell surface markers are very different between these 3 different MSCs. T-MSC may play different roles in immunosuppression and tissue regeneration.

REFERENCES

Al Jumah, M. A., and Abumaree, M. H. (2012). The Immunomodulatory and Neuroprotective Effects of Mesenchymal Stem Cells (MSCs) in Experimental Autoimmune Encephalomyelitis (EAE): A Model of Multiple Sclerosis (MS). International journal of molecular sciences 13, 9298-9331.

Anton, K., Banerjee, D., and Glod, J. (2012). Macrophage-associated mesenchymal stem cells assume an activated, migratory, pro-inflammatory phenotype with increased IL-6 and CXCL10 secretion. PLoS One 7, e35036.

Auletta, J. J., Bartholomew, A. M., Maziarz, R. T., Deans, R. J., Miller, R. H., Lazarus, H. M., and Cohen, J. A. (2012). The potential of mesenchymal stromal cells as a novel cellular therapy for multiple sclerosis. Immunotherapy 4, 529-547.

Barbed, T., Willis, L. M., Socci, N. D., and Studer, L. (2005). Derivation of multipotent mesenchymal precursors from human embryonic stem cells. PLoS Med 2, e161.

Barry, F., Boynton, R. E., Liu, B., and Murphy, J. M. (2001). Chondrogenic differentiation of mesenchymal stem cells from bone marrow: differentiation-dependent gene expression of matrix components. Exp Cell Res 268, 189-200.

Becher B, Durell B G, Noelle R J (2002) Experimental autoimmune encephalitis and inflammation in the absence of interleukin-12. The Journal of clinical investigation 110: 493-497.

Benito-Leon, J. (2011). Are the prevalence and incidence of multiple sclerosis changing? Neuroepidemiology 36, 148-149.

Brown, S. E., Tong, W., and Krebsbach, P. H. (2009). The derivation of mesenchymal stem cells from human embryonic stem cells. Cells Tissues Organs 189, 256-260.

Chao, Y. X., He, B. P., and Tay, S. S. (2009). Mesenchymal stem cell transplantation attenuates blood brain barrier damage and neuroinflammation and protects dopaminergic neurons against MPTP toxicity in the substantia nigra in a model of Parkinson's disease. Journal of Neuroimmunology 216, 39-50.

Chaudhary P. Marracci G H, Bourdette D N (2006) Lipoic acid inhibits expression of ICAM-1 and VCAM-1 by CNS endothelial cells and T cell migration into the spinal cord in experimental autoimmune encephalomyelitis. Journal of neuroimmunology 175: 87-96.

Chen, Y. S., Pelekanos, R. A., Ellis, R. L., Horne, R., Wolvetang, E. J., and Fisk, N. M. (2012). Small Molecule Mesengenic Induction of Human Induced Pluripotent Stem Cells to Generate Mesenchymal Stem/Stromal Cells. Stem Cells Translational Medicine.

Chyou, S., Ekland, E. H., Carpenter, A. C., Tzeng, T. C., Tian, S., Michaud, M., Madri, J. A., and Lu, T. T. (2008). Fibroblast-type reticular stromal cells regulate the lymph node vasculature. J Immunol 181, 3887-3896.

Connick, P., Kolappan, M., Crawley, C., Webber, D. J., Patani, R., Michell, A. W., Du, M. Q., Luan, S. L., Altmann, D. R., Thompson, A. J., et al. (2012). Autologous mesenchymal stem cells for the treatment of secondary progressive multiple sclerosis: an open-label phase 2a proof-of concept study. Lancet neurology 11, 150-156.

Correale, J., and Villa, A. (2007). The blood-brain-barrier in multiple sclerosis: functional roles and therapeutic targeting. Autoimmunity 40, 148-160.

Costa, M., Dottori, M., Ng, E., Hawes, S. M., Sourris, K., Jamshidi, P., Pera, M. F., Elefanty, A. G., and Stanley, E. G. (2005). The hESC line Envy expresses high levels of GFP in all differentiated progeny. Nat Methods 2, 259-260.

Crocker, S. J., Milner, R., Pham-Mitchell, N., and Campbell, I. L. (2006). Cell and agonist-specific regulation of genes for matrix metalloproteinases and their tissue inhibitors by primary glial cells. Journal of neurochemistry 98, 812-823.

Cuccurullo C, Iezzi A, Fazia M L, De Cesare D, Di Francesco A, et al. (2006) Suppression of RAGE as a basis of simvastatin-dependent plaque stabilization in type 2 diabetes. Arteriosclerosis, thrombosis, and vascular biology 26: 2716-2723.

Cunnea P, McMahon J, O'Connell E, Mashayekhi K, Fitzgerald U, et al. (2010) Gene expression analysis of the microvascular compartment in multiple sclerosis using laser microdissected blood vessels. Acta neuropathologica 119: 601-615.

Dai H, Ciric B, Zhang G X, Rostami A (2012) Interleukin-10 µlays a crucial role in suppression of experimental autoimmune encephalomyelitis by Bowman-Birk inhibitor. Journal of neuroimmunology 245: 1-7.

Dienz, O., and Rincon, M. (2009). The effects of IL-6 on CD4 T cell responses. Clinical immunology 130, 27-33.

Djouad, F., Plence, P., Bony, C., Tropel, P., Apparailly, F., Sany, J., Noel, D., and Jorgensen, C. (2003). Immunosuppressive effect of mesenchymal stem cells favors tumor growth in allogeneic animals. Blood 102, 3837-3844.

Dong, C. (2008). TH17 cells in development: an updated view of their molecular identity and genetic programming. Nat Rev Immunol 8, 337-348.

Draper, J. S., Pigott. C., Thomson, J. A., and Andrews, P. W. (2002). Surface antigens of human embryonic stem cells: changes upon differentiation in culture. Journal of anatomy 200, 249-258.

Drukker, M., Katchman, H., Katz, G., Even-Tov Friedman, S., Shezen, E., Hornstein, E., Mandelboim, O., Reisner, Y., and Benvenisty, N. (2006). Human embryonic stem cells and their differentiated derivatives are less susceptible to immune rejection than adult cells. Stem Cells 24, 221-229.

Drukker, M., Katz, G., Urbach, A., Schuldiner, M., Markel, G., Itskovitz-Eldor, J., Reubinoff, B., Mandelboim, O., and Benvenisty, N. (2002). Characterization of the expression of MHC proteins in human embryonic stem cells. Proceedings of the National Academy of Sciences of the United States of America 99, 9864-9869.

English, K., Barry, F. P., Field-Corbett, C. P., and Mahon, B. P. (2007). IFN-gamma and TNF alpha differentially regulate immunomodulation by murine mesenchymal stem cells. Immunol Lett 110, 91-100.

Ge, S., Shrestha, B., Paul, D., Keating, C., Cone, R., Guglielmotti, A., and Pachter, J. S. (2012). The CCL2 synthesis inhibitor bindarit targets cells of the neurovascular unit, and suppresses experimental autoimmune encephalomyelitis. J Neuroinflammation 9, 171.

Gijbels, K., Brocke, S., Abrams, J. S., and Steinman, L. (1995). Administration of neutralizing antibodies to interleukin-6 (IL-6) reduces experimental autoimmune encephalomyelitis and is associated with elevated levels of IL-6 bioactivity in central nervous system and circulation. Mol Med 1, 795-805.

Gordon, D., Pavlovska, G., Glover, C. P., Uney, J. B., Wraith, D., and Scolding, N. J. (2008a). Human mesenchymal stem cells abrogate experimental allergic encephalomyelitis after intraperitoneal injection, and with sparse CNS infiltration. Neurosci Lett 448, 71-73.

Gordon, D., Pavlovska, G., Glover, C. P., Uney, J. B., Wraith, D., and Scolding, N. J. (2008b). Human mesenchymal stem cells abrogate experimental allergic encephalomyelitis after intraperitoneal injection, and with sparse CNS infiltration. Neuroscience letters 448, 71-73.

Gordon, D., Pavlovska, G., Uney, J. B., Wraith, D. C., and Scolding, N. J. (2010). Human mesenchymal stem cells infiltrate the spinal cord, reduce demyelination, and localize to white matter lesions in experimental autoimmune encephalomyelitis. J Neuropathol Exp Neurol 69, 1087-1095.

Grinnemo, K. H., Mansson, A., Dellgren, G., Klingberg, D., Wardell, E., Drvota, V., Tammik, C., Holgersson, J., Ringden, O., Sylven, C., et al. (2004). Xenoreactivity and engraftment of human mesenchymal stem cells transplanted into infarcted rat myocardium. J Thorac Cardiovasc Surg 127, 1293-1300.

Hansen, W., Westendorf, A. M., and Buer, J. (2008). Regulatory T cells as targets for immunotherapy of autoimmunity and inflammation. Inflamm Allergy Drug Targets 7, 217-223.

Hofstetter, C. P., Schwarz, E. J., Hess, D., Widenfalk, J., El Manira, A., Prockop, D. J., and Olson, L. (2002). Marrow stromal cells form guiding strands in the injured spinal cord and promote recovery. Proceedings of the National Academy of Sciences of the United States of America 99, 2199-2204.

Huber, T. L., Kouskoff, V., Fehling, H. J., Palis, J., and Keller, G. (2004). Haemangioblast commitment is initiated in the primitive streak of the mouse embryo. Nature 432, 625-630.

Hwang, N. S., Varghese, S., Lee, H. J., Zhang, Z., Ye, Z., Bae, J., Cheng, L., and Elisseeff, J. (2008). In vivo commitment and functional tissue regeneration using human embryonic stem cell derived mesenchymal cells. Proc Natl Acad Sci USA 105, 20641-20646.

Huss D J, Winger R C, Cox G M, Guerau-de-Arellano M, Yang Y, et al. (2011) TGF-beta signaling via Smad4 drives IL-10 production in effector Th1 cells and reduces T-cell trafficking in EAE. European journal of immunology 41: 2987-2996.

Javazon, E. H., Beggs, K. J., and Flake, A. W. (2004). Mesenchymal stem cells: paradoxes of passaging. Exp Hematol 32, 414-425.

Johnston, J., and So, T. Y. (2012). First-line disease-modifying therapies in paediatric multiple sclerosis: a comprehensive overview. Drugs 72, 1195-1211

Karlsson, C., Emanuelsson, K., Wessberg, F., Kajic, K., Axell, M. Z., Eriksson, P. S., Lindahl, A., Hylner, J., and Strehl, R. (2009). Human embryonic stem cell-derived mesenchymal progenitors-Potential in regenerative medicine. Stem Cell Res 3, 39-50.

Karussis, D., Karageorgiou, C., Vaknin-Dembinsky, A., Gowda-Kurkalli, B., Gomori, J. M., Kassis, I., Bulte, J. W., Petrou, P., Ben-Hur, T., Abramsky, O., et al. (2010). Safety and immunological effects of mesenchymal stem cell transplantation in patients with multiple sclerosis and amyotrophic lateral sclerosis. Arch Neurol 67, 1187-1194.

Klimanskaya, I., Chung, Y., Becker, S., Lu, S. J., and Lanza, R. (2006). Human embryonic stem cell lines derived from single blastomeres. Nature 444, 481-485.

Kurtzke J F (1983). "Rating neurologic impairment in multiple sclerosis: an expanded disability status scale (EDSS)". Neurology 33 (11): 1444-52

Leech, M. D., Barr, T. A., Turner, D. G., Brown, S., O'Connor, R. A., Gray, D., Mellanby, R. J., and Anderton, S. M. (2012). Cutting Edge: IL-6-Dependent Autoimmune Disease: Dendritic Cells as a Sufficient, but Transient, Source. J Immunol.

Lin, G., Martins-Taylor, K., and Xu, R. H. (2010). Human embryonic stem cell derivation, maintenance, and differentiation to trophoblast. Methods in molecular biology 636, 1-24.

Liu, R., Zhang, Z., Lu, Z., Borlongan, C., Pan, J., Chen, J., Qian, L., Liu, Z., Zhu, L., Zhang, J., et al. (2012). Human Umbilical Cord Stem Cells Ameliorate Experimental Autoimmune Encephalomyelitis by Regulating Immunoinflammation and Remyelination. Stem cells and development.

Liu, Y., Goldberg, A. J., Dennis, J. E., Gronowicz, G. A., and Kuhn, L. T. (2012). One-step derivation of mesenchymal stem cell (MSC)-like cells from human pluripotent stem cells on a fibrillar collagen coating. PLoS One 7, e33225.

Lu, S. J., Feng, Q., Caballero, S., Chen, Y., Moore, M A., Grant, M. B., and Lanza, R. (2007). Generation of functional hemangioblasts from human embryonic stem cells. Nat Methods 4, 501-509.

Lu, S. J., Ivanova, Y., Feng, Q., Luo, C., and Lanza, R. (2009). Hemangioblasts from human embryonic stem cells generate multilayered blood vessels with functional smooth muscle cells. Regenerative medicine 4, 37-47.

Lu, S. J., Luo, C., Holton, K., Feng, Q., Ivanova, Y., and Lanza, R. (2008). Robust generation of hemangioblastic progenitors from human embryonic stem cells. Regen Med 3, 693-704.

Ludwig, T. E., Levenstein, M. E., Jones, J. M., Berggren, W. T., Mitchen, E. R., Frane, J. L., Crandall, L. J., Daigh, C. A., Conard, K. R., Piekarczyk, M. S., et al. (2006). Derivation of human embryonic stem cells in defined conditions. Nat Biotechnol 24, 185-187.

Mahad, D. J., and Ransohoff, R. M. (2003). The role of MCP-1 (CCL2) and CCR2 in multiple sclerosis and experimental autoimmune encephalomyelitis (EAE). Semin Immunol 15, 23-32.

McFarland, H. F., and Martin, R. (2007). Multiple sclerosis: a complicated picture of autoimmunity. Nat Immunol 8, 913-919.

Menge, T., Zhao, Y., Zhao, J., Wataha, K., Gerber, M., Zhang, J., Letoumeau, P., Redell, J., Shen, L., Wang, J., et al. (2012). Mesenchymal Stem Cells Regulate Blood-Brain Barrier Integrity Through TIMP3 Release After Traumatic Brain Injury. Science translational medicine 4, 161ra150.

Minagar, A., Maghzi, A. H., McGee, J. C., and Alexander, J. S. (2012). Emerging roles of endothelial cells in multiple sclerosis pathophysiology and therapy. Neurological research 34, 738-745.

Mohyeddin Bonab, M., Yazdanbakhsh, S., Lotfi, J., Alimoghaddom, K., Talebian, F., Hooshmand, F., Ghavamzadeh, A., and Nikbin, B. (2007). Does mesenchymal stem cell therapy help multiple sclerosis patients? Report of a pilot study. Iranian journal of immunology: IJI 4, 50-57.

Moore, C. S., Milner, R., Nishiyama, A., Frausto, R. F., Serwanski, D. R., Pagarigan, R. R., Whitton, J. L., Miller, R. H., and Crocker, S. J. (2011). Astrocytic tissue inhibitor of metalloproteinase-1 (TIMP-1) promotes oligodendrocyte differentiation and enhances CNS myelination. The Journal of neuroscience: the official journal of the Society for Neuroscience 31, 6247-6254.

Morando, S., Vigo, T., Esposito, M., Casazza, S., Novi, G., Principato, M. C., Furlan, R., and Uccelli, A. (2012). The therapeutic effect of mesenchymal stem cell transplantation in experimental autoimmune encephalomyelitis is mediated by peripheral and central mechanisms. Stem Cell Res Ther 3, 3.

Ohtaki, H., Ylostalo, J. H., Foraker, J. E., Robinson, A. P., Reger, R. L., Shioda, S., and Prockop, D. J. (2008). Stem/progenitor cells from bone marrow decrease neuronal death in global ischemia by modulation of inflammatory/immune responses. Proc Natl Acad Sci USA 105, 14638-14643.

Olivier, E. N., Rybicki, A. C., and Bouhassira, E. E. (2006). Differentiation of human embryonic stem cells into bipotent mesenchymal stem cells. Stem Cells 24, 1914-1922.

Patanella, A. K., Zinno, M., Quaranta, D., Nociti, V., Frisullo, G., Gainotti, G., Tonali, P. A., Batocchi, A. P., and Marra, C. (2010). Correlations between peripheral blood mononuclear cell production of BDNF, TNF-alpha, IL-6, IL-10 and cognitive performances in multiple sclerosis patients. J Neurosci Res 88, 1106-1112.

Payne, N. L., Sun, G., McDonald, C., Layton, D., Moussa, L., Emerson-Webber, A., Veron, N., Siatskas, C., Herszfeld, D., Price, J., et al. (2012). Distinct immunomodulatory and migratory mechanisms underpin the therapeutic potential of human mesenchymal stem cells in autoimmune demyelination. Cell Transplant.

Peron, J. P., Jazedje, T., Brandao, W. N., Perin, P. M., Maluf, M., Evangelista, L. P., Halpem, S., Nisenbaum, M. G., Czeresnia, C. E., Zatz, M., et al. (2012). Human endometrial-derived mesenchymal stem cells suppress inflammation in the central nervous system of EAE mice. Stem Cell Rev 8, 940-952.

Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.

Pomper, M. G., Hammond, H., Yu, X., Ye, Z., Foss, C. A., Lin, D. D., Fox, J. J., and Cheng, L. (2009). Serial imaging of human embryonic stem-cell engraftment and teratoma formation in live mouse models. Cell Res 19, 370-379.

Quintana, A., Muller, M., Frausto, R. F., Ramos, R., Getts, D. R., Sanz, E., Hofer, M. J., Krauthausen, M., King, N. J., Hidalgo, J., et al. (2009). Site-specific production of IL-6 in the central nervous system retargets and enhances the inflammatory response in experimental autoimmune encephalomyelitis. Journal of immunology 183, 2079-2088.

Rafei, M., Birman, E., Fomer, K., and Galipeau, J. (2009a). Allogeneic mesenchymal stem cells for treatment of experimental autoimmune encephalomyelitis. Mol Ther 17, 1799-1803.

Rafei, M., Campeau, P. M., Aguilar-Mahecha, A., Buchanan, M., Williams, P., Birman, E., Yuan, S., Young, Y. K., Boivin, M. N., Fomer, K., et al. (2009b). Mesenchymal stromal cells ameliorate experimental autoimmune encephalomyelitis by inhibiting CD4 Th17 T cells in a CC chemokine ligand 2-dependent manner. J Immunol 182, 5994-6002.

Rochman, I., Paul, W. E., and Ben-Sasson, S. Z. (2005). IL-6 increases primed cell expansion and survival. Journal of immunology 174, 4761-4767.

Ryan, J. M., Barry, F., Murphy, J. M., and Mahon, B. P. (2007). Interferon-gamma does not break, but promotes the immunosuppressive capacity of adult human mesenchymal stem cells. Clin Exp Immunol 149, 353-363.

Sanchez, L., Gutierrez-Aranda, I., Ligero, G., Rubio, R., Munoz-Lopez, M., Garcia-Perez, J. L., Ramos, V., Real, P. J., Bueno, C., Rodriguez, R., et al. (2011). Enrichment of human ESC-derived multipotent mesenchymal stem cells with immunosuppressive and anti-inflammatory properties capable to protect against experimental inflammatory bowel disease. Stem cells (Dayton, Ohio) 29, 251-262.

Sethe, S., Scutt, A., and Stolzing, A. (2006). Aging of mesenchymal stem cells. Ageing Res Rev 5, 91-116.

Solchaga, L. A., Penick, K. J., and Welter, J. F. (2011). Chondrogenic differentiation of bone marrow-derived mesenchymal stem cells: tips and tricks. Methods in molecular biology 698, 253-278.

Stromnes, I. M., and Goverman, J. M. (2006). Active induction of experimental allergic encephalomyelitis. Nat Protoc 1, 1810-1819.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science 282, 1145-1147.

Tse, W. T., Pendleton, J. D., Beyer, W. M., Egalka, M. C., and Guinan, E. C. (2003). Suppression of allogeneic T-cell proliferation by human marrow stromal cells: implications in transplantation. Transplantation 75, 389-397.

Tyndall, A. (2011). Successes and failures of stem cell transplantation in autoimmune diseases. Hematology Am Soc Hematol Educ Program 2011, 280-284.

Uccelli A, Prockop D J (2010a). Why should mesenchymal stem cells (MSCs) cure autoimmune diseases? Curr Opin Immunol 22: 768-774.

Uccelli, A., and Prockop, D. J. (2010b). Why should mesenchymal stem cells (MSCs) cure autoimmune diseases? Curr Opin Immunol, 7.

Waterman, R. S., Tomchuck, S. L., Henkle, S. L., and Betancourt, A. M. (2010). A new mesenchymal stem cell (MSC) paradigm: polarization into a pro-inflammatory MSC1 or an Immunosuppressive MSC2 phenotype. PLoS One 5, e10088.

Weber, M. S., Menge, T., Lehmann-Horn, K., Kronsbein, H. C., Zett, U., Sellner, J., Hemmer, B., and Stuve, O. (2012). Current treatment strategies for multiple sclerosis—efficacy versus neurological adverse effects. Current pharmaceutical design 18, 209-219.

Wong, R. S. (2011). Mesenchymal stem cells: angels or demons? J Biomed Biotechnol 2011, 459510.

Xu, R. H., Chen, X., Li, D. S., Li, R., Addicks, G. C., Glennon, C., Zwaka, T. P., and Thomson, J. A. (2002). BMP4 initiates human embryonic stem cell differentiation to trophoblast. Nat Biotechnol 20, 1261-1264.

Xu, R. H., et al. 2002. "BMP4 initiates human embryonic stem cell differentiation to trophoblast." *Nat Biotechnol* 20:1261-1264.

Yamout, B., Hourani, R., Salti, H., Barada, W., El-Haj, T., Al-Kutoubi, A., Herlopian, A., Baz, E. K., Mahfouz, R., Khalil-Hamdan, R., et al. (2010). Bone marrow mesenchymal stem cell transplantation in patients with multiple sclerosis: a pilot study. J Neuroimmunol 227, 185-189.

Zappia, E., Casazza, S., Pedemonte, E., Benvenuto, F., Bonanni, I., Gerdoni, E., Giunti, D., Ceravolo, A., Cazzanti, F., Frassoni, F., et al. (2005). Mesenchymal stem cells ameliorate experimental autoimmune encephalomyelitis inducing T-cell anergy. Blood 106, 1755-1761.

Zhang, J., Li, Y., Chen, J., Cui, Y., Lu, M., Elias, S. B., Mitchell, J. B., Hammill, L., Vanguri, P., and Chopp, M. (2005). Human bone marrow stromal cell treatment improves neurological functional recovery in EAE mice. Exp Neurol 195, 16-26.

While the disclosure has been described with reference to preferred embodiments, it will be understood by those skilled in the art that various changes may be made and equivalents may be substituted for the elements thereof without departing from the scope of the disclosure. In addition, many modifications may be made to adapt the teaching to particular use, application, manufacturing conditions, use conditions, composition, medium, size, and/or materials without departing from the essential scope and spirit of the disclosure. Therefore, it is intended that the disclosure not be limited to the particular embodiments and best mode contemplated for carrying out as described herein. Such modifications are intended to fall within the scope of the appended claims.

All references cited herein are incorporated by reference in their entireties and for all purposes to the same extent as if each individual publication or patent or patent application was specifically and individually indicated to be incorporated by reference in its entirety for all purposes.

The invention claimed is:

1. A method of producing human trophoblast-derived mesenchymal stem cells (T-MSCs) from human embryonic stem cells (hESCs) or induced pluripotent stem cells (iPSCs), the method comprising:
   (a) culturing hESCs or iPSCs in a medium comprising bone morphogenetic protein-4 (BMP-4), and optionally a TGFβ inhibitor, for a first time period of 1 to 5 days sufficient for the hESCs or iPSCs to differentiate into trophoblast cells;
   (b) dissociating the trophoblast cells into single trophoblast cells; and
   (c) plating the single trophoblast cells from step (b) onto gelatin, vitronectin, laminin, fibronectin, Matrigel or collagen-coated plates, and culturing said single trophoblast cells for a second time period of 4 to 10 days in a mesenchymal stem cell (MSC) growth medium containing LIF, bFGF or PDGF, or a combination thereof, thereby producing human T-MSCs.

2. The method of claim 1, where the TGFβ inhibitor is an SB431542, A83-01 or ALK5 inhibitor.

3. The method of claim 1 wherein, prior to step (a), hESCs are cultured by a method comprising the following steps:
   (i) culturing the hESCs to about 80% confluency on Matrigel-coated plates;
   (ii) dissociating the hESCs under suitable conditions;
   (iii) isolating the hESCs; and
   (iv) washing the hESCs.

4. The method of claim 1, wherein the concentration of BMP4 is about 1 to about 100 ng/ml.

5. The method of claim 1, wherein the population of human T-MSCs: (i) comprises greater than 95% of cells expressing CD73, CD90, CD105, CD146, and CD44; (ii) comprises greater than 80% of cells expressing CD13, CD29, CD54, CD49E; (iii) comprises less than 5% of cells expressing CD45, CD34, CD31 and SSEA4; (iv)

expresses IL-10 and TGFβ; (v) comprises less than 2% of cells expressing IL-6, IL-12 and TNFα; and (vi) comprises less than 0.001% of cells co-expressing OCT4, NANOG, TRA-1-60 and SSEA4.

6. The method of claim 5, wherein the human T-MSCs do not express MMP2 and RAGE.

7. The method of claim 5, wherein the T-MSC cells have low expression of IFNγR1 and IFNγR2 compared to expression of IFNγR1 and IFNγR2 of bone marrow-derived mesenchymal stem cells (BM-MSC).

8. The method of claim 5, wherein the human T-MSCs further express CD73 and do not express IL-6.

9. The method of claim 5, wherein the human T-MSCs further express at least one cell marker selected from the group consisting of CD90, CD105, CD13, CD29, CD54, CD146, CD166, and CD44; do not express at least one marker selected from the group consisting of CD34, CD31, and CD45; and do not express at least one marker selected from the group consisting of MMP, RAGE, IFNγR1, IFNγR2, IL-12, TNFα and VCAM1.

10. The method of claim 5, wherein the human T-MSCs are irradiated.

11. The method of claim 7, wherein the human T-MSCs are irradiated with gamma-irradiation.

12. A method of producing human trophoblast-derived mesenchymal stem cells from human embryonic stem cells (hESCs) or induced pluripotent stem cells (iPSCs), the method comprising:
  (a) culturing hESCs or iPSCs in a medium comprising bone morphogenetic protein-4 (BMP-4) for 1½ to 5 days for the hESC or iPSC to differentiate into trophoblast cells, and optionally with a TGFβ inhibitor;
  (b) isolating the trophoblast cells;
  (c) dissociating the trophoblast cells from step (b) into single trophoblast cells; and
  (d) plating the single trophoblast cells from step (c) onto Matrigel-coated plates and culturing said single trophoblast cells for 4-10 days in a mesenchymal stem cell (MSC) growth medium containing serum, knockout serum replacement (KOSR), or in a serum-free medium, in an amount sufficient to induce differentiation of the single trophoblast cells into human trophoblast-derived mesenchymal stem cells; wherein at least 90% of the human trophoblast-derived mesenchymal stem cells express CD73.

* * * * *